US005766939A

United States Patent [19]
Conneely et al.

[11] Patent Number: 5,766,939
[45] Date of Patent: Jun. 16, 1998

[54] PRODUCTION OF RECOMBINANT LACTOFERRIN AND LACTOFERRIN POLYPEPTIDES USING CDNA SEQUENCES IN VARIOUS ORGANISMS

[75] Inventors: Orla M. Conneely, Houston, Tex.; Denis R. Headon, Galway, Ireland; Bert W. O'Malley; Gregory S. May, both of Houston, Tex.

[73] Assignee: Baylor College of Medicine, Houston, Tex.

[21] Appl. No.: 453,703

[22] Filed: May 30, 1995

Related U.S. Application Data

[60] Division of Ser. No. 145,681, Oct. 28, 1993, Pat. No. 5,571,691, which is a continuation-in-part of Ser. No. 967,947, Oct. 27, 1992, abandoned, and Ser. No. 873,304, Apr. 24, 1992, abandoned, said Ser. No. 967,947, is a continuation of Ser. No. 348,270, May 5, 1989, abandoned.

[51] Int. Cl.[6] .................. C07K 14/79; C07K 14/435; C12N 15/70; C12N 15/74
[52] U.S. Cl. .................. 435/320.1; 435/69.1; 435/172.3; 435/252.33; 435/320.1; 530/324; 530/350; 530/400; 536/23.5; 935/10; 935/11; 935/29; 935/72; 935/73
[58] Field of Search .................. 435/69.1, 172.3, 435/252.3, 254.11, 254.21, 254.23, 254.3, 320.1; 530/412, 23.5

[56] References Cited

U.S. PATENT DOCUMENTS

| | | | |
|---|---|---|---|
| 4,289,690 | 9/1981 | Pestka et al. | 530/351 |
| 4,394,443 | 7/1983 | Weissman et al. | 435/6 |
| 4,634,665 | 1/1987 | Axel et al. | 435/69.1 |
| 4,652,639 | 3/1987 | Stabinsky | 435/91.52 |
| 4,668,771 | 5/1987 | Kawakami et al. | 530/366 |
| 4,703,008 | 10/1987 | Lin | 435/240.2 |
| 4,710,465 | 12/1987 | Weissman et al. | 435/6 |
| 4,726,948 | 2/1988 | Prieels et al. | 424/94.4 |
| 4,740,461 | 4/1988 | Kaufman | 435/69.1 |
| 4,766,075 | 8/1988 | Goeddel et al. | 435/240.2 |
| 4,800,159 | 1/1989 | Mullis et al. | 435/172.3 |
| 4,886,747 | 12/1989 | Derynck et al. | 435/69.4 |
| 4,959,318 | 9/1990 | Foster et al. | 435/172.3 |
| 4,965,190 | 10/1990 | Woo et al. | 435/6 |
| 5,019,508 | 5/1991 | Johnson et al. | 435/198 |
| 5,081,227 | 1/1992 | Millan | 530/328 |
| 5,155,037 | 10/1992 | Summers | 435/240.2 |
| 5,304,633 | 4/1994 | Tomita et al. | 530/326 |

FOREIGN PATENT DOCUMENTS

| | | |
|---|---|---|
| 5566991 | 8/1993 | European Pat. Off. . |
| 8700232 | 3/1987 | France . |
| 8700119 | 7/1987 | WIPO . |
| 8901969 | 3/1989 | WIPO . |
| WO 91/05045 | 4/1991 | WIPO . |
| 9204012 | 12/1992 | WIPO . |

OTHER PUBLICATIONS

M. W. Rey et al. 1990 "Complete Nucleotide Sequence of Human Mammary Gland Lactoferrin" *Nucleic Acids Research* 18:5288, No. 17.

(List continued on next page.)

*Primary Examiner*—Robert A. Wax
*Assistant Examiner*—William W. Moore
*Attorney, Agent, or Firm*—Albert P. Halluin, Esq.; Pennie & Edmonds

[57] ABSTRACT

The verified cDNA sequences for human, bovine and porcine lactoferrin protein have been used to prepare recombinant lactoferrin for therapeutic and nutritional applications. Regions of the cDNA such as the Fe binding sites can be used to make an hLF polypeptide product.

The present invention provides novel plasmids, transfected eucaryotic cells and methods of producing these plasmids and transfected eucaryotic cells. The novel plasmid contains the cDNA for lactoferrin protein. Methods for the production of lactoferrin protein in fungi and bacteria are also provided. Thus, the present invention provides an efficient and economical means for the production of recombinant lactoferrin protein and lactoferrin related polypeptides.

8 Claims, 65 Drawing Sheets

OTHER PUBLICATIONS

S.A. Osmani et al. 1987 "Regulation of the mRNA Levels of nimA, A Gene Required for the G2–M Transition in *Aspergillus nidulans*" *J. Cell Biol.* 104:1495–1504, No. 23.

C.D. Rasmussen et al., 1990, "Characterization and Expression of the Unique Calmodulin Gene of *Aspergillus nidulans*" *J. Biol. Chem.* 265:13767–13775.

P. Vilja et al., 1985, "A Rapid and Sensitive Non–Competitive Avidin–Biotin Assay for Lactoferrin," *J. Immunol. Methods* 76:73–83.

S. Tabor et al., 1985, "A Bacteriophage T7 RNA Polymerase/Promoter System for Controlled Exclusive Expression of Specific Genes," *Proc. Natl. Acad. Sci. U.S.A.* 82:1074–1078.

P.P. Ward et al., 1992, "Production of Biologically Active Recombinant Human Lactoferrin in *Aspergillus oryzae*," *Biotechnology* 10:784–789.

D.P. McDonnell et al., 1991, "High Level Expression of Biologically Active Estrogen Receptor in *Saccharomyces cerevisiae*," *J. Steroid Biochem. Molec. Biol.* 39:291–297, No. 3.

H. Ito et al., 1983, "Transformation of Intact Yeast Cells Treated with Alkali Cations," *J. Bacteriol.* 153:163–168, No. 1.

R.B. Waring et al., 1989, "Characterization of an Inducible Expression System in *Aspergillus nidulans* Using alcA and Tubulin–Coding Genes," *Gene* 79:119–130.

G.S. May et al., 1989, "The Highly Divergent Beta–Tubulins of *Aspergillus nidulans* are Functionally Interchangeable," *J. Cell Biol.* 109:2267–2274.

U.K. Laemmli et al., 1970, "Cleavage of Structural Proteins During the Assembly of the Head of Bacteriophage T4," *Nature* 227:680–685.

H. Towbin et al., 1979, "Electrophoretic Transfer of Proteins from Polyacrylamide Gels to Nitrocellulose Sheets: Procedure and Some Applications," *Proc. Natl. Acad. Sci. U.S.A.* 76:4350–4354, No. 9.

J.M. Bluard–Deconinck et al., 1978, "Iron Binding Fragments from the N–Terminal and C–Terminal Regions of Human Lactoferrin," *Biochem. J.* 171:321–327.

A.R. Goodey, 1993, "The Production of Heterologous Plasma Proteins" *TIBTECH* 11:430.433.

D. Ish–Horowicz et al., 1981, "Rapid and Efficient Cosmid Cloning," *Nucleic Acids Res.* 9:2989–2998, No. 13.

G. Sofer et al., Nov. 12, 1993, "Designing an Optimal Chromatographic Purification Scheme for Proteins," *Biotechniques* 198–203.

1985, "Protective Proteins in Milk" *Bulletin of the International Dairy Federation* No. 191.

G. Sawatzki, 1987, "The Role of Iron Binding Proteins in Bacterial Infections," *Iron Transport in Microbes, Plants and Animals* G. Winkelmann et al., (Eds.) 477–488.

J. Montreuil et al., 1985, "Human Lactotransferrin: Structure and Function," *Proteins of Iron Storage and Transport* G. Spik et al., (Eds.) 25–38.

B.F. Andersen et al., 1987, "Structure of Human Lactoferrin at 3.2 Å Resolution," *Proc. Natl. Acad. Sci. U.S.A.* 84:1769–1773.

*Promega Catalog*, pp. 7, 13–15, 1984.

R.R. Arnold et al., 1977, "A Bactericidal Effect for Human Lactoferrin," *Science* 197:263–265.

J. Van Brunt, 1986, "Fungi: The Perfect Hosts?," *Biotechnology* 4:1057–1062.

T. Christensen et al., 1988, "High Level Expression of Recombinant Genes in *Aspergillus oryzae*," *Biotechnolgoy* 6:1419–1422.

M.P. Kolotila et al., 1988, "Stimulation of Neutrophil Actin Polymerization and Degranulation by Opsinized and Unopsinized *Candida albicans* Hyphae and Zymosan," *Infect. Immun.* 56:2016–2022 No. 8.

T. Soukka et a., 1992, "Fungicidal Effect of Human Lactoferrin against *Candida albicans*," *FEMS Microbiol. Lett.* 90:223–228.

E.C. Theil et al., 1987, "The Storage and Transport of Iron in Animal Cells," *Iron Transport in Nicorobes, plants and Animals* G. Winkelmann et al., (Eds.) 491–520.

Q. Liang et al., 1989, "Screening and Cloning a cDNA Coding for Lactoferrin from Human Mammary Gland," *J. Animal Sci.* 67:154.

M. Metz–Boutique et al., 1984, "Human Lactotransferrin: Amino Acid Sequence and Structural Comparisons with other Transferrins," *Eur. J. Bioc.* 145:659–676.

B. Anderson et al., "Structure of Human Lactoferrin: Crystallagraphic Structure Analysis and Refinement at 2.8 Å Resolution," *J. Mol. Biol.* 209:711–734.

K.M. Stowell et al., 1991, "Epression of Cloned Human Lactoferrin in Baby–Hamster Kidney Cells," *Biochem. J.* 276:349–355.

P. Mead et al., 1990, "cDNA and Protein Sequence of Bovine Lactoferrin," *Nucleic Acids Res.* 18:7167, No. 18.

M.J. Powell et al., 1990, "Nucleotide Sequence of Human Lactoferrin cDNA," *Nucleic Acids Res.* 18:4013, No. 13.

B. Pentecost et al., 1987, "Lactoferrin is the Major Estrogen Inducible Protein of Mouse Uterine Secretions," *J. Biol. Chem.* 262:10134–10139, No. 21.

T. Rado et al., 1987, "Isolation of Lactoferrin cDNA from a Human Myeloid Library and Expressions of mRNA During Normal and Leukemic Myelopoiesis," *Blood* 70:989–993, No. 4.

A. Pierce et al., 1991, "Molecular Cloning and Sequence Analysis of Bovine Lactotransferrin," *Eur. J. Bioch.* 196:177–184.

J.P. Lydon et al., 1992, "Nucleotide and Primary Amino Acid Sequence of Porcine Lactoferrin," *Biochim. Biophys. Acta* 1132:97–99.

L.J. Alexander et al., 1992, "Cloning and Sequencing of the Porcine Lactoferrin cDNA," *Animal Genetics* 23:251–256.

W.M. Bellamy et al., 1992, "Identification of the Bacteriocidal Domain of Lactoferrin," *Biochim. Biophys. Acta* 1121:130–136.

W.M. Bellamy et al., 1992, "Antibacterial Spectrum of Lactoferricin B, A Potent Bactericidal Peptide Derived from the N–Terminal Region of Bovine Lactoferrin," *J. App. Bact* 73:472–479.

F. Yang et al., 1984, "Human Transferrin: cDNA Characterization and Chromosomal Localization," *Proc. Natl. Acad. Sci. U.S.A.* 81:2752–2756.

B. Huge–Jensen et al., 1989, "*Rhizomucor miehei* Triglyceride Lipase is Processed and Secreted from Transformed *Aspergillus oryzae*," *Lipids* 24:781–785, No. 9.

G. von Heijne, 1984, "How Signal Sequences Maintain Cleavage Specificity," *J. Mol. Biol.* 173:243–251.

M.J. Gines et al., 1989, "*Aspergillus oryzae* has Two Nearly Identical Taka–Amylase Genes, Each Containing Eight Introns," *Gene* 79:107–117.

G.G. Wong et al., 1985, "Human GM–CSF: Molecular Cloning of the Complementary DNA and Purification of the Natural and Recombinant Proteins," *Science* 228:810–815.

M. Wigler et al., 1979, "Transformation of Mammalian Cells with Genes from Procaryotes and Eucaryotes," *Cell* 16:777–785.

P.P. Ward et al., 1992, "An Inducible Expression System for the Production of Human Lactoferrin in *Aspergillus nidulans*," *Gene* 122::219–223.

T. Maniatis et al., 1978, "The Isolation of Structural Genes from Libraries of Eucaryotic DNA," *Cell* 15:687–701.

Schaeffer, Evelyne et al., 1987, "Complete structure of the human transferrin gene. Comparison with analogous chicken gene and human pseudogen," *Gene* 56:109–116.

Rose, Timothy M. et al., 1986, "Primary structure of the human melanoma–associated antigen p97 (melanotransferrin) deduced from the mRNA sequence," *Proc. Natl. Acad. Sci. U.S.A.* 83:1261–1265.

Spik, G. et al., 1982, "Characterization and Properties of the human and Bovine Lactoferrins Extracted from the Faeces of Newborn Infants," *Acta Paediatr Scand* 71:979–985.

Tenovuo, Jorma et al., 1986, "Antimicrobial Factors in Whole Saliva of Human Infants," *Infection and Immunity* 51:49–53.

Ambruso, Daniel R. et al., 1981, "Lactoferrin Enhances Hydroxyl Radical Production of Human Neutrophils, Neutrophil Particulate Fractions, and an Enzymatic Generating System," *J. Clin. Invest.* 67:352–360.

Reid, K.B.M., Biochemical Journal, vol. 231, "Molecular cloning and characterization of the complementary DNA and gene coding for the B–chain of the subcomponent C1q of the human complement system", pp. 729–735, 1985.

Fortkamp, E., et al., DNA, vol. 5, No. 6, "Cloning and Expression in *Escherichia coli* of a Synthetic DNA for Hirudin, the Blood Coagulation Inhibitor in the Leech", pp. 511–517, 1986.

Wei, X., et al., Blood, vol. 72, No. 5, "Characterization of the complete cDNA sequence of human neutrophil lactoferrin and isolation of genomic clones", Supplement 1, p. 155a, Abstract 530, 1988.

Goodman, R.E., et al., Biochemical and Biophysical Research Communications, vol. 180, No. 1, "Bovine Lactoferrin mRNA: Sequence, Analysis, and Expression in the Mammary Gland", pp. 75–84, 1991.

LeGrand, D., et al., Biochimica et Biophysica Acta, vol. 787, No. 1, "Characterization and Localization of an Iron–binding 18–kDa Glycopeptide Isolated from the N–Terminal Half of Human Lactotransferrin", pp. 90–96, 1984.

Teng, C.T., et al., Somatic Cell and Molecular Genetics, vol. 13, No. 6, "Assignment of the Lactotransferrin Gene to Human Chromosome 3 and to Mouse Chromosome 9", pp. 689–693, 1987.

Panella, T.J., et al., Cancer Research, vol. 51, "Polymorphism and Altered Methylation of the Lactoferrin Gene in Normal Leukocytes, Leukemic Cells and Breast Cancer", pp. 3037–3043, 1991.

Campbell, T., et al., British Journal of Cancer, vol. 65, No. 1, "Isolation of a lactoferrin cDNA clone and its expression in human breast cancer", pp. 19–26, 1992.

Shirsat, N.V., et al., Gene, vol. 110, "Structure of the murine lactotransferrin gene is similar to the structure of the other transferrin–encoding genes and shares a putative regulartoy region with the murine myeloperoxidase gene", pp. 229–234, 1992.

Cunningham, G. A., et al., Biochemical and Biophysical Research Communications, vol. 189, No. 3, "Structural Organization of the Mouse Lactoferrin Gene", pp. 1725–1731, 1992.

Mount, S. M., Nucleic Acids Research, vol. 10, No.2, "A catalogue of splice junction sequences", pp. 459–472, 1982.

```
                                                           1
                                                    GAATTCC GACCGCAGAC
   18
   ATG AAA CTT GTC TTC CTC GTC CTG CTG TTC CTC GGG GCC CTC GGA CTG
   met lys leu val phe leu val leu leu phe leu gly ala leu gly leu
     1
   66
   TGT CTG GCT GGC CGT AGG AGA AGG AGT GTT CAG TGG TGC ACC GTA TCC
   cys leu ala gly arg arg arg arg ser val gln trp cys thr val ser
    17
  114
   CAA CCC GAG GCC ACA AAA TGC TTC CAA TGG CAA AGG AAT ATG AGA AGA
   gln pro glu ala thr lys cys phe gln trp gln arg asn met arg arg
    33
  162
   GTG CGT GGC CCT CCT GTC AGC TGC ATA AAG AGA GAC TCC CCC ATC CAG
   val arg gly pro pro val ser cys ile lys arg asp ser pro ile gln
    49
  210
   TGT ATC CAG GCC ATT GCG GAA AAC AGG GCC GAT GCT GTG ACC CTT GAT
   cys ile gln ala ile ala glu asn arg ala asp ala val thr leu asp
    65
  258
   GGT GGT TTC ATA TAC GAG GCA GGC CTG GCC CCC TAC AAA CTC CGA CCT
   gly gly phe ile tyr glu ala gly leu ala pro tyr lys leu arg pro
    81
  306
   GTA GCG GCG GAA GTC TAC GGG ACC GAA AGA CAG CCA CGA ACT CAC TAT
   val ala ala glu val tyr gly thr glu arg gln pro arg thr his tyr
    97
  354
   TAT GCC GTG GCT GTG GTG AAG AAG GGC GGC AGC TTT CAG CTG AAC GAA
   tyr ala val ala val val lys lys gly gly ser phe gln leu asn glu
   113
  402
   CTG CAA GGT CTG AAG TCC TGC CAC ACA GGC CTT CGC AGG ACC GCT GGA
   leu gln gly leu lys ser cys his thr gly leu arg arg thr ala gly
   129
  450
   TGG AAT GTG CCT ATA GGG ACA CTT CGT CCA TTC TTG AAT TGG ACG GGT
   trp asn val pro ile gly thr leu arg pro phe leu asn trp thr gly
   145
```

FIG. 2A

```
498
    CCA CCT GAG CCC ATT GAG GCA GCT GTG GCC AGG TTC TTC TCA GCC AGC
    pro pro glu pro ile glu ala ala val ala arg phe phe ser ala ser
    161
546
    TGT GTT CCC GGT GCA GAT AAA GGA CAG TTC CCC AAC CTG TGT CGC CTG
    cys val pro gly ala asp lys gly gln phe pro asn leu cys arg leu
    177
594
    TGT GCG GGG ACA GGG GAA AAC AAA TGT GCC TTC TCC TCC CAG GAA CCG
    cys ala gly thr gly glu asn lys cys ala phe ser ser gln glu pro
    193
642
    TAC TTC AGC TAC TCT GGT GCC TTC AAG TGT CTG AGA GAC GGG GCT GGA
    tyr phe ser tyr ser gly ala phe lys cys leu arg asp gly ala gly
    209
690
    GAC GTG GCT TTT ATC AGA GAG AGC ACA GTG TTT GAG GAC CTG TCA GAC
    asp val ala phe ile arg glu ser thr val phe glu asp leu ser asp
    225
738
    GAG GCT GAA AGG GAC GAG TAT GAG TTA CTC TGC CCA GAC AAC ACT CGG
    glu ala glu arg asp glu tyr glu leu leu cys pro asp asn thr arg
    241
786
    AAG CCA GTG GAC AAG TTC AAA GAC TGC CAT CTG GCC CGG GTC CCT TCT
    lys pro val asp lys phe lys asp cys his leu ala arg val pro ser
    257
834
    CAT GCC GTT GTG GCA CGA AGT GTG AAT GGC AAG GAG GAT GCC ATC TGG
    his ala val val ala arg ser val asn gly lys glu asp ala ile trp
    273
882
    AAT CTT CTC CGC CAG GCA CAG GAA AAG TTT GGA AAG GAC AAG TCA CCG
    asn leu leu arg gln ala gln glu lys phe gly lys asp lys ser pro
    289
930
    AAA TTC CAG CTC TTT GGC TCC CCT ACT GGG CAG AAA GAT CTG CTG TTC
    lys phe gln leu phe gly ser pro thr gly gln lys asp leu leu phe
    305
978
    AAG GAC TCT GCC ATT GGG TTT TCG AGG GTC CCC CCG AGG ATA GAT TCT
    lys asp ser ala ile gly phe ser arg val pro pro arg ile asp ser
    321
1026
    GGG CTG TAC CTT GGC TCC GGC TAC TTC ACT GCC ATC CAG AAC TTG AGG
    gly leu tyr leu gly ser gly tyr phe thr ala ile gln asn leu arg
    337
```

FIG. 2B

```
1074
    AAA AGT GAG GAG GAA GTG GCT GCC CGG CGT GCG CGG GTC GTG TGG TGT
    lys ser glu glu glu val ala ala arg arg ala arg val val trp cys
    353
1122
    GCG GTG GGC GAG CAG GAG CTG CGC AAG TGT AAC CAG TGG AGT GGC TTG
    ala val gly glu gln glu leu arg lys cys asn gln trp ser gly leu
    369
1170
    AGC GAA GGC AGC GTG ACC TGC TCC TCG GCC TCC ACC ACA GAG GAC TGC
    ser glu gly ser val thr cys ser ser ala ser thr thr glu asp cys
    385
1218
    ATC GCC CTG GTG CTG AAA GGA GAA GCT GAT GCC ATG AGT TTG GAT GGA
    ile ala leu val leu lys gly glu ala asp ala met ser leu asp gly
    401
1266
    GGA TAT GTG TAC ACT GCA GGC AAA TGT GGT TTG GTG CCT GTC CTG GCA
    gly tyr val tyr thr ala gly lys cys gly leu val pro val leu ala
    417
1314
    GAG AAC TAC AAA TCC CAA CAA AGC AGT GAC CCT GAT CCT AAC TGT GTG
    glu asn tyr lys ser gln gln ser ser asp pro asp pro asn cys val
    433
1362
    GAT AGA CCT GTG GAA GGA TAT CTT GCT GTG GCG GTG GTT AGG AGA TCA
    asp arg pro val glu gly tyr leu ala val ala val val arg arg ser
    449
1410
    GAC ACT AGC CTT ACC TGG AAC TCT GTG AAA GGC AAG AAG TCC TGC CAC
    asp thr ser leu thr trp asn ser val lys gly lys lys ser cys his
    465
1458
    ACC GCC GTG GAC AGG ACT GCA GGC TGG AAT ATC CCC ATG GGC CTG CTC
    thr ala val asp arg thr ala gly trp asn ile pro met gly leu leu
    481
1506
    TTC AAC CAG ACG GGC TCC TGC AAA TTT GAT GAA TAT TTC AGT CAA AGC
    phe asn gln thr gly ser cys lys phe asp glu tyr phe ser gln ser
    497
1554
    TGT GCC CCT GGG TCT GAC CCG AGA TCT AAT CTC TGT GCT CTG TGT ATT
    cys ala pro gly ser asp pro arg ser asn leu cys ala leu cys ile
    513
1602
    GGC GAC GAG CAG GGT GAG AAT AAG TGC GTG CCC AAC AGC AAT GAG AGA
    gly asp glu gln gly glu asn lys cys val pro asn ser asn glu arg
    529
```

FIG. 2C

```
1650
    TAC TAC GGC TAC ACT GGG GCT TTC CGG TGC CTG GCT GAG AAT GCT GGA
    tyr tyr gly tyr thr gly ala phe arg cys leu ala glu asn ala gly
    545
1698
    GAC GTT GCA TTT GTG AAA GAT GTC ACT GTC TTG CAG AAC ACT GAT GGA
    asp val ala phe val lys asp val thr val leu gln asn thr asp gly
    561
1746
    AAT AAC AAT GAG GCA TGG GCT AAG GAT TTG AAG CTG GCA GAC TTT GCG
    asn asn asn glu ala trp ala lys asp leu lys leu ala asp phe ala
    577
1794
    CTG CTG TGC CTC GAT GGC AAA CGG AAG CCT GTG ACT GAG GCT AGA AGC
    leu leu cys leu asp gly lys arg lys pro val thr glu ala arg ser
    593
1842
    TGC CAT CTT GCC ATG GCC CCG AAT CAT GCC GTG GTG TCT CGG ATG GAT
    cys his leu ala met ala pro asn his ala val val ser arg met asp
    609
1890
    AAG GTG GAA CGC CTG AAA CAG GTG CTG CTC CAC CAA CAG GCT AAA TTT
    lys val glu arg leu lys gln val leu leu his gln gln ala lys phe
    625
1938
    GGG AGA AAT GGA TCT GAC TGC CCG GAC AAG TTT TGC TTA TTC CAG TCT
    gly arg asn gly ser asp cys pro asp lys phe cys leu phe gln ser
    641
1986
    GAA ACC AAA AAC CTT CTG TTC AAT GAC AAC ACT GAG TGT CTG GCC AGA
    glu thr lys asn leu leu phe asn asp asn thr glu cys leu ala arg
    657
2034
    CTC CAT GGC AAA ACA ACA TAT GAA AAA TAT TTG GGA CCA CAG TAT GTC
    leu his gly lys thr thr tyr glu lys tyr leu gly pro gln tyr val
    673
2082
    GCA GGC ATT ACT AAT CTG AAA AAG TGC TCA ACC TCC CCC CTC CTG GAA
    ala gly ile thr asn leu lys lys cys ser thr ser pro leu leu glu
    689
2130
    GCC TGT GAA TTC CTC AGG AAG TAA
    ala cys glu phe leu arg lys ***  ACCGAA GAAGATGGCC CAGCTCCCCA
    705
2180
    AGAAAGCCTC AGCCATTCAC TGCCCCAGC TCTTCTCCCC AGGTGTGTTG GGGCCTTGGC
2240
    TCCCCTGCTG AAGGTGGGGA TTGCCCATCC ATCTGCTTAC AATTCCCTGC TGTCGTCTTA
2300
    GCAAGAAGTA AAATGAGAAA TTTTGTTGAA AAAAAAAAA AAAAAAAAA AAAAAAAA
```

FIG. 2D

Mature ∝-Amylase
      ∝-Amlase Signal Sequence   ┌─────────────────────────────
1) ─────────────────── AlaLeuAlaAlaThrProAlaAspTrpArgSerGlnSer Mature Human Lactoferrin
      Lactoferrin Signal Sequence ┌─────────────────────────────
2) ─────────────────── CysLeuAlaGlyArgArgArgArgSerValGlnTrpCys Mature Recombinant Lactoferrin
      ∝-Amylase Signal Sequence  ┌─────────────────────────────
3) ─────────────────── AlaLeuAlaAlaGlyArgArgArgArgSerValGlnTrp

FIG. 8C

```
   1  NNNNGAGCCT TCGTTCCGGA GTCGCCCAG  GACGCCAGCC CATGAAGCTC
  51  TTCGTCCCCG CCCTCCTGTC CCTTGGAGCC CTTGGACTGT GTCTGGCTGC
 101  CCCGAGGAAA AACGTTCGAT GGTGTACCAT CTCCCAACCT GAGTGGTTCA
 151  AATGCCGCAG ATGGCAGTGG AGGATGAAGA AGCTGGGTGC TCCCTCTATC
 201  ACCTGTGTGA GGCGGGCCTT TGCCTTGGAA TGTATTCCGG GCATCGCGGA
 251  GAAAAAGGCG GATGCTGTGA CCCTGGATGG TGGCATGGTG TTTGAGGCGG
 301  GCCGGGACCC CTACAAACTG CGGCCAGTAG CAGCAGAGAT CTATGGGACG
 351  AAAGAGTCTC CCCAAACCCA CTATTATGCT GTGGCCGTCG TGAAGAAGGG
 401  CAGCAACTTT CAGCTGGACC AGCTGCAAGG CCGGAAGTCC TGCCATACGG
 451  GCCTTGGCAG GTCCGCTGGG TGGATCATCC CTATGGGAAT CCTTCGCCCG
 501  TACTTGAGCT GGACAGAGTC ACTCGAGCCC CTCCAGGGAG CTGTGGCTAA
 551  ATTCTTCTCT GCCAGCTGTG TTCCCTGCAT TGATAGACAA CCATACCCCA
 601  ACCTGTGTCA ACTGTGCAAG GGGAGGGGG  AGAACCAGTG TGCCTGCTCC
 651  TCCCGGGAAC CATACTTCGG TTATTCTGGT GCCTTCAAGT GTCTGCAGGA
 701  CGGGCTGGA  GACGTGGCTT TTGTTAAAGA GACGACAGTG TTTGAGAACT
 751  TGCCAGAGAA GGCTGACAGG GACCAGTATG AGCTTCTCTG CCTGAACAAC
 801  AGTCGGGCGC CAGTGGATGC GTTCAAGGAG TGCCACCTGG CCCAGGTCCC
 851  TTCTCATGCT GTCGTGGCCC GAAGTGTGGA TGGCAAGGAA GACTTGATCT
 901  GGAAGCTTCT CAGCAAGGCG CAGGAGAAAT CTGGAAAAA  CAAGTCTGG
 951  AGCTTCCAGC TCTTTGGCTC TCCACCCGGC CAGAGGGACC TGCTGTTCAA
1001  AGACTCTGCT CTTGGGTTTT TGAGGATCCC CTCGAAGGTA GATTCGGCG
1051  TGTACCTGGG CTCCCGCTAC TTGACCACCT TGAAGAACCT CAGGGAAACT
1101  GCGGAGGAGG TGAAGGCGCG GTACACCAGG GTCGTGTGT  GTGCCGTGGG
1151  ACCTGAGGAG CAGAAGAAGT GCCAGCAGTG GAGCCAGCAC AGCGGCCAGA
1201  ACGTGACCTG TGCCACGGCG TCCACCACTG AGGACTGCAT CCTCCTGGTC
1251  CTGAAAGGGG AAGCAGATGC CCTGAACTTC GATGGAGGAT ATATCTACAC
1301  TGCGGGCAAG TGTGGCCTGG TGCCTGTCCT GGCAGAGAAT CGGAAATCT
1351  CCAAACACAG TAGCCTAGAT TGTGTGCTGA GACCAAGGA  AGGTACCTT
1401  GCCGTGGCAG TTGTCAAGAA AGCAAATGAG GGCTGACAT  GGATTCTCT
```

FIG. 14A

```
1451    GAAAGACAAG AAGTCGTGCC ACACCGCCGT GGACAGGACT GCAGGCTGGA
1501    ACATCCCCAT GGGCCTGATC GTCAACCAGA CAGGCTCCTG CGCATTTGAT
1551    GAATTCTTTA GTCAGAGCTG TGCCCCTGGG GCTGACCCGA ATCCAGACT
1601    CTGTGCCTTG TGTGCTGGCG ATGACCAGGG CCTGGACAAG TGTGTGCCCA
1651    ACTCTAAGGA GAAGTACTAT GGCTATACCG GGGCTTTCAG GTGCCTGGCT
1701    GAGGACGTTG GGACGTTGC CTTTGTGAAA AACGACACAG TCTGGGAGAA
1751    CACGAATGGA GAGAGCACTG CAGACTGGGC TAAGAACTTG AATCGTGAGG
1801    ACTTCAGGTT GCTCTGCCTC GATGGCACCA GGAAGCCTGT GACGGAGGCT
1851    CAGAGCTGCC ACCTGGCGGT GGCCCCGAAT CACGCTGTGC TGTCTCGGAG
1901    CGATAGGGCA GCACACGTGA ACAGGTGCT GCTCCACCAG CAGGCTCTGT
1951    TTGGGAAAAA TGGAAAAAAC TGCCCGGACA AGTTTGTTT GTTCAAATCT
2001    GAAACCAAAA ACCTTCTGTT CAATGACAAC ACTGAGTGTC TGGCCAAACT
2051    TGGAGGCAGA CCAACGTATG AAGAATATTT GGGACAGAG TATGTCACGG
2101    CCATTGCCAA CCTGAAAAAA TGCTCAACCT CCCCGCTTCT GGAAGCCTGC
2151    GCCTTCCTGA CGAGGTAAAG CCTGCAAAGA AGCTAGCCTG CCTCCCTGGG
2201    CCTCAGCTCC TCCCTGCTCT CAGCCCCAAT CTCCAGGCGC GAGGGACCTT
2251    CCTCTCCCTT CCTGAAGTCG GATTTTTGCC AAGCTCATCA GTATTTACAA
2301    TTCCCTGCTG TCATTTTAGC AAGAAATAAA ATTAGAAATG CTGTTGAAAA
2351    A
```

FIG. 14B

```
MKLFVPALLSLGALGLCLAAPRKNVRWCTISQPEWFKCRRWQWRMKKLGAPSITCVRRAFAL
ECIPGIAEKKADAVTLDGGMVFEAGRDPYKLRPVAAEIYGTKESPQTHYYAVAVVKKGSNFQ
LDQLQGRKSCHTGLGRSAGWIIPMGILRPYLSWTESLEPLQGAVAKFFSASCVPCIDRQAYP
NLCQLCKGEGENQCACSSREPYFGYSGAFKCLQDGAGDVAFVKETTVFENLPEKADRDQYEL
LCLNNSRAPVDAFKECHLAQVPSHAVVARSVDGKEDLIWKLLSKAQEKSGKNKSRSFQLFGS
PPGQRDLLFKDSALGFLRIPSKVDSALYLGSRYLTTLKNLRETAEEVKARYTRVVWCAVGPE
EQKKCQQWSQQSGQNVTCATASTTDDCIVLVLKGEADALNLDGGYIYTAGKCGLVPVLAENR
KSSKHSSLDCVLRPTEGYLAVAVVKKANEGLTWNSLKDKKSCHTAVDRTAGWNIPMGLIVNQ
TGSCAFDEFFSQSCAPGADPKSRLCALCAGDDQGLDKCVPNSKEKYYGYTGAFRCLAEDVGD
VAFVKNDTVWENTNGESTADWAKNLNREDFRLLCLDGTRKPVTEAQSCHLAVAPNHAVVSRS
DRAAHVKQVLLHQQALFGKNGKNCPDKFCLFKSETKNLLFNDNTECLAKLGGRPTYEEYLGT
EYVTAIANLKKCSTSPLLEACAFLTR
```

FIG. 14C

```
   1  ACATGAAGCT CTTCATCCCC GCCCTGCTGT TCCTCGGGAC ACTTGGACTG
  51  TGTCTGGCTG CCCCTAAGAA AGGGGTTCGA TGGTGTGTCA TATCCACAGC
 101  AGAGTATTCA AAATGCCGCC AGTGGCAATC AAAGATAAGA AGAACTAATC
 151  CCATGTTCTG CATAAGGAGG GCTTCTCCCA CTGACTGTAT CCGGGCCATC
 201  GCGGCAAAAA GGGCAGATGC TGTGACCCTT GATGGTGGTT TGGTGTTTGA
 251  AGCAGACCAG TACAAACTGC GGCCGGTAGC AGCGGAGATC TACGGGACAG
 301  AAGAGAATCC CCAAACCTAC TATTATGCTG TGGCTGTAGT GAAGAAAGGT
 331  TTCAACTTTC AGAACCAGCT ACAAGGTCGA AAGTCCTGCC ACACAGGCCT
 401  TGGCAGGTCT GCCGGGTGGA ATATCCCTAT AGGTTACTT CGCCGGTTCT
 451  TGGACTGGGC AGGGCCACCT GAGCCCTCC AGAAAGCTGT GGCCAAATTC
 501  TTCTCTCAGA GCTGTGTGCC CTGCGCAGAT GGAAATGCGT ATCCCAACCT
 551  GTGTCAGCTG TGCATAGGGA AAGGAAAGA TAAATGTGCT TGTTCCTCCC
 601  AGGAACCGTA TTTTGGCTAT TCCGTGCCT TCAACTGTCT GCACAAAGGG
 651  ATTGGAGATG TGGCTTTTGT CAAGGAGAGT ACAGTGTTTG AGAACCTGCC
 701  ACAGAAGGCT GACCGGGACA AATACGAGCT ACTCTGCCCA GACAATACTC
 751  GAAAGCCAGT GGAAGCATTC AGGGAGTGCC ACCTTGCCCG GTCCCTTCT
 801  CATGCTGTTG TGGCCCGAAG TGTGAATGGC AAGGAGAACT CCATCTGGGA
 851  GCTTCTCTAC CAGTCACAGA AAAGTTTGG AAAAGCAAT CCACAGGAGT
 901  TCCAGCTCTT TGGCTCTCCT GGTCAGCAGA AGGACCTCCT GTTTAGAGAT
 951  GCTACCATCG GGTTTTTGAA GATCCCCTCA AAGATAGATT CTAAGCTGTA
1001  CCTGGGCCTC CCGTACCTTA CTGCCATCCA GGGCCTGAGG GAAACGGCAG
1051  CGGAGGTGGA GGCGCGGCAG GCGAAGGTCG TGTGGTGCGC CGTGGGTCCA
1101  GAGGAGCTGC GCAAGTGCCG GCAGTGGAGC AGCAGAGCA GCCAGAACCT
1151  GAACTGCAGC CTGGCCTCCA CCACCGAGGA CTGCATCGTC CAGGTGCTGA
1201  AAGGAGAAGC TGATGCTATG AGCTTGGATG GAGGATTTAT CTACACTGCG
1251  GGCAAGTGTG GTTTGGTGCC TGTCCTGGCA GAGAACCAAA AATCTCGCCA
1301  AAGCAGTAGC TCAGACTGTG TGCATAGACC AACACAAGGG TATTTTGCCG
1351  TGGCGGTTCT CAGGAAAGCA AATGGTGGTA TCACCTGGAA CTCTGTGAGA
1401  GGCACGAAGT CCTGCCACAC TCCTGTGGAC AGGACAGCAG GCTGGAACAT
```

FIG. 15A

```
1451  CCCCATGGGC CTGCTTGTCA ACCAGACAGG CTCCTGCAAA TTTGACGAAT

1501  TCTTTAGTCA AAGCTGTGCT CCTGGGTCTC AGCCGGGATC CAATCTCTGT

1551  GCACTGTGTG TTGGCAATGA CCAGGGCGTG GACAAGTGTG TGCCCAACAG

1601  TAATGAGAGA TACTATGGTT ACACCGGGGC TTTCAGGTGC CTGGCTGAGA

1651  ATGCTGGGGA TGTGGCGTTT GTGAAAGATG TCACTGTCTT GGACAACACG

1701  AATGGACAGA ACACAGAAGA GTGGGCCAGG GAATTGAGGT CAGATGACTT

1751  TGAGCTGCTG TGCCTTGATG GCACCAGGAA GCCTGTGACT GAGGCTCAGA

1801  ACTGTCACCT GGCTGTGGCC CCAGTCATG CTGTGGTCTC TCGGAAGGAA

1851  AAGGCAGCAC AGGTGGAACA GGTGCTACTC ACTGAGCAGG CTCAGTTTGG

1901  AAGATACGGA AAAGACTGCC CGGACAAGTT TTGCTTGTTC CGGTCTGAGA

1951  CCAAAAACCT TCTGTTCAAC GACAACACGG AGGTTCTGGC CCAACTCCAA

2001  GGCAAAACAA CATACGAAAA ATATTTGGGA TCAGAGTATG TCACAGCCAT

2051  CGCTAACCTG AAACAGTGCT CAGTCTCCC GCTTCTGGAA GCCTGTGCCT

2101  TCATGATGAG GTAAAACCGG AAAGAAGCT GCCGCCTCC CCAGGGGCCT

2151  CAGCTTTCCC TCCTCCCGTC TTGATTCCCA GCTGCCCTGG GCCTGCCTCT

2201  CTCCCTTCCT GAGGGCAGAC TTTGTTCAGC TCATCCGTTT TCACAATTCC

2251  CTCGTGCCG
```

FIG. 15B (Linear) MAPSORT of: hlf2 check: 7473 from: 1 to: 2360
Mismatch: 0 MinCuts = 1 MaxCuts: 10

```
AccI GT'mk_AC
Cuts at:     0    319   2360
   Size:       319   2041
AceIII CAGCTCnnnnnnn'nnnn
Cuts at:     0    948   1125   2183   2219   2360
   Size:       948    177   1058     36    141
   Fragments arranged by size:
              1058    948    177    141     36
AhdI GACnn_n'nnGTC
Cuts at:     0    472   2360
   Size:       472   1888
AlwI GGATCnnnn'n
Cuts at:     0   1341   1955   2360
   Size:      1341    614    405
   Fragments arranged by size:
              1341    614    405
AlwNI CAG_nnn'CTG
Cuts at:     0   1139   1913   2360
   Size:      1139    774    447
   Fragments arranged by size:
              1139    774    447
ApaI G_GGCC'C
Cuts at:     0     56   2360
   Size:        56   2304
ApaBI GCA_nnnnn'TGC
Cuts at:     0   1140   1789   2360
   Size:      1140    649    571
   Fragments arranged by size:
              1140    649    571
ApaLI G'TGCA_C
Cuts at:     0    101   2360
   Size:       101   2259
ApoI r'AATT_y
Cuts at:     0      1    930   1527   1932   2136   2318   2360
   Size:         1    929    597    405    204    182     42
   Fragments arranged by size:
               929    597    405    204    182     42      1
```

FIG. 18A

AvaI C'yCGr_G
Cuts at:   0    48   117   820   1010   1571   2360
  Size:    48   69   703   190   561    789
  Fragments arranged by size:
           789   703   561   190   69    48
AvaII G'GwC_C
Cuts at:   0    325   439   495   725   824   2067   2360
  Size:    325  114   56    230   99    1243  293
  Fragments arranged by size:
           1243  325   293   230   114   99    56
BanI G'GyrC_C
Cuts at:   0    657   1004   1298   1675   2360
  Size:    657  347   294    377    685
  Fragments arranged by size:
           685  657   377    347    294
BanII G_rGCy'C
Cuts at:   0    56    508    1521   2360
  Size:    56   452   1013   839
  Fragments arranged by size:
           1013  839   452   56
BbsI GAAGACnn'nnnn_
Cuts at:   0    20    2360
  Size:    20   2340
BbvI GCAGCnnnnnnnn'nnnn_
Cuts at:   0    168   394   528   1079   1126   1189   1780   1827
  Size:    168  226   134   551   47     63     591    47
Cuts at:   1827  1900  2360
  Size:    73    460
  Fragments arranged by size:
           591   551   460   226   168   134   73   63   47   47
Bce83I CTTGAGnnnnnnnnnnnnnnnn_nn'
Cuts at:   0    1088   1187   2360
  Size:    1088  99    1173
  Fragments arranged by size:
           1173  1088   99
BcefI ACGGCnnnnnnnnnnnn'n_
Cuts at:   0    62    343   823   1447   1670   1855   2360
  Size:    62   281   480   624   223    185    505
  Fragments arranged by size:
           624  505   480   281   223    185    62

FIG. 18B

```
BfaI C'TA_G
Cuts at:    0    952   1414   1834   2360
   Size:      952    462    420    526
   Fragments arranged by size:
              952    526    462    420
BfiI ACTGGG
Cuts at:    0   1664   2360
   Size:     1664    696
BgII GCCn_nnn'nGGC
Cuts at:    0    427    843   1807   2360
   Size:      427    416    964    553
   Fragments arranged by size:
              964    553    427    416
BglII A'GATC_T
Cuts at:    0    965   1575   2360
   Size:      965    610    785
   Fragments arranged by size:
              965    785    610
BmgI GkGCCC
Cuts at:    0    54   1007   1557   1631   2360
   Size:      54    953    550     74    729
   Fragments arranged by size:
              953    729    550     74     54
BpmI CTGGAGnnnnnnnnnnnnnnnn_nn'
Cuts at:    0    706   1714   2360
   Size:      706   1008    646
   Fragments arranged by size:
             1008    706    646
Bpu10I CC'TnA_GC
Cuts at:    0    502   1765   2188   2360
   Size:      502   1263    423    172
   Fragments arranged by size:
             1263    502    423    172
BsaWI w'CCGG_w
Cuts at:    0   1672   2360
   Size:     1672    688
BsaXI ACnnnnnCTCC
Cuts at:    0    87   1037   1268   2360
   Size:      87    950    231   1092
   Fragments arranged by size:
             1092    950    231     87
```

FIG. 18C

BsoI CAACAC
Cuts at:    0    778   2014   2227   2360
   Size:       778   1236    213    133
   Fragments arranged by size:
              1236    778    213    133
BscGI CCCGT
Cuts at:    0    324    494    681   1517   2360
   Size:       324    170    187    836    843
   Fragments arranged by size:
               843    836    324    187    170
BseRI GAGGAGnnnnnnnn_nn'
Cuts at:    0    617   1095   1181   2360
   Size:       617    478     86   1179
   Fragments arranged by size:
              1179    617    478     86
BsgI GTGCAGnnnnnnnnnnnnnnnn_nn'
Cuts at:    0    577   2360
   Size:       577   1783
BsiEI CG_ry'CG
Cuts at:    0     10   2360
   Size:        10   2350
BsiHKAI G_wGCw'C
Cuts at:    0    105    714   1592   2109   2360
   Size:       105    609    878    517    251
   Fragments arranged by size:
               878    609    517    251    105
BsmI GAATG_Cn'
Cuts at:    0   1694   2360
   Size:      1694    666
BsmAI GTCTCn'nnnn_
Cuts at:    0    187    670    682   1690   1882   2360
   Size:       187    483     12   1008    192    478
   Fragments arranged by size:
              1008    483    478    192    187     12
BsmBI CGTCTCn'nnnn_
Cuts at:    0    670    682   1690   2360
   Size:       670     12   1008    670
   Fragments arranged by size:
              1008    670    670     12
BsmFI GGGACnnnnnnnnnn'nnnn_
Cuts at:    0    338    479    614    762    810   2080   2360
   Size:       338    141    135    148     48   1270    280
   Fragments arranged by size:
              1270    338    280    148    141    135     48

FIG. 18D

Bsp24I GACnnnnnnTGGnnnnnnn_nnnnn'
Cuts at: 0   52   84   239   271   569   601   2062   2094
  Size   52   32   155   32   298   32   1461   32
Cuts at: 2094   2360
  Size   266
  Fragments arranged by size:
          1461   298   266   155   52   32   32   32   32
Bsp1286I G_dGCh'C
Cuts at: 0   56   105   508   714   1009   1521   1559   1592
  Size:   56   49   403   206   295   512   38   33
Cuts at: 1592   1633   2109   2360
  Size:   41   476   251
  Fragments arranged by size:
          512   476   403   295   251   206   56   49   41   38   33
BspMI ACCTGCnnnn'nnnn_
Cuts at: 0   1194   2360
  Size:   1194   1166
BsrI ACTG_Gn'
Cuts at: 0   206   789   1154   1667   1979   2360
  Size:   206   583   365   513   312   381
  Fragments arranged by size:
          583   513   381   365   312   206
BsrDI GCAATG_nn'
Cuts at: 0   220   1646   2360
  Size:   220   1426   714
  Fragments arranged by size:
          1426   714   220
BsrGI T'GTAC_A
Cuts at: 0   1273   2360
  Size:   1273   1087
BstXI CCAn_nnnn'nTGG
Cuts at: 0   942   1161   1256   2360
  Size:   942   219   95   1104
  Fragments arranged by size:
          1104   942   219   95
BstYI r'GATC_y
Cuts at: 0   965   1575   1947   2360
  Size:   965   610   372   413
  Fragments arranged by size:
          965   610   413   372

FIG. 18E

Bsu36I CC'TnA_GG
Cuts at:     0    2142    2360
   Size:       2142    218
CjeI ACnnnnnnTGGnnnnnnn'nnnnnn_
Cuts at:     0    79    188    266    563    618    2056 2360
   Size:       79    109    78    297    55    1438    304
   Fragments arranged by size:
             1438    304    297    109    79    78    55
CviRI TG'CA
Cuts at:     0    103    184    404    558    1216    1281    1476    1525
   Size:       103    81    220    154    658    65    195    49
Cuts at:    1525    1704    1730    2360
   Size:       179    26    630
   Fragments arranged by size:
             658    630    220    195    179    154    103    81
             65    49    26
DdeI C'TnA_G
Cuts at:     0    502    536    672    1684    1765    1828    2017    2142
   Size:       502    34    136    1012    81    63    189    125
Cuts at:    2142    2188    2297    2360
   Size:       46    109    63
   Fragments arranged by size:
             1012    502    189    136    125    109    81    63    63    46    34
DpnI GA'TC
Cuts at:     0    967    1348    1406    1577    1949    2360
   Size:       967    381    58    171    372    411
   Fragments arranged by size:
             967    411    381    372    171    58
DraIII CAC_nnn'GTG
Cuts at:     0    852    2020    2360
   Size:       852    1168    340
   Fragments arranged by size:
             1168    852    340
DsaI C'CryG_G
Cuts at:     0    358    1462    1492    1852    1870    2036    2360
   Size:       358    1104    30    360    18    166    324
   Fragments arranged by size:
             1104    360    358    324    166    30    18
EaeI y'GGCC_r
Cuts at:     0    74    523    2026    2360
   Size:       74    449    1503    334
   Fragments arranged by size:
             1503    449    334    74

FIG. 18F

EarI CTCTTCn'nnn_
Cuts at:    0    152    1509    2216    2360
  Size:        152    1357    707    144
  Fragments arranged by size:
               1357    707    152    144
EciI TCCGCC
Cuts at:    0    313    891    2360
  Size:        313    578    1469
  Fragments arranged by size:
               1469    578    313
Eco57I CTGAAGnnnnnnnnnnnnnnnn_nn'
Cuts at:    0    432    629    2269    2360
  Size:        432    197    1640    91
  Fragments arranged by size:
               1640    432    197    91
EcoNI CCTnn'n_nnAGG
Cuts at:    0    1372    1905    2248    2360
  Size:        1372    533    343    112
  Fragments arranged by size:
               1372    533    343    112
EcoO109I rG'GnC_Cy
Cuts at:    0    52    53    725    824    2231    2360
  Size:        52    1    672    99    1407    129
  Fragments arranged by size:
               1407    672    129    99    52    1
EcoRI G'AATT_C
Cuts at:    0    1    2136    2360
  Size:        1    2135    224
  Fragments arranged by size:
               2135    224    1
EcoRV GAT'ATC
Cuts at:    0    1380    2360
  Size:        1380    980
FauI CCCGCnnnn'nn_
Cuts at:    0    590    1099    2360
  Size:        590    509    1261
  Fragments arranged by size:
               1261    590    509
FokI GGATGnnnnnnnnn'nnnn_
Cuts at:    0    189    460    882    1044    1272    1895    2252    2360
  Size:        189    271    422    162    228    623    357    108
  Fragments arranged by size:
               623    422    357    271    228    189    162    108

FIG. 18G

FspI TGC'GCA
Cuts at:    0    1143    2360
  Size:     1143    1217
GdiII y'GGCC_G
Cuts at:    0    74    2360
  Size:     74    2286
HaeI wGG'CCw
Cuts at:    0    123    219    280    430    525    2028    2360
  Size:     123    96    61    150    95    1503    332
  Fragments arranged by size:
            1503    332    150    123    96    95    61
HgiEII ACCnnnnnnGGT
Cuts at:    0    254    2360
  Size:     254    2106
HhaI G_CG'C
Cuts at:    0    1106    1144    1793    2360
  Size:     1106    38    649    567
  Fragments arranged by size:
            1106    649    567    38
Hin4I GAbnnnnnvTC
Cuts at:    0    471    727    1573    1578    1580    2263    2360
  Size:     471    256    846    5    2    683    97
  Fragments arranged by size:
            846    683    471    256    97    5    2
HinfI G'AnT_C
Cuts at:    0    195    881    981    1020    1862    2032    2360
  Size:     195    686    100    39    842    170    328
  Fragments arranged by size:
            842    686    328    195    170    100    39
HphI GGTGAnnnnnnn_n'
Cuts at:    0    380    916    1626    2360
  Size:     380    536    710    734
  Fragments arranged by size:
            734    710    536    380
MaeII A'CG_T
Cuts at:    0    691    1699    2360
  Size:     691    1008    661
  Fragments arranged by size:
            1008    691    661

FIG. 18H

MaeIII 'GTnAC_
Cuts at:    0     245    760    922    1149   1181   1338   1718   1823
  Size:     245    1:    162    227    32     157    380    105
Cuts at:   1823   2360
  Size:     537
  Fragments arranged by size:
            537    1:    380    245    227    162    157    105    32
MboII GAAGAnnnnn n n'
Cuts at:    0     20     169    383    524    876    1496   2170   2173
  Size:     20    149    214    141    352    620    674    3
Cuts at:   2173   2203   2360
  Size:     30    157
  Fragments arranged by size:
            674   620    352    214    157    149    141    30     20    3
MmeI TCCrACnnnnn:nnnnnnnnnnnn_nn'
Cuts at:    0     30     2360
  Size:     30    2330
MscI TGG'CCA
Cuts at:    0     525    2028   2360
  Size:     525   1503   332
  Fragments arranged by size:
            1503  525    332
MslI CAynn'nnrTG
Cuts at:    0     352    1461   2360
  Size:     352   1109   899
  Fragments arranged by size:
            1109  899    352
MspI C'CG_G
Cuts at:    0     553    821    1042   1097   1673   1959   2360
  Size:     553   268    221    55     576    286    401
  Fragments arranged by size:
            576   553    401    286    268    221    55
MspAlI CmG'CkG
Cuts at:    0     181    392    444    519    544    2360
  Size:     181   211    52     75     25     1816
  Fragments arranged by size:
            1816  211    181    75     52     25
NciI CC's_GG
Cuts at:    0     553    821    822    1097   1959   2360
  Size:     553   268    1      275    862    401
  Fragments arranged by size:
            862   553    401    275    268

FIG. 18I

NcoI C'CATG_G
Cuts at:      0    1492   1852   2036   2360
  Size:       492   360    184    324
  Fragments arranged by size:
              492   360    324    184
NdeI CA'TA_TG
Cuts at:      0    2051   2360
  Size:       2051  309
NlaIII _CATG'
Cuts at:      0    20    837   1253   1496   1762   1856   1869   2040
  Size:       20    817   416    243    266    94     13     171
Cuts at:      2040  2360
  Size:       320
  Fragments arranged by size:
              817   416   320   266   243   171   94   20         13
PleI GAGTCnnnn'n
Cuts at:      0    189    975    2026   2360
  Size:       189   786    1051   334
  Fragments arranged by size:
              1051  786    334    189
Psp5II rG'GwC_Cy
Cuts at:      0    725    824    2360
  Size:       725   99     1536
  Fragments arranged by size:
              1536  725    99
PstI C_TGCA'G
Cuts at:      0    1283   1478   2360
  Size:       1283  195    882
  Fragments arranged by size:
              1283  882    195
PvuII CAG'CTG
Cuts at:      0    181    392    519    544    2360
  Size:       181   211    127    25     1816
  Fragments arranged by size:
              1816  211    181    127    25
RsaI GT'AC
Cuts at:      0    642    1032   1275   2360
  Size:       642   390    243    1085
  Fragments arranged by size:
              1085  642    390    243

FIG. 18J

SanDI GG'GwC_CC
Cuts at:    0    824   2360
   Size:      824   1536
SapI GCTCTTCn'nnn_
Cuts at:    0   1509   2216   2360
   Size:     1509    707    144
   Fragments arranged by size:
            1509    707    144
Sau3AI 'GATC_
Cuts at:    0    965   1346   1404   1575   1947   2360
   Size:      965    381     58    171    372    413
   Fragments arranged by size:
             965    413    381    372    171     58
SfaNI GCATCnnnnn'nnnn_
Cuts at:    0    230    860   1225   1235   2360
   Size:      230    630    365     10   1125
   Fragments arranged by size:
            1125    630    365    230     10
SfcI C'TryA_G
Cuts at:    0    304    460   1279   1474   2360
   Size:      304    156    819    195    886
   Fragments arranged by size:
             886    819    304    195    156
SmaI CCC'GGG
Cuts at:    0    822   2360
   Size:      822   1538
Sse8647I AG'GwC_CT
Cuts at:    0    725   2360
   Size:      725   1635
SspI AAT'ATT
Cuts at:    0   1539   2061   2360
   Size:     1539    522    299
   Fragments arranged by size:
            1539    522    299
StuI AGG'CCT
Cuts at:    0    280    430   2360
   Size:      280    150   1930
   Fragments arranged by size:
            1930    280    150
StyI C'CwwG_G
Cuts at:    0   1034   1492   1852   2036   2234   2360
   Size:     1034    458    360    184    198    126
   Fragments arranged by size:
            1034    458    360    198    184    126

FIG. 18K

TaqI T'CG_A
Cuts at:    0    999    1804    2360
  Size:    999    805    556
  Fragments arranged by size:
           999    805    556
TaqII GACCGAnnnnnnnnn_nn'
Cuts at:    0    342    2360
  Size:    342    2018
TauI GCsGC
Cuts at:    0    310    380    2360
  Size:    310    70    1980
  Fragments arranged by size:
           1980    310    70
TfiI G'AwT_C
Cuts at:    0    881    1020    1862    2360
  Size:    881    139    842    498
  Fragments arranged by size:
           881    842    498    139
ThaI CG'CG
Cuts at:    0    1106    2360
  Size:    1106    1254
TseI GCwGC
Cuts at:    0    182    383    517    1093    1140    1178    1794    1841
  Size:    182    201    134    576    47    38    616    47
Cuts at:    1841    1914    2360
  Size:    73    446
  Fragments arranged by size:
           616    576    446    201    182    134    73    47    38
Tsp45I 'GTsAC_
Cuts at:    0    245    922    1181    1338    1718    1823    2360
  Size:    245    677    259    157    380    105    537
  Fragments arranged by size:
           677    537    380    259    245    157    105
Tsp509I 'AATT_
Cuts at:    0    1    485    930    1527    1932    2136    2280    2318
  Size:    1    484    445    597    405    204    144    38
Cuts at:    2318    2360
  Size:    42
  Fragments arranged by size:
           597    484    445    405    204    144    42    38            1

FIG. 18L

Tth111I GACr'n_nGTC
Cuts at:      0     64    2360
   Size:          64    2296
Tth111II CAA'CAnnnnnnnnn_nn'
Cuts at:      0    708    2360
   Size:         708    1652
UbaCI wGTACw
Cuts at:      0   1275    2360
   Size:        1275    1085
XcmI CCAnnnnn_n'nnnnTGG
Cuts at:      0    484    2360
   Size:         484    1876

Enzymes that do cut and were not excluded:

| | | | | |
|---|---|---|---|---|
| AccI | AceIII | AhdI | AlwI | AlwNI |
| ApaI | ApaBI | ApaLI | ApoI | AvaI |
| AvaII | BanI | BanII | BbsI | BbvI |
| Bce83I | BcefI | BfaI | BfiI | BglI |
| BglII | BmgI | BpmI | Bpu10I | BsaWI |
| BsaXI | BsbI | BscGI | BseRI | BsgI |
| BsiEI | BsiHKAI | BsmI | BsmAI | BsmBI |
| BsmFI | Bsp24I | Bsp1286I | BspMI | BsrI |
| BsrDI | BsrGI | BstXI | BstYI | Bsu36I |
| CjeI | CviRI | DdeI | DpnI | DraIII |
| DsaI | EaeI | EarI | EciI | Eco57I |
| EcoNI | EcoO109I | EcoRI | EcoRV | FauI |
| FokI | FspI | GdiII | HaeI | HgiEII |
| HhaI | Hin4I | HinfI | HphI | MaeII |
| MaeIII | MboII | MmeI | MscI | MslI |
| MspI | MspA1I | NciI | NcoI | NdeI |
| NlaIII | PleI | Psp5II | PstI | PvuII |
| RsaI | SanDI | SapI | Sau3AI | SfaNI |
| SfcI | SmaI | Sse8647I | SspI | StuI |
| StyI | TaqI | TaqII | TauI | TfiI |
| ThaI | TseI | Tsp45I | Tsp509I | Tth111I |
| Tth111II | UbaCIXcmI | | | |

Enzymes that do not cut:

| | | | | |
|---|---|---|---|---|
| AatII | AflII | AflIII | AscI | AvrII |
| BaeI | BamHI | BcgI | BcgI | BclI |
| BplI | Bpu1102I | BsaI | BsaAI | BsaBI |
| BsaHI | BspEI | BspGI | BspLU11I | BsrBI |
| BsrFI | BssHII | BssSI | Bst1107I | BstEII |
| ClaI | DraI | DrdI | DrdII | EagI |
| Eco47III | FseI | HaeII | HgaI | HincII |

FIG. 18M

| | | | | |
|---|---|---|---|---|
| HindIII | HpaI | KpnI | MluI | MseI |
| MunI | NarI | NgoAIV | NheI | NotI |
| NruI | NsiI | NspI | NspV | PacI |
| Pfl1108I | PflMI | PinAI | PmeI | PmlI |
| PshAI | Psp1406I | PvuI | RcaI | RleAI |
| RsrII | SacI | SacII | SalI | ScaI |
| SexAI | SfiI | SgfI | SgrAI | SnaBI |
| SpeI | SphI | SrfI | Sse8387I | SunI |
| SwaI | VspI | XbaI | XhoI | XmnI |

Enzymes excluded; MinCuts: 1  MaxCuts: 10

| | | | | |
|---|---|---|---|---|
| AciI | AluI | BccI | BsaJI | BslI |
| BsoFI | Cac8I | CjeI | CjePI | CjePI |
| CviJI | EcoRII | HaeIII | MnlI | MwoI |
| NlaIV | Sau96I | ScrFI | TspRI | |

FIG. 18N (Linear)MAPSORT of: piglac.gb_om check: 9514 from:1 to :2259
LOCUS     PIGLAC     2259 bp ss-mRNA          MAM
DEFINITION  Sus scrofa lactoferrin mRNA, complete cds.
ACCESSION   M81327 M61828
KEYWORDS    lactoferrin.
SOURCE      Sus scrofa lactational mammary gland cDNA to mRNA.
 ORGANISM  Sus scrofa . . .
Mismatch: 0  MinCuts = 1  MaxCuts: 10
With 209 enzymes: *

AceIII CAGCTCnnnnnnn'nnnn_
Cuts at:    0    497    915    1092    1740    2239    2259
  Size:      497    418    177    648    499    20
  Fragments arranged by size:
             648    499    497    418    177    20
AlwI GGATCnnnn'n_
Cuts at:    0    965    1531    1544    2036    2259
  Size:      965    566    13    492    223
  Fragments arranged by size:
             965    566    492    223    13
AlwNI CAG_nnn'CTG
Cuts at:    0    219    1034    1148    1196    2259
  Size:      219    815    114    48    1063
  Fragments arranged by size:
             1063    815    219    114    48
ApaLI G'TGCA_C
Cuts at:    0    1549    2259
  Size:      1549    710
ApoI r'AATT_y
Cuts at:    0    495    1488    1497    2259
  Size:      495    993    9    762
  Fragments arranged by size:
             993    762    495    9
AvaI C'yCGr_G
Cuts at:    0    33    787    2259
  Size:      33    754    1472
  Fragments arranged by size:
             1472    754    33
AvaII G'GwC_C
Cuts at:    0    791    932    1095    2259
  Size:      791    141    163    1164
  Fragments arranged by size:
             1164    791    163    141

FIG. 19A

BaeI ACnnnnGTAyC
Cuts at:   0   164   2259
  Size:   1614   645

BamHI G'GATC_C
Cuts at:   0   1536   2259
  Size:   1536   723
BanI G'GyrC_C
Cuts at:   0   624   1265   1636   1770   2259
  Size:   624   641   371   134   489
  Fragments arranged by size:
           641   624   489   371   134
BanII G_rGCy'C
Cuts at:   0   475   2259
  Size:   475   1784
BccI CCATC
Cuts at:   0   81   197   233   530   842   956   1025   1229
  Size:   81   116   36   297   312   114   69   204
Cuts at:   1229   1769   2048   2259
  Size:   540   279   211
  Fragments arranged by size:
           540   312   297   279   211   204   116   114   81   69   36
BcefI ACGGCnnnnnnnnnnn'n_
Cuts at:   0   1060   1075   1333   2259
  Size:   1060   15   258   926
  Fragments arranged by size:
           1060   926   258   15
BcgI CGAnnnnnnTGCnnnnnnnnnn_nn'
Cuts at:   0   367   401   2259
  Size:   367   34   1858
  Fragments arranged by size:
           1858   367   34
BfiI ACTGGG
Cuts at:   0   456   1823   2259
  Size:   456   1367   436
  Fragments arranged by size:
           1367   456   436
BgII GCCn_nnn'nGGC
Cuts at:   0   201   394   1768   2259
  Size:   201   193   1374   491
  Fragments arranged by size:
           1374   491   201   193

FIG. 19B

BglII A'GATC_T
Cuts at:   0    286   2259
   Size:      286   1973
BmgI GkGCCC
Cuts at:   0    518   1592   2259
   Size:      518   1074   667
   Fragments arranged by size:
              1074   667   518

BpII GAGnnnnnCTC
Cuts at:   0    171   2259
   Size:      171   2088
BpmI CTGGAGnnnnnnnnnnnnnnn_nn'
Cuts at:   0    462   2259
   Size:      462   1797
Bpu10I CC'TnA_GC
Cuts at:   0    469   2149   2259
   Size:      469   1680   110
   Fragments arranged by size:
              1680   469   110
BsaI GGTCTCn'nnnn_
Cuts at:   0    1531   1841   1941   2259
   Size:      1531   310    100    318
   Fragments arranged by size:
              1531   318    310    100
BsaWI w'CCGG_w
Cuts at:   0    621   1939   2116   2259
   Size:      621   1318   177    143
   Fragments arranged by size:
              1318   621   177   143
BsbI CAACAC
Cuts at:   0    1332   1560   1696   1975   2259
   Size:      1332   228    136    279    284
   Fragments arranged by size:
              1332   284   279   228   136
BscGI CCCGT
Cuts at:   0    294   1011   2166   2259
   Size:      294   717    1155   93
   Fragments arranged by size:
              1155   717   294   93
BseRI GAGGAGnnnnnnnn_nn'
Cuts at:   0    1116   2151   2259
   Size:      1116   1035   108
   Fragments arranged by size:
              1116   1035   108

FIG. 19C

BsgI GTGCAGnnnnnnnnnnnnnnnn_nn'
Cuts at:  0  624  2259
  Size:   624  1635
BsiEI CG_ry'CG
Cuts at:  0  273  2259
  Size:   273  1986
BsiHKAI G_wGCw'C
Cuts at:  0  1520  1553  2070  2259
  Size:   1520  33  517  189
  Fragments arranged by size:
          1520  517  189  33

BslI CCnn_nnn'nnGG
Cuts at:  0  69  449  612  788  1335  1577  1814  2084
  Size:   69  380  163  176  547  242  237  270
Cuts at:  2084  2142  2210  2259
  Size:   58  68  49
  Fragments arranged by size:
          547  380  270  242  237  176  163  69  68  58  49
BsmI GAATG_Cn'
Cuts at:  0  765  1655  2259
  Size:   765  890  604
  Fragments arranged by size:
          890  765  604
BsmAI GTCTCn'nnnn_
Cuts at:  0  1531  1841  1941  2078  2259
  Size:   1531  310  100  137  181
  Fragments arranged by size:
          1531  310  181  137  100
BsmFI GGGACnnnnnnnnnn'nnnn_
Cuts at:  0  50  308  729  777  2259
  Size:   50  258  421  48  1482
  Fragments arranged by size:
          1482  421  258  50  48
Bsp24I GACnnnnnnnTGGnnnnnnn_nnnnn'
Cuts at:  0  37  69  215  247  536  568  2259
  Size:   37  32  146  32  289  32  1691
  Fragments arranged by size:
          1691  289  146  37  32  32  32
Bsp1286I G_dGCh'C
Cuts at:  0  475  520  1520  1553  1594  2070  2259
  Size:   475  45  1000  33  41  476  189
  Fragments arranged by size:
          1000  476  475  189  45  41  33

FIG. 19D

BspGI CTGGAC
Cuts at:    0    1098    1190    2259
  Size:     1098    92    1069
  Fragments arranged by size:
            1098    1069    92
BspMI ACCTGCnnnn'nnnn
Cuts at:    0    394    703    2259
  Size:     394    309    1556
  Fragments arranged by size:
            1556    394    309
BsrI ACTG_Gn'
Cuts at:    0    119    257    459    756    860    1822    2259
  Size:     119    138    202    297    104    962    437
  Fragments arranged by size:
            962    437    297    202    138    119    104
BsrDI GCAATG_nn'
Cuts at:    0    1571    2259
  Size:     1571    688
BsrFI r'CCGG_y
Cuts at:    0    272    442    1117    2259
  Size:     272    170    675    1142
  Fragments arranged by size:
            1142    675    272    170
BssSI C'TCGT_G
Cuts at:    0    2251    2259
  Size:     2251    8
BstXI CCAn_nnnn'nTGG
Cuts at:    0    909    2259
  Size:     909    1350
BstYI r'GATC_y
Cuts at:    0    286    970    1536    2259
  Size:     286    684    566    723
  Fragments arranged by size:
            723    684    566    286
Bsu36I CC'TnA_GG
Cuts at:    0    1035    2209    2259
  Size:     1035    1174    50
  Fragments arranged by size:
            1174    1035    50
Cac8I GCn'nGC
Cuts at:    0    1069    1119    1250    1439    1461    1888    2133    2193
  Size:    1069    50    131    189    22    427    245    60
Cuts at:    2193    2259
  Size:    66
  Fragments arranged by size:
            1069    427    245    189    131    66    60    50    22

FIG. 19E

CjeI ACnnnnnnTGGnnnnnnn'nnnnnn
Cuts at:    0    64   164   242   410   530   585   855   1526
  Size:       64   100    78   168   120    55   270   671
Cuts at: 1526  2259
  Size:     733
  Fragments arranged by size:
           733   671   270   168   120   100    78    64    55
CviRI TG'CA
Cuts at:    0   160   562   641  1156  1183  1322  1486  1551
  Size:      160   402    79   515    27   139   164    65
Cuts at: 1551  2259
  Size:     708
  Fragments arranged by size:
           708   515   402   164   160   139    79    65    27
DpnI GA'TC
Cuts at:    0   288   972  1538  2030  2259
  Size:      288   684   566   492   229
  Fragments arranged by size:
           684   566   492   288   229
DraIII CAC_nnn'GTG
Cuts at:    0  1557  2259
  Size:     1557   702
DrdI GACnn_nn'nnGTC
Cuts at:    0  1185  2259
  Size:     1185  1074
DrdII GAACCA
Cuts at:    0   364  1285  2259
  Size:      364   921   974
  Fragments arranged by size:
           974   921   364
DsaI C'CryG_G
Cuts at:    0  1090  1348  1453  2259
  Size:     1090   258   105   806
  Fragments arranged by size:
          1090   806   258   105
EaeI y'GGCC_r
Cuts at:    0   270   490  2259
  Size:      270   220  1769
  Fragments arranged by size:
          1769   270   220

FIG. 19F

EagI C'GGCC_G
Cuts at:    0    270   2259
   Size:       270   1989
EarI CTCTTCn'nnn_
Cuts at:    0    15   295   1711   2259
   Size:       15   280   1416    548
   Fragments arranged by size:
               1416   548   280   15
EcoNI CCTnn'n_nnAGG
Cuts at:    0    67   2208   2259
   Size:       67   2141    51
   Fragments arranged by size:
               2141    67    51
EcoO109I rG'GnC_Cy
Cuts at:    0    791    932   1031   2145   2259
   Size:       791   141    99   1114   114
   Fragments arranged by size:
               1114   791   141   114   99
EcoRI G'AATT_C
Cuts at:    0    1497   2259
   Size:       1497    762
FauI CCCGCnnnn'nn_
Cuts at:    0    26   1241   2086   2140   2259
   Size:       26   1215    845    54   119
   Fragments arranged by size:
               1215   845   119    54    26
FokI GGATGnnnnnnnnn'nnnn_
Cuts at:    0   1011   1239   1434   1671   2218   2259
   Size:      1011   228   195   237   547   41
   Fragments arranged by size:
               1011   547   237   228   195   41
FspI TGC'GCA
Cuts at:    0    524   1110   2259
   Size:       524   586   1149
   Fragments arranged by size:
               1149   586   524
GdiII y'GGCC_G
Cuts at:    0    270   2259
   Size:       270   1989
HaeI wGG'CCw
Cuts at:    0    397    492   1164   2259
   Size:       397    95    672   1095
   Fragments arranged by size:
               1095   672   397   95

FIG. 19G

HgiEII ACCnnnnnnGGT
Cuts at:    0    230    2259
  Size:        230    2029
HhaI G_CG'C
Cuts at:    0    525    1064    1089    1111    2259
  Size:        525    539    25    22    1148
  Fragments arranged by size:
              1148    539    525    25    22
Hin4I GAbnnnnnvTC
Cuts at:    0    83    171    1235    1541    1791    2259
  Size:        83    88    1064    306    250    468
  Fragments arranged by size:
              1064    468    306    250    88    83
HincII GTy'rAC
Cuts at:    0    1469    2259
  Size:        1469    790
HinfI G'AnT_C
Cuts at:    0    305    987    2173    2259
  Size:        305    682    1186    86
  Fragments arranged by size:
              1186    682    305    86
HphI GGTGAnnnnnnnn_n'
Cuts at:    0    1373    1797    2259
  Size:        1373    424    462
  Fragments arranged by size:
              1373    462    424
MaeIII 'GTnAC_
Cuts at:    0    221    433    862    1617    1679    1784    1803    2039
  Size:        221    212    429    755    62    105    19    236
Cuts at:   2039    2259
  Size:        220
  Fragments arranged by size:
              755    429    236    221    220    212    105    62    19
MboII GAAGAnnnnnnnn_n'
Cuts at:    0    2    151    312    353    491    980    1728    1912
  Size:        2    149    161    41    138    489    748    184
Cuts at:   1912    2259
  Size:        347
  Fragments arranged by size:
              748    489    347    184    161    149    138    41
              2

FIG. 19H

MscI TGG'CCA
Cuts at:   0   492   2259
  Size:    492   1767
MslI CAynn'nnrTG
Cuts at:   0   1422   1452   2259
  Size:    1422   30   807
  Fragments arranged by size:
           1422   807   30
MspA1I CmG'CkG
Cuts at:   0   282   557   1050   2181   2259
  Size:    282   275   493   1131   78
  Fragments arranged by size:
           1131   493   282   275   78
MwoI GCnn_nnn'nnGC
Cuts at:   0   201   210   394   470   810   1068   1135   1138
  Size:    201   9   184   76   340   258   67   3
Cuts at:   1138   1650   1768   2259
  Size:    512   118   491
  Fragments arranged by size:
           512   491   340   258   201   184   118   76   67   9   3
NciI CC's_GG
Cuts at:   0   192   413   714   788   789   1534   1625   1920
  Size:    192   221   301   74   1   745   91   295
Cuts at:   1920   2259
  Size:    339
  Fragments arranged by size:
           745   339   301   295   221   192   91   74   1
NcoI C'CATG_G
Cuts at:   0   1453   2259
  Size:    1453   806
NgoAIV G'CCGG_C
Cuts at:   0   1117   2259
  Size:    1117   1142
NlaIII _CATG'
Cuts at:   0   5   155   804   1457   1830   2105   2259
  Size:    5   150   649   653   373   275   154
  Fragments arranged by size:
           653   649   373   275   154   150   5

FIG. 19I

PflMI CCAn_nnn'nTGG
Cuts at:    0    1577    2259
   Size:    1577    682
Psp5II rG'GwC_Cy
Cuts at:    0    791    932    2259
   Size:    791    141    1327
   Fragments arranged by size:
            1327    791    141
PstI C_TGCA'G
Cuts at:    0    1158    2259
   Size:    1158    1101
PvuII CAG'CTG
Cuts at:    0    557    2181    2259
   Size:    557    1624    78
   Fragments arranged by size:
            1624    557    78
RcaI T'CATG_A
Cuts at:    0    2101    2259
   Size:    2101    158
RsaI GT'AC
Cuts at:    0    261    680    999    1014    2259
   Size:    261    419    319    15    1245
   Fragments arranged by size:
            1245    419    319    261    15
SanDI GG'GwC_CC
Cuts at:    0    791    2259
   Size:    791    1468
SapI GCTCTTCn'nnn_
Cuts at:    0    15    2259
   Size:    15    2244
Sau3AI 'GATC_
Cuts at:    0    286    970    1536    2028    2259
   Size:    286    684    566    492    231
   Fragments arranged by size:
            684    566    492    286    231
SfaNI GCATCnnnnn'nnnn_
Cuts at:    0    206    938    1192    1202    2259
   Size:    206    732    254    10    1057
   Fragments arranged by size:
            1057    732    254    206    10
SfcI C'TryA_G
Cuts at:    0    334    427    1154    2259
   Size:    334    93    727    1105
   Fragments arranged by size:
            1105    727    334    93

FIG. 19J

SmaI CCC'GGG
Cuts at:      0     789    2259
  Size:     789    1470
Sse8647I AG'GwC_CT
Cuts at:      0     932    2259
  Size:     932    1327
SspI AAT'ATT
Cuts at:      0    2022    2259
  Size:    2022     237
StuI AGG'CCT
Cuts at:      0     397    2259
  Size:     397    1862
StyI C'CwwG_G
Cuts at:      0     398    1453    1997    2259
  Size:     398    1055     544     262
  Fragments arranged by size:
           1055     544     398     262
TaqI T'CG_A
Cuts at:      0      77     377     749    2259
  Size:      77     300     372    1510
  Fragments arranged by size:
           1510     372     300      77
TauI GCsGC
Cuts at:      0     116     202     270    1065    2259
  Size:     116      86      68     795    1194
  Fragments arranged by size:
           1194     795     116      86      68
TfiI G'AwT_C
Cuts at:      0     305     987    2173    2259
  Size:     305     682    1186      86
  Fragments arranged by size:
           1186     682     305      86
ThaI CG'CG
Cuts at:      0     201    1064    2259
  Size:     201     863    1195
  Fragments arranged by size:
           1195     863     201
Tsp45I 'GTsAC_
Cuts at:      0     221     862    1679    1784    1803    2039    2259
  Size:     221     641     817     105      19     236     220
  Fragments arranged by size:
            817     641     236     221     220     105      19

FIG. 19K

Tsp509I 'AATT_
Cuts at:    0    495   1488   1497   1731   2244   2259
  Size:     495   993    9     234    513    15
  Fragments arranged by size:
            993   513   495   234    15     9
Tth111I GACn'n_nGTC
Cuts at:    0    49    2259
  Size:     49   2210
Tth111II CAArCAnnnnnnnnn_nn'
Cuts at:    0    234   577   675   1452   1922   2259
  Size:     234   343   98    777    470    337
  Fragments arranged by size:
            777   470   343   337    234    98
UbaCI wGTACw
Cuts at:    0    261   680   2259
  Size:     261   419   1579
  Fragments arranged by size:
            1579  419   261
XcmI CCAnnnnn_n'nnnnTGG
Cuts at:    0    396   1829   2259
  Size:     396   1433   430
  Fragments arranged by size:
            1433  430   396
XmnI GAAnn'nnTTC
Cuts at:    0    9    348    2259
  Size:     9    339   1911
  Fragments arranged by size:
            1911  339   9

Enzymes that do cut and were not excluded:

| | | | | | | | |
|---|---|---|---|---|---|---|---|
| AceIII | AlwI | AlwNI | ApaLI | ApoI | AvaI | AvaII | BaeI |
| BamHI | BanI | BanII | BccI | BcefI | BcgI | BfiI | BglI |
| BglII | BmgI | BplI | BpmI | Bpu10I | BsaI | BsaWI | BsbI |
| BscGI | BseRI | BsgI | BsiEI | BsiHKAI | BslI | BsmI | BsmAI |
| BsmFI | Bsp24I | Bsp1286I | BspGI | BspMI | BsrI | BsrDI | BsrFI |
| BssSI | BstXI | BstYI | Bsu36I | Cac8I | CjeI | CviRI | DpnI |
| DraIII | DrdI | DrdII | DsaI | EaeI | EagI | EarI | EcoNI |
| EcoO109I | EcoRI | FauI | FokI | FspI | GdiII | HaeI | HgiEII |
| HhaI | Hin4I | HincII | HinfI | HphI | MaeIII | MboII | MscI |
| MsII | MspA1I | MwoI | NciI | NcoI | NgoAIV | NlaIII | PflMI |
| Psp5II | PstI | PvuII | RcaI | RsaI | SanDI | SapI | Sau3AI |
| SfaNI | SfcI | SmaI | Sse8647I | SspI | StuI | StyI | TaqI |
| TauI | TfiI | ThaI | Tsp45I | Tsp509I | Tth111I | Tth111II | UbaCI |
| XcmI | XmnI | | | | | | |

FIG. 19L

Enzymes that do not cut:

| AatII | AccI | AflII | AflIII | AhdI | ApaI | ApaBI | AscI |
|-------|------|-------|--------|------|------|-------|------|
| AvrII | BbsI | Bce83I | BclI | BfaI | Bpu1102I | BsaAI | BsaBI |
| BsaHI | BsaXI | BsmBI | BspEI | BspLU11I | BsrBI | BsrGI | BssHII |
| Bst1107I | BstEII | ClaI | DraI | EciI | Eco47III | Eco57I | EcoRV |
| FseI | HaeII | HgaI | HindIII | HpaI | KpnI | MaeII | MluI |
| MmeI | MseI | MunI | NarI | NdeI | NheI | NotI | NruI |
| NsiI | NspI | NspV | PacI | Pfl1108I | PinAI | PleI | PmeI |
| PmlI | PshAI | Psp1406I | PvuI | RleAI | RsrII | SacI | SacII |
| SalI | ScaI | SexAI | SfiI | SgfI | SgrAI | SnaBI | SpeI |
| SphI | SrfI | Sse8387I | SunI | SwaI | TaqI | TaqII | VspI |
| XbaI | XhoI | | | | | | |

Enzymes excluded; MinCuts: 1 MaxCuts: 10

| AciI | AluI | BbvI | BsaJI | BsoFI | CjeI | CjePI | CjePI |
|------|------|------|-------|-------|------|-------|-------|
| CviJI | DdeI | EcoRII | HaeIII | MnlI | MspI | NlaIV | Sau96I |
| ScrFI | TseI | TspRI | | | | | |

FIG. 19M (Linear) MAPSORT of: bovlactof.gb_om check: 2217 from: 1 to: 2351
LOCUS      BOVLACTOF    2351 bp ss-mRNA         MAM
DEFINITION  Bovine lactoferrin mRNA, complete cds.
ACCESSION   M63502
KEYWORDS    lactoferrin.
SOURCE      B.taurus, cDNA to mRNA.
  ORGANISM  Bos taurus . . .
Mismatch: 0  Min.Cuts = 1  MaxCuts: 10
With 209 enzymes: *

AceIII CAGCTCnnnnnnn'nnnn_
Cuts at:    0    494    526    969    1553    1841    2216    2351
   Size:       494     32    443     584     288     375    135
   Fragments arranged by size:
               584    494    443    375    288    135     32
AflIII A'CryG_T
Cuts at:    0    1913    2351
   Size:       1913    438
AhdI GACnn_n'nnGTC
Cuts at:    0    1460    2351
   Size:       1460    891
AlwI GGATCnnnn'n_
Cuts at:    0    480    1019    1032    2351
   Size:       480    539     13    1319
   Fragments arranged by size:
               1319    539    480     13
AlwNI CAG_nnn'CTG
Cuts at:    0    1600    1631    1928    1946    2351
   Size:       1600     31    297     18    405
   Fragments arranged by size:
               1600    405    297     31     18
ApoI r'AATT_y
Cuts at:    0    549    1442    1551    2351
   Size:       549    893    109    800
   Fragments arranged by size:
               893    800    549    109
AvaI C'yCGr_G
Cuts at:    0    101    522    652    2351
   Size:       101    421    130    1699
   Fragments arranged by size:
               1699    421    130    101

FIG. 20A

AvaII G'GwC_C
Cuts at:    0    305   416   460   770   845   986   1149  2244
  Size:        305   111   44    310   75    141   163   1095
Cuts at: 2244  2351
  Size:       107
  Fragments arranged by size:
              1095  310   305   163   141   111   107   75    44
BamHI G'GATC_C
Cuts at:    0    1024  2351
  Size:        1024  1327
BanI G'GyrC_C
Cuts at:    0    678   806   1319  1393  1690  1824  2351
  Size:        678   128   513   74    297   134   527
  Fragments arranged by size:
              678   527   513   297   134   128   74
BanII G_rGCy'C
Cuts at:    0    80    529   1062  1435  2351
  Size:        80    449   533   373   916
  Fragments arranged by size:
              916   533   449   373   80
BbsI GAAGACnn'nnnn_
Cuts at:    0    895   2351
  Size:        895   1456
BbvI GCAGCnnnnnnnn'nnnn_
Cuts at:    0    83    342   409   412   1842  1915  1920  2351
  Size:        83    259   67    3     1430  73    5     431
  Fragments arranged by size:
              1430  431   259   83    73    67    5     3
BccI CCATC
Cuts at:    0    120   128   162   278   881   1283  1823  2351
  Size:        120   8     34    116   603   402   540   528
  Fragments arranged by size:
              603   540   528   402   120   116   34    8
Bce83I CTTGAGnnnnnnnnnnnnnn_nn'
Cuts at:    0    524   2351
  Size:        524   1827
BcefI ACGGCnnnnnnnnnnnn'n_
Cuts at:    0    370   1129  1231  1387  1462  2113  2351
  Size:        370   759   102   156   75    651   238
  Fragments arranged by size:
              759   651   370   238   156   102   75
BfaI C'TA_G
Cuts at:    0    1365  2183  2351
  Size:        1365  818   168
  Fragments arranged by size:
              1365  818   168

FIG. 20B

BfiI ACTGGG
Cuts at:   0   1776   2351
  Size:   1776   575
BgII GCCn_nnn'nGGC
Cuts at:   0   448   1578   1822   2351
  Size:   448   1130   244   529
  Fragments arranged by size:
       1130   529   448   244
BglII A'GATC_T
Cuts at:   0   337   2351
  Size:   337   2014
BmgI GkGCCC
Cuts at:   0   1572   1646   2351
  Size:   1572   74   705
  Fragments arranged by size:
       1572   705   74
BpmI CTGGAGnnnnnnnnnnnnnnnn_nn'
Cuts at:   0   516   727   2216   2351
  Size:   516   211   1489   135
  Fragments arranged by size:
       1489   516   211   135
Bpu10I CC'TnA_GC
Cuts at:   0   1699   2202   2351
  Size:   1699   503   149
  Fragments arranged by size:
       1699   503   149
BsaI GGTCTCn'nnnn_
Cuts at:   0   1373   2351
  Size:   1373   978
BsaAI yAC'GTr
Cuts at:   0   1916   2351
  Size:   1916   435
BsaHI Gr'CG_yC
Cuts at:   0   32   807   1218   2351
  Size:   32   775   411   1133
  Fragments arranged by size:
       1133   775   411   32
BsaWI w'CCGG_w
Cuts at:   0   15   1339   2351
  Size:   15   1324   1012
  Fragments arranged by size:
       1324   1012   15
BsaXI ACnnnnnCTCC
Cuts at:   0   634   1058   2351
  Size:   634   424   1293
  Fragments arranged by size:
       1293   634   424

FIG. 20C

BsbI CAACAC
Cuts at:     0    2029    2351
    Size:     2029    322
BscGI CCCGT
Cuts at:     0    449    498    702    2351
    Size:     449    49    204    1649
    Fragments arranged by size:
            1649    449    204    49
BseRI GAGGAGnnnnnnnn_nn'
Cuts at:     0    638    1119    1170    2198    2351
    Size:     638    481    51    1028    153
    Fragments arranged by size:
            1028    638    481    153    51
BsiHKAI G_wGCw'C
Cuts at:     0    191    1767    2351
    Size:     191    1576    584
    Fragments arranged by size:
            1576    584    191
BsmAI GTCTCn'nnnn_
Cuts at:     0    361    703    723    949    1373    1897    2351
    Size:     361    342    20    226    424    524    454
    Fragments arranged by size:
            524    454    424    361    342    226    20
BsmBI CGTCTCn'nnnn_
Cuts at:     0    703    723    2351
    Size:     703    20    1628
    Fragments arranged by size:
            1628    703    20
BsoFI GC'n_GC
Cuts at:     0    97    155    321    331    401    423    1193    1856
    Size:     97    58    166    10    70    22    770    663
Cuts at:     1856    1909    1929    2351
    Size:     53    20    422
    Fragments arranged by size:
            770    663    422    166    97    70    58    53    22    20    10
Bsp24I GACnnnnnnTGGnnnnnnn_nnnnn'
Cuts at:     0    76    108    260    292    590    622    882    914
    Size:     76    32    152    32    298    32    260    32
Cuts at:     914    1725    1757    2351
    Size:     811    32    594
    Fragments arranged by size:
            811    594    298    260    152    76    32    32    32    32    32

FIG. 20D

Bsp1286I G_dGCh'C
Cuts at:   0    80   191   529   1062   1435   1574   1648   1767
  Size:    80   111   338   533   373    139    74     119
Cuts at:  1767  2351
  Size:   584
  Fragments arranged by size:
          584   533   373   338   139   119   111   80   74
BspEI T'CCGG_A
Cuts at:   0    15   2351
  Size:    15   2336
BspGI CTGGAC
Cuts at:   0    416   511   1634   2351
  Size:    416   95    1123   717
  Fragments arranged by size:
          1123   717   416   95
BspMI ACCTGCnnnn'nnnn_
Cuts at:   0    448   997   2351
  Size:    448   549   1354
  Fragments arranged by size:
          1354   549   448
BsrI ACTG_Gn'
Cuts at:   0    324   635   773   810   1779   2351
  Size:    324   311   138   37    969   572
  Fragments arranged by size:
          969   572   324   311   138   37
BsrBI GAG'CGG
Cuts at:   0    1192   2351
  Size:    1192   1159
BsrDI GCAATG_nn'
Cuts at:   0    2101   2351
  Size:    2101   250
BstXI CCAn_nnnn'nTGG
Cuts at:   0    963   2351
  Size:    963   1388
BstYI r'GATC_y
Cuts at:   0    337   1024   2351
  Size:    337   687   1327
  Fragments arranged by size:
          1327   687   337
Bsu36I CC'TnA_GG
Cuts at:   0    1089   1153   2351
  Size:    1089   64    1198
  Fragments arranged by size:
          1198   1089   64

FIG. 20E

CviRI TG'CA
Cuts at:    0    425    577    616    695    1237    1491    1770    2174
  Size:      425    152    39    79    542    254    279    404
Cuts at:  2174    2351
  Size:      177
  Fragments arranged by size:
             542    425    404    279    254    177    152    79    39
DpnI GA'TC
Cuts at:    0    339    474    897    1026    1518    2351
  Size:      339    135    423    129    492    833
  Fragments arranged by size:
             833    492    423    339    135    129
DraIII CAC_nnn'GTG
Cuts at:    0    1886    2035    2351
  Size:      1886    149    316
  Fragments arranged by size:
             1886    316    149
DrdI GACnn_nn'nnGTC
Cuts at:    0    353    1239    2351
  Size:      353    886    1112
  Fragments arranged by size:
             1112    886    353
DrdII GAACCA
Cuts at:    0    146    634    659    2351
  Size:      146    488    25    1692
  Fragments arranged by size:
             1692    488    146    25
DsaI C'CryG_G
Cuts at:    0    1144    1213    1402    1477    1507    2351
  Size:      1144    69    189    75    30    844
  Fragments arranged by size:
             1144    844    189    75    69    30
EaeI y'GGCC_r
Cuts at:    0    321    382    977    1193    2041    2098    2351
  Size:      321    61    595    216    848    57    253
  Fragments arranged by size:
             848    595    321    253    216    61    57

FIG. 20F

EarI CTCTTCn'nnn_
Cuts at:   0    54    2351
  Size:       54    2297
EciI TCCGCC
Cuts at:   0    259    2351
  Size:       259    2092
Eco57I CTGAAGnnnnnnnnnnnnnnnn_nn'
Cuts at:   0    1787    2283    2351
  Size:       1787    496    68
  Fragments arranged by size:
              1787    496    68
EcoNI CCTnn'n_nnAGG
Cuts at:   0    206    840    1698    2351
  Size:       206    634    858    653
  Fragments arranged by size:
              858    653    634    206
EcoO109I rG'GnC_Cy
Cuts at:   0    305    845    986    1149    1628    2244    2351
  Size:       305    540    141    163    479    616    107
  Fragments arranged by size:
              616    540    479    305    163    141    107
EcoRI G'AATT_C
Cuts at:   0    1442    1551    2351
  Size:       1442    109    800
  Fragments arranged by size:
              1442    800    109
FauI CCCGCnnnn'nn_
Cuts at:   0    65    205    290    1071    1295    2140    2351
  Size:       65    140    85    781    224    845    211
  Fragments arranged by size:
              845    781    224    211    140    85    65
FokI GGATGnnnnnnnnn'nnnn_
Cuts at:   0    185    273    288    462    828    891    1293    1488
  Size:       185    88    15    174    366    63    402    195
Cuts at:  1488    2351
  Size:       863
  Fragments arranged by size:
              863    402    366    195    185    174    88    63    15

FIG. 20G

FspI TGC'GCA
Cuts at:    0    1541    2351
   Size:    1541    810
GdiII y'GGCC_G
Cuts at:    0    321    382    977    1193    2098    2351
   Size:    321    61    595    216    905    253
   Fragments arranged by size:
            905    595    321    253    216    61
HaeI wGG'CCw
Cuts at:    0    1315    2043    2351
   Size:    1315    728    308
   Fragments arranged by size:
            1315    728    308
HaeII r_GCGC'y
Cuts at:    0    810    1050    2351
   Size:    810    240    1301
   Fragments arranged by size:
            1301    810    240
HgaI GACGCnnnnn'nnnnn_
Cuts at:    0    40    1207    2351
   Size:    40    1167    1144
   Fragments arranged by size:
            1167    1144    40
HgiEII ACCnnnnnnnGGT
Cuts at:    0    275    2351
   Size:    275    2076
HhaI G_CG'C
Cuts at:    0    809    920    1049    1118    1542    2151    2239    2351
   Size:    809    111    129    69    424    609    88    112
   Fragments arranged by size:
            809    609    424    129    112    111    88    69
Hin4I GAbnnnnnnvTC
Cuts at:    0    1289    1459    1588    1845    2351
   Size:    1289    170    129    257    506
   Fragments arranged by size:
            1289    506    257    170    129
HincII GTy'rAC
Cuts at:    0    609    1523    2351
   Size:    609    914    828
   Fragments arranged by size:
            914    828    609

FIG. 20H

HindIII A'AGCT_T
Cuts at:    0    903   2351
   Size:       903   1448
HinfI G'AnT_C
Cuts at:    0    19    354   487   516   1002  1041  1597  1790
   Size:       19    335   133   29    486   39    556   193
Cuts at: 1790  1877  2351
   Size:       87    474
   Fragments arranged by size:
            556   486   474   335   193   133   87    39    29    19
HphI GGTGAnnnnnnn_n'
Cuts at:    0    191   1121  2351
   Size:       191   930   1230
   Fragments arranged by size:
           1230   930   191
KpnI G_GTAC'C
Cuts at:    0    1397  2351
   Size:      1397   954
MaeII A'CG_T
Cuts at:    0    112   712   1201  1705  1714  1915  2064  2351
   Size:      112   600   489   504   9     201   149   287
   Fragments arranged by size:
            600   504   489   287   201   149   112   9
MaeIII 'GTnAC_
Cuts at:    0    266   517   1202  1838  2093  2351
   Size:      266   251   685   636   255   258
   Fragments arranged by size:
            685   636   266   258   255   251
MboII GAAGAnnnnnnn_n'
Cuts at:    0    41    188   404   545   900   1094  1175  2082
   Size:      41    147   216   141   355   194   81    907
Cuts at: 2082  2351
   Size:      269
   Fragments arranged by size:
            907   355   269   216   194   147   141   81    41

FIG. 20I

MmeI TCCrACnnnnnnnnnnnnnnnnnnnn_nn'
Cuts at:    0    2248    2351
   Size:    2248    103
MscI TGG'CCA
Cuts at:    0    2043    2351
   Size:    2043    308
MseI T'TA_A
Cuts at:    0    724    2351
   Size:    724    1627
MslI CAynn'nnrTG
Cuts at:    0    204    373    480    1476    1506    2351
   Size:    204    169    107    996    30    845
   Fragments arranged by size:
      996    845    204    169    107    30
MspI C'CG_G
Cuts at:    0    16    237    302    431    653    976    1340    1678
   Size:    16    221    65    129    222    323    364    338
Cuts at:    1678    1974    2351
   Size:    296    377
   Fragments arranged by size:
      377    364    338    323    296    222    221    129    65    16
MspA1I CmG'CkG
Cuts at:    0    413    422    465    565    2351
   Size:    413    9    43    100    1786
   Fragments arranged by size:
      1786    413    100    43    9
NarI GG'CG_CC
Cuts at:    0    807    2351
   Size:    807    1544
NciI CC's_GG
Cuts at:    0    238    303    653    654    976    1679    1974    2351
   Size:    238    65    350    1    322    703    295    377
   Fragments arranged by size:
      703    377    350    322    295    238    65    1
NcoI C'CATG_G
Cuts at:    0    1507    2351
   Size:    1507    844
NheI G'CTAG_C
Cuts at:    0    2182    2351
   Size:    2182    169
NlaIII _CATG'
Cuts at:    0    44    287    858    1441    1511    2351
   Size:    44    243    571    583    70    840
   Fragments arranged by size:
      840    583    571    243    70    44

FIG. 20J

PflMI CCAn_nnn'nTGG
Cuts at:    0   1631   2351
  Size:      1631    720
PleI GAGTCnnnn'n_
Cuts at:    0    27    362    524    996   1591   2351
  Size:      27    335   162    472   595    760
  Fragments arranged by size:
             760    595    472    335    162     27
PmlI CAC'GTG
Cuts at:    0   1916   2351
  Size:      1916    435
Psp5II rG'GwC_Cy
Cuts at:    0   305    845    986   1149   2244   2351
  Size:      305    540   141    163   1095    107
  Fragments arranged by size:
             1095   540    305    163    141    107
Psp1406I AA'CG_TT
Cuts at:    0   112   2351
  Size:      112    2239
PstI C_TGCA'G
Cuts at:    0   697   1493   1772   2351
  Size:      697    796    279    579
  Fragments arranged by size:
             796   697    579    279
PvuII CAG'CTG
Cuts at:    0   413    422    565   2351
  Size:      413     9    143   1786
  Fragments arranged by size:
             1786   413   143     9
RsaI GT'AC
Cuts at:    0   125   501   1053   1122   1395   1665   2351
  Size:      125    376   552    69    273    270    686
  Fragments arranged by size:
             686   552    376   273    270   125    69
SanDI GG'GwC_CC
Cuts at:    0   305   2351
  Size:      305   2046
SapI GCTCTTCn'nnn_
Cuts at:    0    54   2351
  Size:      54    2297
Sau3AI 'GATC_
Cuts at:    0   337    472    895   1024   1516   2351
  Size:      337    135    423    129    492    835
  Fragments arranged by size:
             835   492    423   337    135    129

FIG. 20K

ScaI AGT'ACT
Cuts at:    0    1665    2351
  Size:    1665    686
SfaNI GCATCnnnnn'nnnn
Cuts at:    0    250    251    806    1246    1256    2351
  Size:    250    1    555    440    10    1095
  Fragments arranged by size:
        1095    555    440    250    10    1
SfcI C'TryA_G
Cuts at:    0    693    1489    1768    2351
  Size:    693    796    279    583
  Fragments arranged by size:
        796    693    583    279
SmaI CCC'GGG
Cuts at:    0    654    2351
  Size:    654    1697
SspI AAT'ATT
Cuts at:    0    2076    2351
  Size:    2076    275
StyI C'CwwG_G
Cuts at:    0    71    80    223    452    1507    2351
  Size:    71    9    143    229    1055    844
  Fragments arranged by size:
        1055    844    229    143    71    9
TaqI T'CG_A
Cuts at:    0    116    523    1032    1819    2351
  Size:    116    407    509    787    532
  Fragments arranged by size:
        787    532    509    407    116
TaqII GACCGAnnnnnnnnn_nn'
Cuts at:    0    174    457    2351
  Size:    174    283    1894
  Fragments arranged by size:
        1894    283    174
TauI GCsGC
Cuts at:    0    155    321    1193    2351
  Size:    155    166    872    1158
  Fragments arranged by size:
        1158    872    166    155
TfiI G'AwT_C
Cuts at:    0    487    1041    1790    1877    2351
  Size:    487    554    749    87    474
  Fragments arranged by size:
        749    554    487    474    87

FIG. 20L

ThaI CG'CG
Cuts at:    0    246   1118   2239   2351
   Size:   246   872   1121   112
   Fragments arranged by size:
           1121   872   246   112
TseI GCwGC
Cuts at:    0    97    331   401   423   1856   1909   1929   2351
   Size:    97    234    70    22   1433    53     20    422
   Fragments arranged by size:
           1433   422   234    97    70    53     22     20
Tsp45I 'GTsAC_
Cuts at:    0    266   517   1202   1838   2093   2351
   Size:   266   251   685    636    255    258
   Fragments arranged by size:
           685   636   266   258    255    251
Tsp509I 'AATT_
Cuts at:    0    549   1442   1551   2298   2329   2351
   Size:   549   893   109    747     31     22
   Fragments arranged by size:
           893   747   549   109     31     22
TspRI CAGTGnn'
Cuts at:    0    171   642   742   817   1182   1232   1304   1772
   Size:   171   471   100    75   365     50     72    468
Cuts at:  1772   2036   2351
   Size:   264    315
   Fragments arranged by size:
           471   468   365   315   264   171   100   75   72   50
Tth111I GACn'n_nGTC
Cuts at:    0    88    515   1737   2351
   Size:    88   427   1222    614
   Fragments arranged by size:
           1222   614   427    88
Tth111II CAArCAnnnnnnnnn_nn'
Cuts at:    0    279   604   729   1368   1938   1976   2351
   Size:   279   325   125    639    570     38    375
   Fragments arranged by size:
           639   570   375   325    279    125     38

FIG. 20M

UbaCI w'GTACw
Cuts at:    0   1665   2351
  Size:      1665   686
XcmI CCAnnnn_n'nnnnTGG
Cuts at:    0   450   2351
  Size:      450   1901
XhoI C'TCGA_G
Cuts at:    0   522   2351
  Size:      522   1829
XmnI GAAnn'nnTTC
Cuts at:    0   48   232   2351
  Size:      48   184   2119
  Fragments arranged by size:
             2119   184   48
Enzymes that do cut and were not excluded:

| AceIII | AflIII | AhdI | AlwI | AlwNI | ApoI | AvaI | AvaII |
| BamHI | BanI | BanII | BbsI | BbvI | BccI | Bce83I | BcefI |
| BfaI | BfiI | BglI | BglII | BmgI | BpmI | Bpu10I | BsaI |
| BsaAI | BsaHI | BsaWI | BsaXI | BsbI | BscGI | BseRI | BsiHKAI |
| BsmAI | BsmBI | BsoFI | Bsp24I | Bsp1286I | BspEI | BspGI | BspMI |
| BsrI | BsrBI | BsrDI | BstXI | BstYI | Bsu36I | CviRI | DpnI |
| DraIII | DrdI | DrdII | DsaI | EaeI | EarI | EciI | Eco57I |
| EcoNI | EcoO109I | EcoRI | FauI | FokI | FspI | GdiII | HaeI |
| HaeII | HgaI | Hgi EII | HhaI | Hin4I | HincII | HindIII |
| HinfI | HphI | KpnI | MaeII | MaeIII | MboII | MmeI | MscI |
| MseI | MslI | MspI | MspA1I | NarI | NciI | NcoI | NheI |
| NlaIII | PflMI | PleI | PmlI | Psp5II | Psp1406I | PstI | PvuII |
| RsaI | SanDI | SapI | Sau3AI | ScaI | SfaNI | SfcI | SmaI |
| SspI | StyI | TaqI | TaqII | TauI | TfiI | ThaI | TseI |
| Tsp45I | Tsp509I | TspRI | Tth111I | Tth111II | UbaCI | XcmI | XhoI |
| XmnI | | | | | | | |

Enzymes that do not cut:

| AatII | AccI | AflII | ApaI | ApaBI | ApaLI | AscI | AvrII |
| BaeI | BcgI | BcgI | BclI | BplI | Bpu1102I | BsaBI | BsgI |
| BsiEI | BsmI | BspLU11I | BsrFI | BsrGI | BssHII | BssSI | Bst1107I |
| BstEII | ClaI | DraI | EagI | Eco47III | EcoRV | FseI | HpaI |
| MluI | MunI | NdeI | NgoAIV | NotI | NruI | NsiI | NspI |
| NspV | PacI | Pfl1108I | PinAI | PmeI | PshAI | PvuI | RcaI |
| RleAI | RsrII | SacI | SacII | SalI | SexAI | SfiI | SgfI |
| SgrAI | SnaBI | SpeI | SphI | SrfI | Sse8387I | Sse8647I | StuI |
| SunI | SwaI | VspI | XbaI | | | | |

Enzymes excluded; MinCuts: 1   MaxCuts: 10

| AciI | AluI | BsaJI | BslI | BsmFI | Cac8I | CjeI | CjeI |
| CjePI | CjePI | CviJI | DdeI | EcoRII | HaeIII | MnlI | MwoI |
| NlaIV | Sau96I | ScrFI | | | | | |

FIG. 20N

PRODUCTION OF RECOMBINANT LACTOFERRIN AND LACTOFERRIN POLYPEPTIDES USING CDNA SEQUENCES IN VARIOUS ORGANISMS

RELATED APPLICATIONS

This is a division of application Ser. No. 08/145,681, filed Oct. 28, 1993 which U.S. Pat. No. 5,571,691, is a continuation in part of application Ser. No. 07/967,947, filed Oct. 27, 1992, now abandoned, which in turn is a continuation of application Ser. No. 07/348,270, filed May 5, 1989, now abandoned. This application is also a continuation in part of application Ser. No. 07/873,304 filed Apr. 24, 1992 and now abandoned.

This invention was made with government support under Grant No. HD27965 awarded by the National Institute of Health. The government has certain rights in the invention.

BACKGROUND OF THE INVENTION

1. Field of the Invention

The present invention relates generally to the field of iron-binding glycoproteins. More specifically, the present invention relates to the recombinant production of various lactoferrins.

2. Description of the Prior Art

Lactoferrin (LF) is an iron-binding glycoprotein found in milk and other secretions and body fluids. It is one of a number of iron binding proteins, sometimes referred to as transferring, and is involved in iron binding and delivery in mammals.

Human lactoferrin (hLF) is a member of the transferrin family of iron-binding monomeric glycoproteins. It was originally discovered in milk where it can reach levels of 7 grams/liter in colostrum. LF has since been detected in other external fluids of humans and other mammals. The fluids include tears, saliva and mucosal secretions and also in the secondary granules of polymorphonuclear leukocytes.

Lactoferrin has been implicated as a factor in resistance against enteritis infections in suckled newborn humans. The bacteriocidal/bacteriostatic actions are considered to be due at least in part to the iron binding properties of lactoferrin. Lactoferrin decreases the iron availability to iron-requiring microorganisms and thereby interferes with their growth and reproduction. At least one non-ironbinding bactericidal domain has also been reported for human lactoferrin. Lactoferrin is also considered to have antiviral properties and to have other potential therapeutic applications.

LF is a 78 kilo Dalton (k Da) glycoprotein having a bilobal structure with a high degree of homology between the C and N terminal halves which is evident at both the amino acid and three dimensional structural level. Each of these lobes can reversibly bind one ferric iron with high affinity and with the concomitant binding of bicarbonate. The biological functions proposed for lactoferrin include protection against microbial infection, enhanced intestinal iron absorption in infants, promotion of cell growth, regulation of myelopoiesis and modulation of inflammatory responses.

Human lactoferrin (hLF) has a high affinity for iron and two $Fe^{3+}$ cations can be bound per molecule. The complete HLF protein has been subjected to amino acid sequencing and is reported to have 703 amino acids. There are two glycosylation sites. Metz-Boutigue et al., *Eur. J Biochem.*, 145:659–676 (1984). Anderson et al., *Proc. Nat'l Acad. Sci. USA*, 84:1769–1773 (April 1987).

In other studies, a cloned cDNA probe for amino acids 428 to 703 of the Metz-Boutigue structure of the lactoferrin protein was isolated. The cDNA sequence was in general agreement with the earlier analysis of the amino acid sequence of the protein. Rado et al., *Blood*, 79; 4:989–993, 79; 4:989–993 (October 1987). The probe was reported to encompass approximately 40% of the coding region and the 3' terminus. The CDNA sequence for both porcine, Lydon, J. P., et al., *Biochem. Biophysic. ACTA*, 1132:97–99 (1992); Alexander, L. J., et al., *Animal Genetics*, 23:251–256 (1992) and bovine lactoferrin, Mead, P. E., et al., *Nucleic Acids Research*, 18:7167 (1990); Pierce, A., et al., *Eur. J Biochem.*, 196:177–184 (1991), have been determined.

Polypeptides derived from lactoferrin are also known to be biologically active. A fragment containing a possible iron binding site was reported by Rado, et al. supra. An N-terminal human lactoferrin fragment, including a bactericidal domain of HLF, was isolated from a pepsin digest. Bellamy, W.M., etal., *Biochem. Biophys. ACTA*, 1121:130–136 (1992). Synthetic 23 and 25 amino acid polypeptides were synthesized and found to have activities similar to the fragments derived by pepsin digestion. The synthesis details, yields and purity of the synthetic peptides were not reported. Bellamy et al. do not provide a practical route to large scale production of the polypeptides free of the contaminates resulting form isolation from natural products.

The bactericidal domain from lactoferrin has a broad spectrum of antimicrobial action. Bellamy, W. M. et al., *J App. Bact.* 73, 472–479 (1992). Although Bellamy et al. report that bovine lactoferrin isolated from milk can provide commercial quantities of the bovine polypeptide by pepsin digestion, the materials used in both studies had a minimum purity of only 95%. Bellamy, et al. do not provide constructs for the large scale production of synthetic human or bovine lactoferrin or lactoferrin polypeptides. Neither does Bellamy et al. provide the ability to produce peptides that are not available by enzyme digestion.

Filamentous fungi have been successfully employed as hosts in the industrial production of extracellular glycoproteins. Certain industrial strains are capable of secreting gram quantities of these proteins. In addition, filamentous fungi are able to correctly perform post-translational modifications of eucaryotic proteins and many strains have U.S. Food and Drug Administration approval. Furthermore, large scale fermentation technology and downstream processing experience is available.

Currently, there is no efficient and economical way to produce hLF, other species lactoferrin, or to control production of lactoferrin polypepticdes. Consequently, a long felt need and description in this art would be met by the development of an efficient method for the production of human lactoferrin for nutritional and therapeutic applications and for further investigation into its mechanism of action.

SUMMARY OF THE INVENTION

The invention comprises the verified cDNA sequences for human lactoferrin, and cDNA expression systems for use of various lactoferrin DNA sequences to produce human, bovine, porcine and other lactoferrins for a variety of end uses. The cDNA expression systems of the invention also provide a practical route and method to make lactoferrin polypeptides or fragments having biological activity. The hLF cDNA includes an open reading frame of 213:3 nucleotides coding for a protein of 711 amino acids. These 711 amino acids include 19 amino acids corresponding to a secretion signal peptide sequence followed by 692 amino acids of mature human lactoferrin. The cDNA sequence and deduced amino acid sequence differ from the previously published data of Metz-Boutigue, supra.

In one embodiment, the present invention provides for a recombinant plasmid comprising the cDNA of human or other lactoferrin. The plasmid of the present invention is adapted for expression in a eucaryotic cell and contains the regulatory elements necessary for the expression of the human lactoferrin cDNA in this eucaryotic cell.

In another embodiment, the present invention provides for a transformed cell which includes a heterologous DNA sequence which codes for lactoferrin or a polypeptide related to lactoferrin. The heterologous DNA sequence will preferably be incorporated into a plasmid. Eucaryotic host cells are selected from the group consisting of mammalian cells, immortalized mammalian cells, fungi or yeasts. Preferred cells include filamentous fungi comprising Aspergillus, and yeasts. The plasmid contains a plasmid vector into which a polydeoxyribonucleotide (DNA) segment coding for human or other lactoferrin protein has been inserted.

In yet another embodiment of the present invention, there is provided a process for producing recombinant human or other lactoferrin which comprises culturing a transformant eucaryotic cell, which includes a recombinant plasmid. The plasmid contains a plasmid vector having a polydeoxyribonucleotide coding for the lactoferrin protein. After culturing in a suitable nutrient medium until lactoferrin protein is formed, the lactoferrin protein is isolated.

In still yet another embodiment of the present invention, there is provided a recombinant expression vector. This vector comprises a transcriptional unit comprising an assembly of (1) a genetic element or elements having a lregulatory role in gene expression; (2) cDNA coding for lactoferrin; (3) appropriate transcription and translation initiation and termination sequences; and (4) a genetic element for selection of transformed cells or spores such as Aspergillus spores that have been transformed with the vector.

In still yet another embodiment of the present invention, there is provided a method for producing biologically active recombinant lactoferrin. The method comprises synthesizing sequences containing a selectable marker gene, a promotor, a transcription termination sequence, and a linker sequence; cloning the sequences to form a plasmid; digesting the plasmid with a restriction endonuclease; inserting a cDNA coding for lactoferrin into a restriction site; and transforming eucaryotic cells with the plasmid expressing lactoferrin cDNA.

BRIEF DESCRIPTION OF THE DRAWINGS

So that the manner in which the above recited features, advantages, and objects of the invention, as well as others which will become clear, are obtained and can be understood in detail, more particular descriptions of the invention briefly summarized above may be had by reference to certain embodiments thereof which are illustrated in the appended drawings. These drawings form a part of this specification.

It is to be noted, however, that the appended drawings illustrate preferred embodiments of the invention and therefore not to be considered limiting of its scope. The invention may admit to other equally effective equivalent embodiments.

FIG. 2 is the cDNA sequence (SEQ. ID No. 1) with deduced amino acids (SEQ. ID No. 2) for the human lactoferrin protein and signal peptide sequence.

FIG. 14 is the (A) cDNA sequence (SEQ. ID No. 3) with (B) deduced amino acids (SEQ. ID No. 4) for the bovine lactoferrin protein.

FIG. 15 is the (A) cDNA sequence (SEQ. ID No. 5) with (B) deduced amino acids (SEQ. ID No. 6) for the porcine lactoferrin protein.

FIG. 18 shows restriction enzyme cleavage sites for the huma cDNA sequence.

FIG. 19 shows restriction enzyme cleavage sites for the bovine cDNA sequence.

FIG. 20 shows restriction enzyme cleavage sites for the porcine cDNA sequence.

DETAILED DESCRIPTION OF THE INVENTION DEFINITIONS

Figure 1:
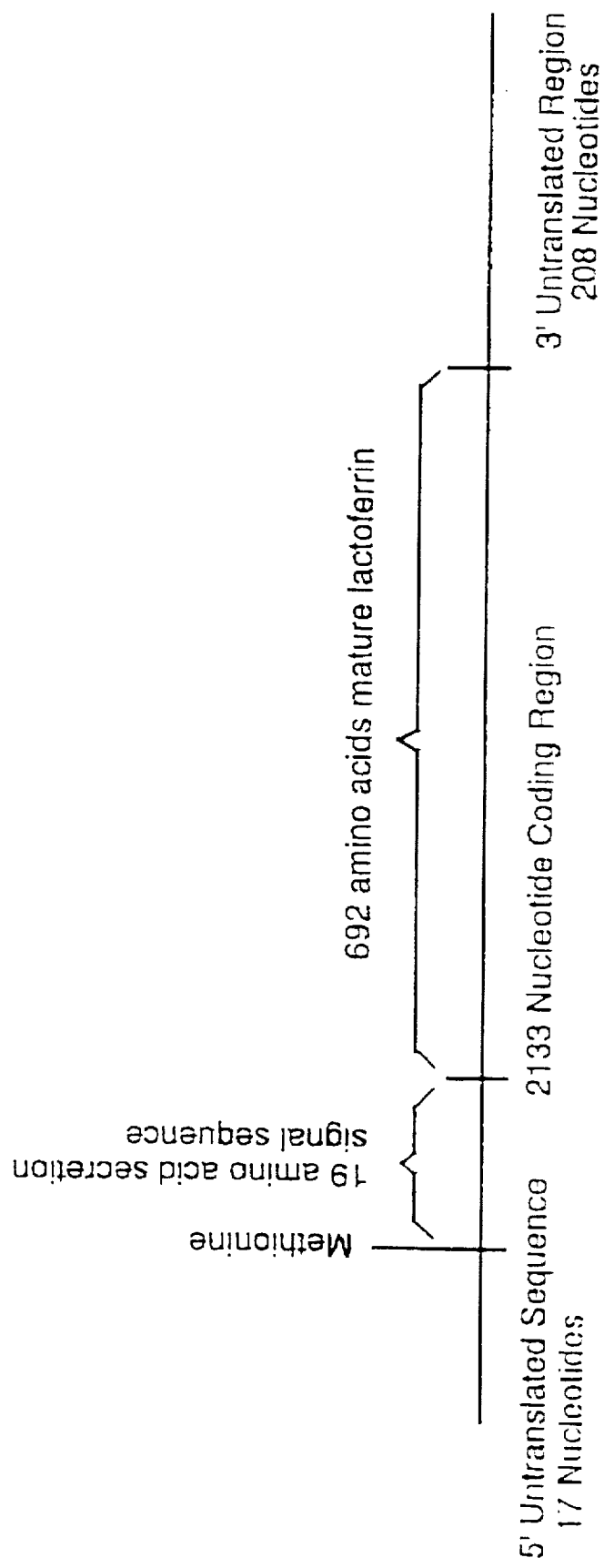
FIG. 1 is a schematic drawing of the hLF cDNA including the locations of the 5' untranslated region, the secretion peptide signal sequence, mature lactoferrin and 3' untranslated region.

For the purposes of the present application, the term "transferrin family" means a family of iron transferring proteins including serum transferrin, ovotransferrin and lactoferrin. These proteins are all structurally related.

For the purposes of the present application, the term "vector(s)" means plasmid, cosmid, phage or other vehicle to allow insertion, propagation and expression of lactoferrin cDNA.

For the purposes of the present application, the term "host(s)" means any cell that will allow lactoferrin expression.

For the purposes of the present application, the term "promotor(s)" means regulatory DNA sequences that controls transcription of the lactoferrin cDNA.

For the purposes of the present application, the term "multiple cloning cassette" means a DNA fragment containing restriction enzyme cleavage sites for a variety of enzymes allowing insertion of a variety of cDNAs.

For the purposes of the present application, the term "transformation" means incorporation permitting expression of heterologous DNA sequences by a cell.

For the purposes of the present application, the term "iron binding capacity" means ability to bind Fe. Fully functional human lactoferrin can bind two atoms of iron per molecule of LF.

For the purposes of the present application, the term "biological activity/biological active" means biological activity of lactoferrin as measured by its ability to bind iron, or kill microorganisms, or retard the growth of microorganisms, or to function as an iron transfer protein.

For the purposes of the present application, the term "substitution analog" referring to a DNA sequence means a DNA sequence in which one or more codons specifying one or more amino acids of lactoferrin or a lactoferrin polypeptide are replaced by alternate codons that specify the same amino acid sequence with a different DNA sequence. Where "substitution analog" refers to a protein or polypeptide it means the substitution of a small number, generally five or less, commonly 3 or 4, and more often 1 or 2 amino acids as are known to occur in allelic variation in human and other mammalian proteins wherein the biological activity of the protein is maintained. For example, hLF isolated from milk has been reported to differ from the hLF of SEQ. ID No. 2 at two amino acid residues.

The confirmation of the cDNA sequence and the deduced amino acid have been proven by multiple confirmation procedures.

These are:
1. Multiple sequence analyses.
2. Comparison of the amino acid sequence deduced from the cDNA with that of hLF generated by conventional amino acid sequencing of hLF isolated from milk. The unique cDNA sequence which encodes the human lactoferrin protein has a variety of applications as known and indicated in the literature.
3. Transcription and translation of hLF protein from the cDNA with positive identification using an anti-hLF antibody.

The cDNA sequence of the present invention can be used to prepare recombinant human lactoferrin, thus making available a source of protein for therapeutic and nutritional applications. The confirmed cDNA of this invention can be used in an appropriate cloning vehicle to replicate the cDNA sequence. Also, the cDNA can be incorporated into a vector system for human lactoferrin expression. Other lactoferrin DNA sequences can be substituted for the human lactoferrin cDNA sequence to provide bovine, porcine, equine or other lactoferrins. Partial cDNA sequences can also be employed to give desired lactoferrin derived polypeptides. The expression systems of the invention can be used to provide lactoferrin derived polypeptides that are not available by enzymatic digestion of naturally occurring lactoferrin. The invention further provides an expression system for producing lactoferrin and lactoferrin related polypeptides in mammalian cell lines, other eucaryotic cells including yeast and fungal cells and procaryotic cells. The invention allows for the production of lactoferrin free of lactoperoxidase, lysozyme, or other proteins that are contaminants of lactoferrin isolated from milk or other natural products. This invention is not limited to any particular uses of the human cDNA sequence or production of lactoferrin of other species from the appropriate DNA sequences.

The recombinant LF being a protein derived by recombinant techniques can be used in a variety of applications. The human gene can be transferred to mammalian systems such as cows and other agriculturally important animals and expressed in milk. The incorporation of a human lactoferrin gene and expression in the milk of animals can combat an iron deficiency typical in piglets. The inclusion of the human lactoferrin gene with expression should improve an animal's disease resistance to bacterial and viral infection. The tissue specific expression of human lactoferrin in mammary glands, for instance, would impart the bacteriocidal and virucidal benefit of the expressed gene to young feeding on the milk and would provide a production means for the secreted protein for therapeutic use.

The gene can be placed in the appropriate cloning vector for the production of LF. The LF produced by recombinant methods can be used in a variety of products including human or animal foods, as therapeutic additives to enhance iron transport and delivery, and for the virucidal and bacteriocidal qualities, as additives for eyedrops, contact lens and other eye care solutions, topical skin care products, eardrops, mouthwashes, chewing gum and toothpaste. The recombinant LF would provide a safe, naturally occurring product which can be topically applied as well as ingested safely. The bactericidal lactoferrin polypeptides are useful as preservatives in the above listed products, and as therapeutic anti-infection agents. The iron binding polypeptides are useful as iron carrier proteins for nutritional and therapeutic uses, and as bacteriostats and bactericides, especially in products of the types listed above. Each protein may also be used as a nutrition supplement and as a source of amino acids.

The full-length cDNA encoding human lactoferrin has been isolated, and the analysis has been completed. The cDNA sequence has been confirmed as human lactoferrin cDNA by comparison of the deduced amino acid sequence with the published amino acid sequence of hLF. The expression of lactoferrin was observed in a eucaryotic expression system from the cDNA and a plasmid vector. The presence of lactoferrin was confirmed by standard Western immunoblot analysis using anti-human lactoferrin antibodies and relative molecular mass measurement.

FIG. 1 is a schematic of the lactoferrin cDNA. The sequence can generally be described as an initial 5' untranslated region, 17 nucleotides in length. The next portion is 57 nucleotides which codes for the 19 amino acid secretion signal peptide starting with methionine. The next sequence of the cDNA codes for the mature human lactoferrin protein of 692 amino acids followed by the 3' untranslated region of 208 nucleotides which ends the cDNA. The complete sequence is 2,358 nucleotides in length. The hLF protein contains glycosylation sites. The hLF protein with secretion signal sequence has an expected molecular mass of 78,403 daltons and the mature hLF is 76,386 daltons without added carbohydrate from glycosylation.

FIG. 2 is the cDNA sequence (SEQ ID No. 1) with the deduced amino acids (SEQ ID No. 2) for the secretion signal peptide and the mature human lactoferrin protein. The numbers on FIG. 2 correspond to the nucleotides starting at the 5' end. There are binding sites for two iron atoms with four amino acids participating in the binding of each iron. The amino acids at positions Asp80, Tyr112, Tyr209, and His273 are required for coordination with one iron, and amino acids at positions Asp415, Tyr455, Tyr548, and His617 bind the other. There are two glycosylation sites at positions Asn157 and Asn498. The numbers refer to the deduced amino acid sequence. There are 25 amino acids per line of protein sequence (starting at nucleotide 18).

The nucleotide sequence analysis was performed on cDNA isolated from a human prostate cDNA library. The prostate cDNA library yielded a 2,140 bp cDNA which contained the complete 5' end including the untranslated portion and the signal sequence. The 3' end including the three amino acids at the carboxy terminal and the untranslated region were obtained as a 208 bp cDNA from both a monocyte cDNA library and human prostate cDNA library.

The data in FIG. 2 displays the full-length cDNA sequence of this invention. The complete sequence including the 5' untranslated region and signal peptide have not been reported. Further, the previously reported amino acid sequence varies from the deduced amino acid sequence for hLF of this invention. The following TABLE 1 is a summary of the differences of the amino acid sequence of the present invention and those reported by Metz-Boutigue et al., *Eur. J. Biochem.*, vol. 145, pp. 659–76 (1984). For the purpose of this table, the numbering of the amino acids will be initiated with methionine at the start of the signal peptide sequence as amino acid #1.

TABLE 1

COMPARISON OF AMINO ACID SEQUENCES
HUMAN LACTOFERRIN

| Amino Acid Deduced from cDNA of hLF | Change | Metz-Boutigue Sequence |
|---|---|---|
| #30 Thr | Substitution | Ala |
| #48 Arg | Substitution | Lys |
| #141 Arg | Insertion | NONE |
| #170 Ala | Insertion | NONE |
| #204 Ser | Substitution | Leu |
| #206 Gln | Substitution | Lys |
| #209 Tyr | Substitution | Lys |
| #386 Glu | Substitution | Gln |
| #392 Ser | Substitution | Trp |
| #410 Asp | Substitution | Asn |
| #411–424 | Deletion | 13 Amino acids in protein sequence not in deduced amino acid sequence from cDNA |
| #532 Gln | Substitution | Glu |
| #695 Lys | Substitution | Arg |

Figure 3:
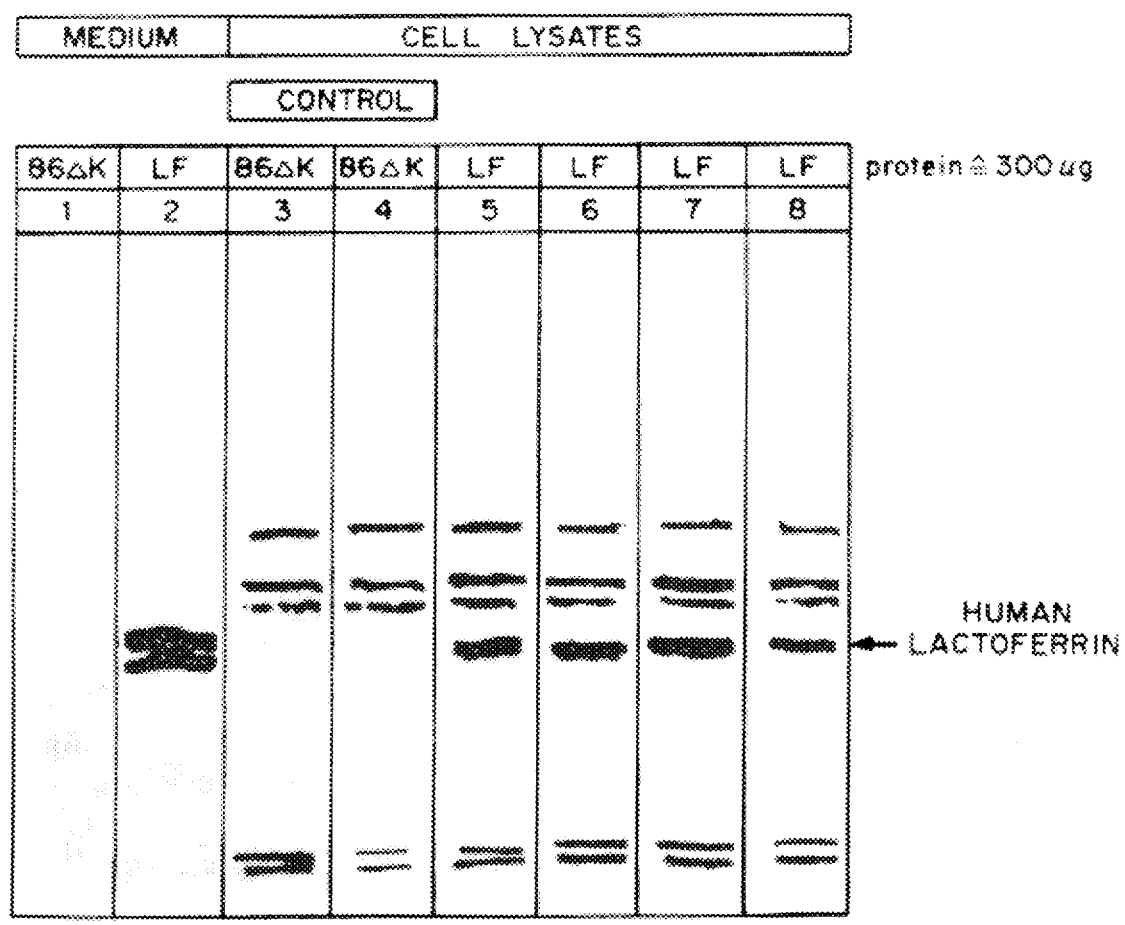
FIG. 3 is a schematic representation of an autoradiograph of recombinant human lactoferrin protein expressed from the complete cDNA.

FIG. 3 is the expression of human lactoferrin protein from the complete hLF cDNA. In addition to using the entire cDNA sequence and deduced amino acid sequence, a polypeptide of less than the entire protein can be of value. For instance, the region between amino acids 74–275 contains an iron binding domain which may be used without the rest of the protein for biologically available iron or the bacteriostatic qualities.

The cDNA sequence has been confirmed to encode lactoferrin. The hLF cDNA was shown to encode lactoferrin by expression of the cDNA in a eucaryotic expression system and detection of the expressed lactoferrin protein by Western immunoblot analysis using specific lactoferrin antibodies.

Recombinant production of lactoferrin protein has been described below in its preferred embodiments. However, it is also produced in a number of other sources such as fungal sources such as *Saccharomyces cerevisiae, Kluyveromyces lactis*, or *Pichia pastorsis*, or insect cells such as SF9, or bacterial cells such as *Escherichia coli*, or *Bacillus subtilis*.

In one embodiment of the present invention, biologically active recombinant lactoferrin protein is produced. This method comprises synthesizing sequences containing a selectable marker gene, a promotor, a transcription termination sequence and a linker sequence.

Subsequently, the sequences are cloned to form a plasmid and the plasmid is digested with a restriction endonuclease. A cDNA coding for lactoferrin is inserted into a restriction site and eucaryotic cells are then transformed with the plasmid expressing the lactoferrin cDNA.

The selectable marker gene useful in the method of the present invention may be any that permits isolation of cells transformed with a lactoferrin cDNA plasmid. Preferably, the selectable marker gene is selected from pyr4, pyrG, argB, trpC and andS.

The promotor useful in the present invention may be any that allows regulation of the transcription of the lactoferrin cDNA. Preferably, the promotor is selected from the group of alcohol dehydrogenase, argB, α-amylase and glucoamylase genes.

The transcription termination sequence useful in the present method may be any that allows stabilization of the lactoferrin mRNA. Preferably, the transcription termination sequence is derived from the α-amylase, glucoamylase, alcohol dehydrogenase or benA genes.

The linker sequence useful in the present method may be any that contains a translation initiation codon, a secretory signal and a restriction enzyme cleavage site. Preferably, the linker element is derived from the α-amylase or glucoamylase genes.

The cells, preferably eucaryotic cells, useful in the present invention are any that allow for integration of a vector, preferably a plasmid comprising the lactoferrin cDNA and expression of the lactoferrin cDNA. Preferably, the eucaryotic cells are fungal cells or insect cells. Insect cells such as SF9 are useful in the method of the present invention. More preferably, the fungal cells are yeast cells or Aspergillus. Most preferably, the eucaryotic cells useful in the present invention are Aspergillus strains, such as *A. oryzae, A. niger, A. nidulans* and *A. awamori*.

The invention also comprises partial sequences of the cDNA of SEQ ID No. 1, 3 and 5 and substitution analogs thereof which code for biologically active polypeptides having homology with a portion of lactoferrin, especially those that are not available from enzyme digests of natural lactoferrins, the method of making polypeptides by use and expression of partial cDNA sequences, and the polypeptide products produced by the methods of this invention. The desired partial sequences can be produced by restriction enzyme cleavage, as for example at the cleavage sites indicated in FIGS. 18, 19 and 20. the partial sequences may also be synthesized or obtained by a combination of cleavage, ligation and synthesis, or by other methods known to those skilled in the art.

Recombinant production of lactoferrin protein and polypeptides has been described in its preferred embodiment. However, it is also produced in a number of other sources such as fungal sources such as *Saccharomyces cerevisiae, Kluyveromyces lactis*, or *Pichia pastoris* or insect cells such as SF9, and lactoferrin polypeptides may also be produced in bacterial cells such as *Escherichia coli*, or *Bacillus subtilis*.

The following examples are given for the purposes of illustrating various embodiments of the present invention and are not meant to be limitations of the present invention in any form.

EXAMPLE 1

HUMAN LACTOFERRIN cDNA

The complete 2,358 bp hLF cDNA was ligated to the eucaryotic expression vector, p91023(B) at the EcoRi site downstream from the adenovirus major late promoter. This plasmid vector was provided by Genetics Institute (Cambridge, Mass.) and has been described in previous publications (Wong et al., Science 288:810–815 (1985)). The hLF cDNA expression vector was transferred into COSM-6 monkey kidney cells using standard tissue culture transfection conditions (Wigler et al., Cell, 16:777–785 (1979)). These COS cells do not normally express lactoferrin. Forty-eight hours after transfection, the cells were harvested and crude cell extracts were prepared. Positive identification of the human lactoferrin was made by standard Western immunoblot analysis of the proteins expressed in the cell extracts, as well as those secreted into the cell growth medium using a commercially available antibody directed against human lactoferrin (Sigma). Proteins which bound to the anti-lactoferrin antibody were detected using radio-iodine labelled Protein A which reacts with the antibody. The immunoblots were autoradiographed to identify the human lactoferrin protein. FIG. 3 is an autoradiographic film showing the human lactoferrin expressed in four cell extracts prepared from tissue culture cells which were transfected with the lactoferrin cDNA expression vector (lanes 5 to 8). Lanes 5 to 8 show that the transfected cells all contain human lactoferrin (marked with an arrow) which is immunoreactive with the anti-lactoferrin antibody and is the same molecular weight as human lactoferrin (Mr=78,403 daltons). The control cells which were not transfected with the cDNA did not contain lactoferrin (lanes 3 and 4). Analysis of the growth medium showed that human lactoferrin was also secreted into the medium from transfected cells (lane 2) but not from control cells (lane 1).

The cDNA encodes a recombinant human lactoferrin protein which is similar to human lactoferrin protein isolated from milk as determined by molecular size comparisons and immunoreactivity with anti-human lactoferrin. Furthermore, the secretion signal peptide sequence is functional since the human lactoferrin is secreted into the growth medium of tissue culture cells which express the cDNA.

Figure 4:
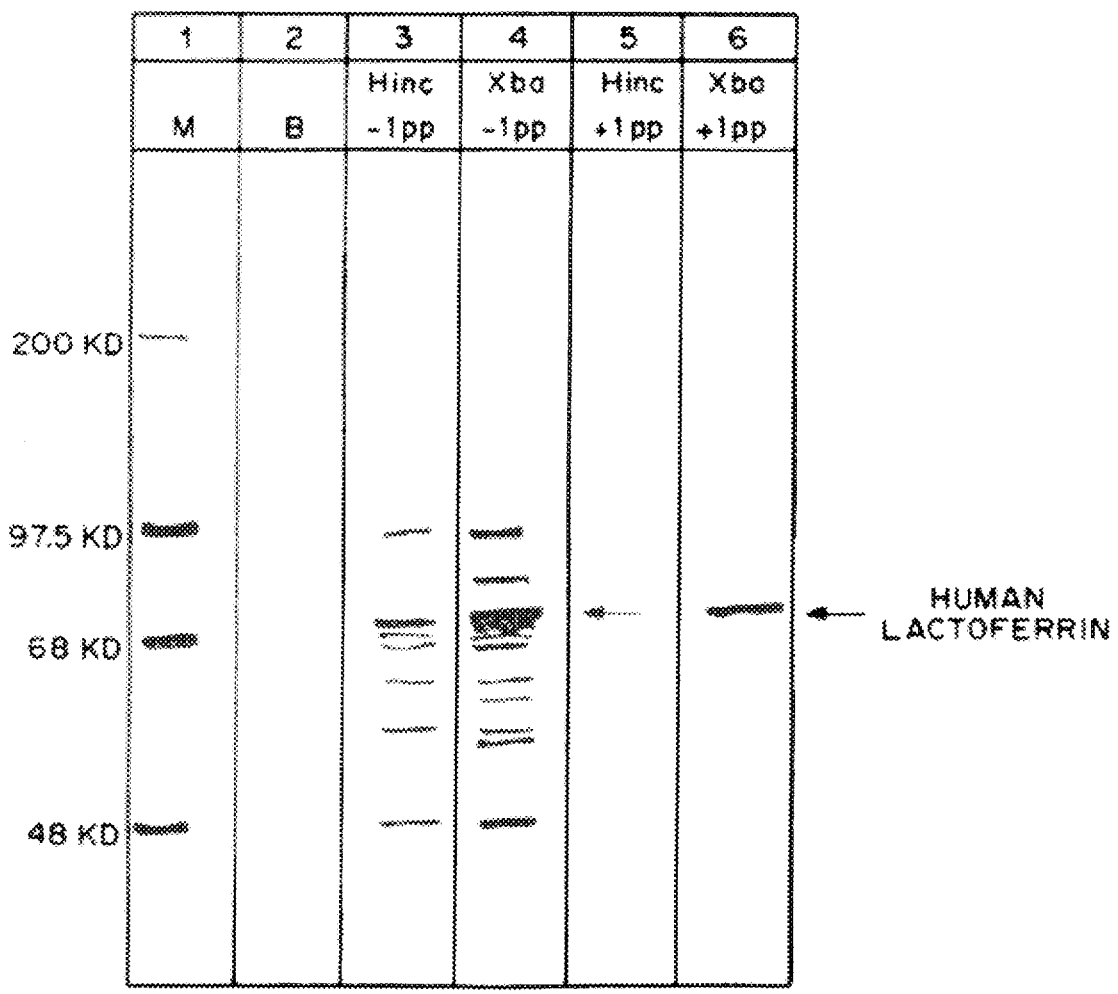
FIG. 4 is a schematic representation of an autoradiograph of the results of in vitro translation of a 2,140 bp human lactoferrin sequence and hLF protein in reticulocyte lysates.

FIG. 4 is a schematic representation of the human lactoferrin protein precipitated after in vitro transcription and translation of the human lactoferrin cDNA. The 2140 bp cDNA was from the human prostate cDNA library and included the 5' untranslated region and the rest of the base pairs correlative to the cDNA sequence of FIG. 2 omitting the last 208 bp at the 3' terminus. The 2140 bp cDNA was ligated to the EcoRI site of the plasmid vector pGEM$_4$ (commercially available from Promega Biotech., Madison, Wis. 53711–5305) downstream from the SP$_6$ promoter. The plasmid construct was linearized at the 3' end of the hLF cDNA using the restriction enzyme Hinc II or Xba I. The linear DNA template was then transcribed in vitro using purified SP$_6$ RNA polymerase in the presence of ribonucleotides as described in the manufacturers protocol (Promega Corporation 1988/1989 Catalogue and Applications Guide).

The resultant mRNA was translated using 100 ng mRNA template and micrococcal nuclease treated rabbit reticulocyte lysate (as described by Promega) in the presence of 75 uCi $^{35}$S methionine (800 ci/mmol, Amersham). In vitro synthesized lactoferrin was immunoprecipitated by incubating 100 ul aliquots of translation reaction with 10 ug of rabbit anti-human lactoferrin IgG (Sigma Chemical Company, St. Louis, Mo. 63178) for 2 hours at 4° C. in 50 mM Tris, pH7.5/0.15M NaCl/0.05% Tween-20 (1 P buffer). The reaction volume was 200 ul. Immunoreactive lactoferrin was precipitated after incubation for 1 hour with 5 Oug of Protein A sepharose (Pharmacia, Upsalla, Sweden). Immunoprecipitation was carried out by centrifugation for 5 minutes at 10,000 g and the precipitate was washed 5 times with 4 volumes of IP buffer. Total translation products and immunoprecipitates were then subjected to electrophoresis in denaturing 7.5% polyacrylamide gels. After fixing in 50% methanol, the gels were incubated in En$^3$Hance (NEN, DuPont, Wilmington, Del. 19801) for 1 hour and washed with distilled H$_2$O. The gel was then dried under vacuum and exposed to Kodak X-OMAT XAR film at –70° C.

Lane 1 shows $^{14}$C protein molecular weight markers used to estimate the size of the translated proteins. Lane 2 is a negative control which shows that no $^{35}$S labelled proteins are translated in this system when no mRNA is added to the translation mix. Lanes 3 and 4 show the total translation products obtained when lactoferrin mRNA is added after preparation from two separate DNA templates. The major protein band (marked with an arrow) is human lactoferrin. This is the only band detected when the translation products are immunoprecipitated with anti-human lactoferrin before applying the protein to the gel (lane 6). The measurement of molecular mass by SDS-PAGE does not correspond to exact molecular weight due to secondary protein structure. However, the values are shifted in a correlative manner in comparison to the control. Analysis of the size of the translated lactoferrin is shown in FIG. 4. The protein migrated at the expected molecular mass of human lactoferrin (about 78 Kd). The major bands in lanes 3 and 4 which migrate higher than the 68 Kd marker band in the control lane correspond to expected molecular mass of hLF protein on SDS-PAGE.

EXAMPLE 2

FUNGAL STRAINS AND TRANSFORMATION

The pyrG mutant strain used in these studies was derived from A. oryzae (AO7 11488). The pyrG gene from A. oryzae was mutated with 4-nitroquinoline-1-oxide. The Aspergillus transformation was carried out by a modification of the procedure of Osmani, et al., J. Cell. Biol. 104:1495–1504 (1987). Conidia (1×10$^6$/ml) were inoculated into 50 ml of YG medium (0.5% yeast extract 2% glucose) containing 5 mM uracil and 10 mM uridine. Growth was at 32° C. for 14–16 hours until a germ tube was visible. The germinated conidia were harvested by centrifugation and resuspended in 40 ml of lytic mix containing 0.4M ammonium sulphate, 50 mM potassium citrate (pH 6.0), 0.5% yeast extract, 0.12 g novozyme, 0.1 g Driselase, 100 µl β-glucuronidase, 0.5% sucrose and 10 mM MgSO$_4$. Protoplasting was for 2–3 hours at 32° C. and 150 rpm. Following protoplasting, filtration using sterile miracloth was necessary to remove any undigested mycelia. The protoplasts were harvested by centrifugation and washed twice with 10 ml of 0.4M ammonium sulphate, 1% sucrose and 50 mM potassium citrate (pH 6.0) at 4° C., resuspended in 1 ml of 0.6M KCl; 50 mM CaCl; 10 mM Tris-HCl (pH 7.5) and placed on ice. The transformation was performed immediately following the protoplast preparation. Aliquots (100 µl) of the protoplast were added to 3 µg of DNA and 50 µl of 40% polyethylene glycol (PEG) 6000, 50 mM CaCl$_2$, 0.6M KCl and 10 mM Tris-HCl, (pH 7.5). The samples were incubated on ice for fifteen minutes after which an additional 1 ml of the PEG solution was added and incubation at room temperature was continued for thirty minutes. Aliquots of this mixture were plated in 3 mls of 0.7% minimal media, supplemented with 0.4% ammonium sulphate onto plates containing the same but solidified with 2% agar. All subsequent growth was at 32° C.

EXAMPLE 3

PLASMID CONSTRUCTION

Figure 5:
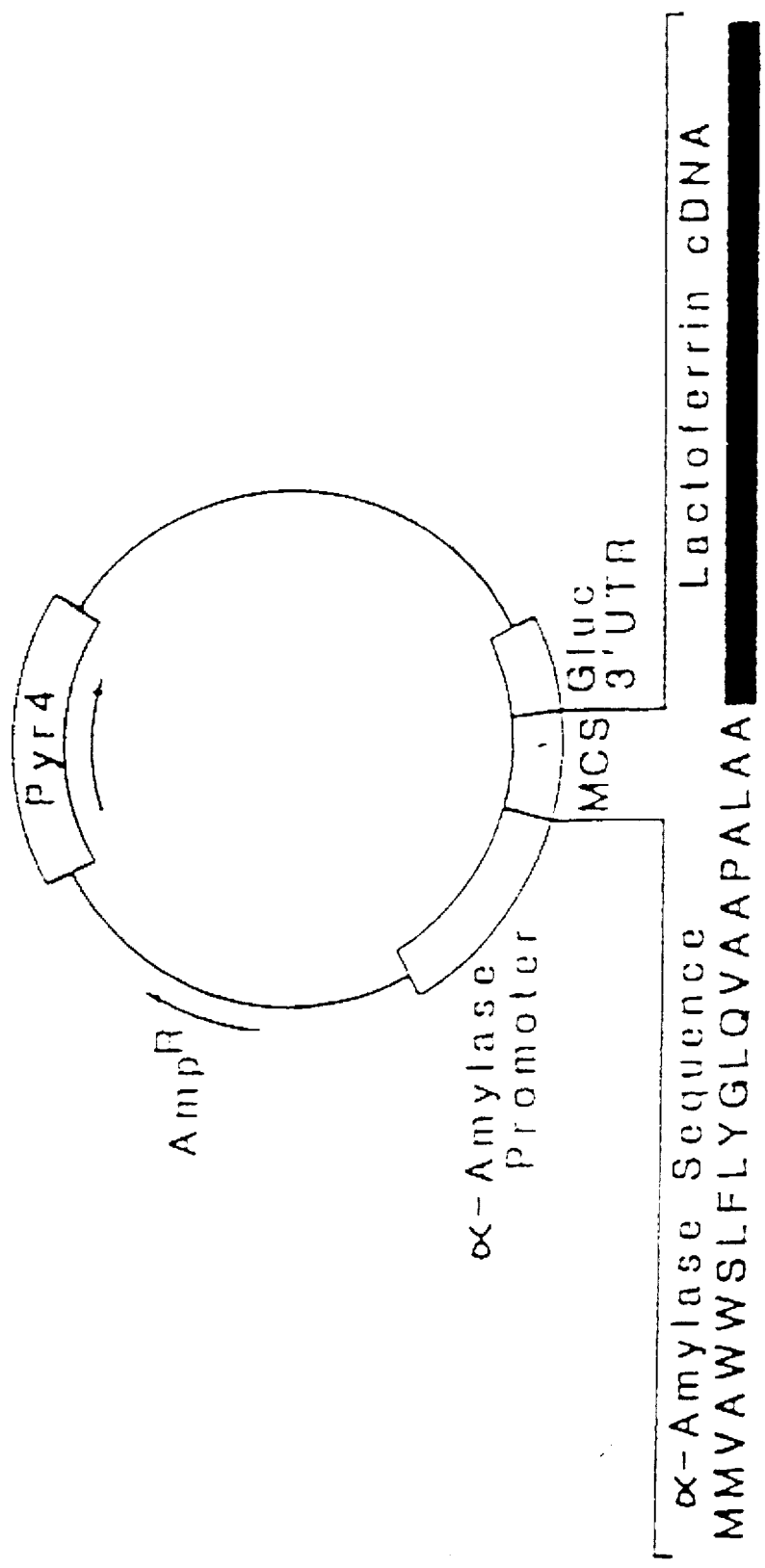
FIG. 5 depicts a schematic representation of the Aspergillus oryzae expression plasmid, pAhlfg.

A schematic representation of the expression plasmid is shown in FIG. 5. The complete cDNA encoding human LF was repaired using the Klenow fragment of DNA polymerase I and subcloned into Acc I digested and repaired pGEM4 to generate pGEMhLFc. In order to remove the LF signal sequence and generate a 5' end in frame with the α-amylase sequences, a 252 base pair lactoferrin fragment (nt 69–321) containing Hind II/Acc I ends was obtained by polymerase chain reaction (PCR) amplification of pGEMhLFc plasmid DNA. The oligo primers used were as follows: the 5' end oligonucleotide as shown in SEQ. ID. No. 7:

(CTGGGTCGACGTAGGAGAAGGAGTGTTCAGTGGTGC)

and the 3' end oligonucleotide as shown in SEQ. ID. No. 8:

(GCCGTAGACTTCCGCCGCTACAGG).

This PCR fragment was digested with Hind II and Acc I and was subcloned into Hind II/Acc I digested pGEMhLFc generating pGEMhLF. A 681 base pair α-amylase fragment with Asp718/Pvu II ends encoding the promotor, signal sequence and the alanine residue from the start of the mature α-amylase II gene, was obtained by PCR amplification of A. oryzae genomic DNA. The oligo primers were as follows: the 5' end oligonucleotide as shown in SEQ. ID. No. 9:

(GAGGTACCGAATTCATGGTGTTTTGATCATTTTAAATTTTTATAT)

and the 3' end oligonucleotide as shown in SEQ. ID. No. 10:

(AGCAGCTGCAGCCAAAGCAGGTGCCGCGACCTGAAGGCCGTAC AG).

The amplified DNA was digested with Asp718 and Pvu II and subcloned into Asp718/Hind II digested pGEMhLF. The resulting plasmid (pGEMAhLF) was digested with EcoR I and the resulting 2.8 kb α-amylase-lactoferrin fragment was subcloned into a unique EcoR I site in pAL3 according to the method of generating pAhLF*. Synthetic oligonucleotides were used to provide the last five carboxy terminal codons of lactoferrin (nt 2138–2153) missing in pAhLF* and also to provide the first 180 bp of 3' untranslated sequences from the A. niger glucoamylase gene. The resulting plasmid (pAhLFG) was used to transform the A. oryzae pyrG mutant strain.

With reference to FIG. 5, Aspergillus oryzae expression plasmid, pAhLFG contains 681 bp of 5'-flanking sequence of the A. oryzae AMY II gene which includes the signal sequence and first codon of mature α-amylase. The cDNA coding for mature human lactoferrin is subcloned in frame downstream from these sequences allowing recombinant protein production by the addition of starch to the growth medium. The Aspergillus niger glucoamylase 3' untranslated region provides the transcription terminator and polyadenylation signals. The plasmid also contains the Neurospora crassa pyr4 selectable marker and an ampicillin resistance gene.

The plasmid construct (pAhLFG) used for expression of human LF contains a 681 bp fragment that encodes the promotor and secretory signal peptide of the A. oryzae α-amylase II gene (AMY II). The signal sequence also contains the codon for alanine from the start of the α-amylase mature protein generating the signal sequence cleavage site (Leu Ala) recognizable by an endogenase α-amylase peptidase. A human lactoferrin cDNA fragment encoding the mature protein was subcloned in frame immediately downstream from the AMY II sequences, placing it under the control of this highly efficient starch inducible promoter. In order to stabilize the transcribed human LF mRNA, a 180 bp fragment encoding the 3' untranslated region of the glucoamylase gene from Aspergillus niger was ligated into a unique BamH I site in the multiple cloning cassette, immediately downstream of the human LF cDNA providing the transcription terminator and polyadenylation signals. The plasmid also contains the Neurospora crassa pyr4 selectable marker which complements a pyrG auxotrophic mutation of A. oryzae and allows for selection of spores that have been transformed with the plasmid by growth in the absence of uridine.

EXAMPLE 4

GENOMIC DNA MANIPULATION

A. oryzae DNA was isolated from 200 mg of lyophilized mycelia as described by Rasmussen, et al., J. Biol. Chem., 265:13767–13775 (1990). The DNA was digested with EcoR I, size fractionated on a 0.8% agarose gel and transferred to nitrocellulose. Prehybridization and hybridization of the nitrocellulose filter for Southern analysis were performed in 6×SSC, 0. 1% SDS and 0.5% dried milk at 65° C. for 16 hours. Hybridization solution contained 1 ×10hu 7 cpm $^{32}$P-labelled lactoferrin cDNA probe (2.1 Kb). The filter was washed in 2×SSC, 0.5% SDS at room temperature for 30 minutes followed by two washes in 0.5×SSC, 0.5% SDS at 68° C. for 30 minutes. The filter was dried, exposed at −70° C. for two hours and developed by autoradiography.

Figure 6:
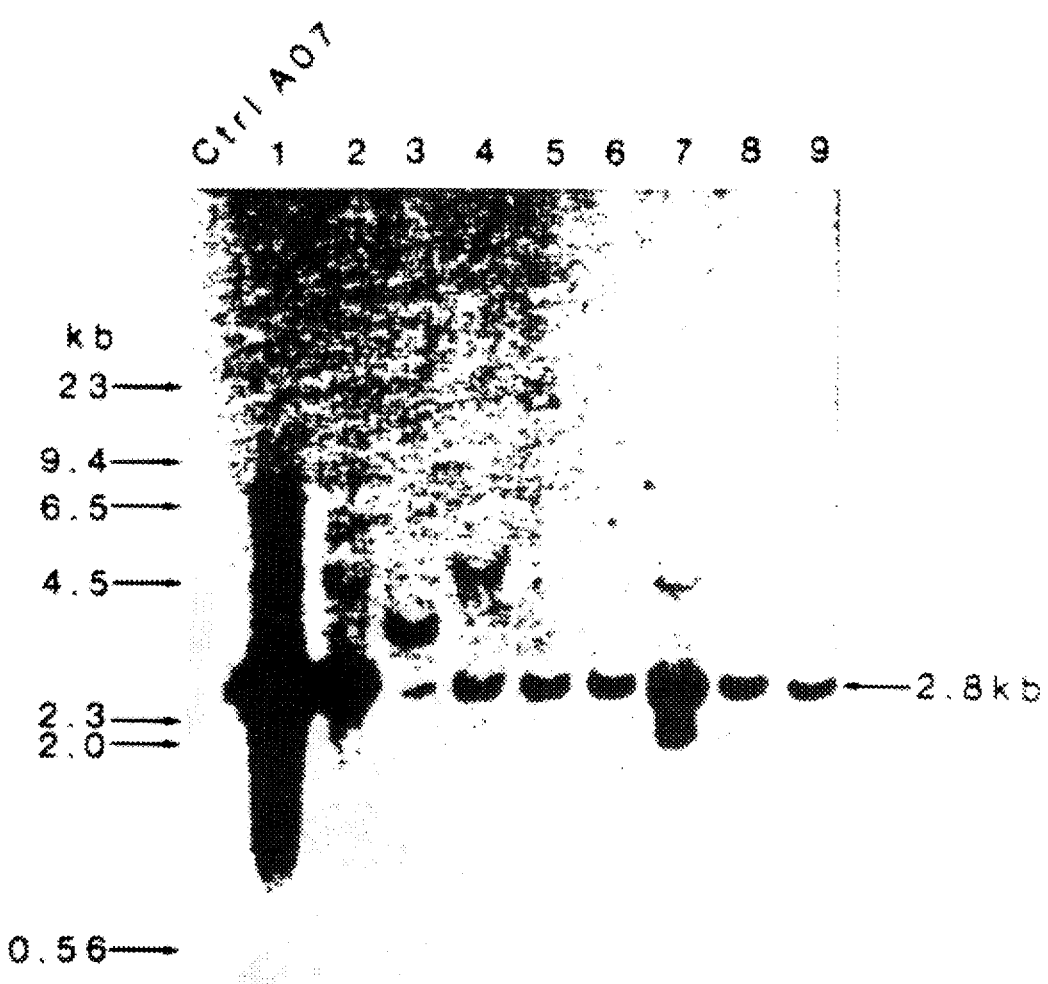
FIG. 6 shows a southern blot analysis of transformed Aspergillus oryzae strains.

With reference to FIG. 6, Southern blot analysis was performed on transformed Aspergillus oryzae strains. Genomic DNA from individual transformants and control AO7 were hybridized with a radiolabelled hLF cDNA probe (2.1 kb). The arrow points to a radiolabelled fragment (2.8 kb) generated upon EcoR I digestion of the expression plasmid which is present in all the transformants (#1–9) but is absent in control untransformed AO7. Molecular weights of bacteriophage lambda Hind III fragments are indicated at the left.

EXAMPLE 6

NORTHERN ANALYSIS

RNA was isolated from lyophilized mycelia (200 mg) using commercially available RNazol B (Biotecx Laboratories, INC, Houston.Tex.) according to the manufacturers instructions. Total RNA (20 μg) was electrophoresed in a 0.8% agarose gel containing 2.2M formaldehyde. The RNA was transferred to nitrocellulose and hybridized with either a 2.1 kb lactoferrin cDNA or a 1.8 kb genomic α-amylase fragment corresponding to the coding region of the α-amylase II gene. The probes were $^{32}$P-labelled by nick translation (specific activity 2×10$^8$ cpm/ug). Hybridization was carried out 2×SSC, .05% dried milk at 65° C. over an ice with 2×10$^6$ cpm probe/ml.

Washes were identical to those employed in the Southern analysis. The filters were dried, exposed at −70° C. for two hours and developed by autoradiography. RNA dot blots were performed using nitrocellulose membrane and the manifold dot blot system. Hybridization and washing conditions were as described above for Southern analysis. Radioactivity was quantitated using the betagon blot analyzer.

With reference to FIG. 7, RNA analysis of transformant versus control AO7 was performed. In Panel A, Northern analysis of RNA (20 μg) from control AO7 and transformant #1 were hybridized with radiolabelled human LF cDNA. Human LF mRNA (2.3 kb) was detected in the transformant #1 but not in the control untransformed AO7. The positions of the 28 S and 18 S rRNA bands are indicated on the left. In Panel B, Dot blots of RNA (5 and 10 fg) from control AO7 versus transformant #1 using a radiolabelled α-amylase genomic DNA probe. In Panel C, Dot blots of RNA (5 and 10 μg) from control AO7 and transformant #1 using radiolabelled human LF cDNA probe as illustrated.

Northern analysis was performed to determine if lactoferrin mRNA was transcribed correctly and efficiently in *A. oryzae* under the regulatory control elements of the expression plasmid. Spores ($1 \times 10^6$/ml) from transformant #1 and from control untransformed spores were inoculated into fungal medium containing 1.5% glucose as carbon source and grown at 30° C. for 48 hours in small shake flask cultures. The cultures were washed and reinoculated into fungal medium containing 3% starch to induce transcription of the human LF mRNA. After 24 hours, the cells were harvested and RNA was isolated. Total RNA (20 μg) was size fractionated on a 1.0% agarose gel containing 2.2M formaldehyde and blotted on nitrocellulose.

Figure 7A:
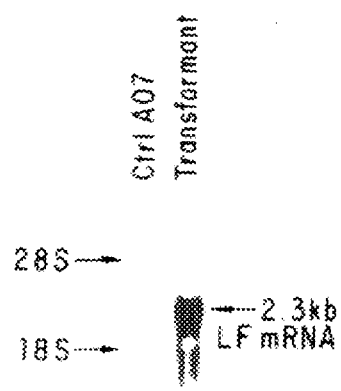
FIG. 7 depicts an RNA analysis of transformant versus control AO7.
Figure 7B:
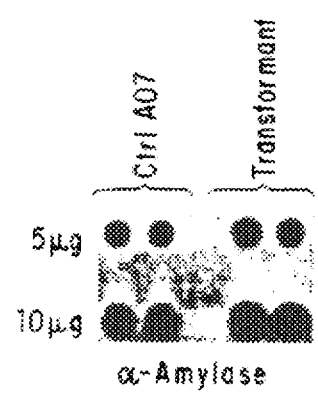
Figure 7C:
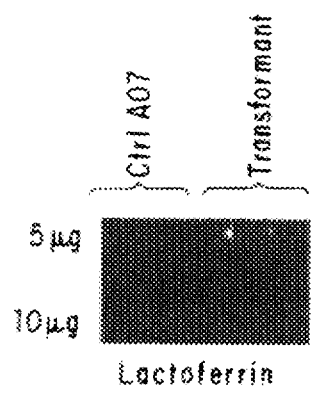

Human lactoferrin mRNA was detected using $^{32}$p labelled human LF cDNA (2.0 kb) probe. Hybridization with human LF radiolabelled cDNA probe detected a specific radiolabelled band at the correct size for lactoferrin mRNA (2.3 kb) in the transformant but not in the control untransformed strain (FIG. 7A). Quantitation of mRNA levels by dot assay showed comparable levels of expression of endogenous OL-amylase rRNA between control AO7 and transformant #1 (FIG. 7B). In addition, similar levels of expression of α-amylase and human LF mRNA were seen in transformant #1 (FIG. 7B and 7C).

EXAMPLE 6

PURIFICATION OF RECOMBINANT HUMAN LF

LF was purified from the growth medium using CM Sephadex C50 essentially as described by Stowell, et al., *Biochem J.*, 276:349–59 (1991). The column was pre-equilibrated with 500 ml of 0.025M Tris HCl, pH 7.50 1M NaCl. The pH of the culture medium was adjusted to pH 7.4 before applying to the pre-equilibrated column. The column was washed with 500 ml of equilibration buffer and followed by a linear salt gradient from 0.1 to 1.1M NaCl. Fractions (7 ml total) were assayed for lactoferrin content and purity using SDS/PAGE and silver staining. Fractions containing LF were dialyzed against 0.025M Tris HCl, pH 7.5/0.1M NaCl and lyophilized.

EXAMPLE 7

QUANTITATION OF HUMAN LF

Recombinant lactoferrin was quantitated using an ELISA assay essentially as described by Vilja et al., *J. Immunol. Methods*, 76:73–83 (1985). A sensitivity of 5 ng of lactoferrin was obtained using the non-competitive Avidin-biotin assay. Human LF isolated from breast milk (Sigma) was used as standard. Biotinylated human lactoferrin IgG was obtained from Jackson Immunoresearch laboratories, West Grove, Pa.

EXAMPLE 8

N-TERMINAL SEQUENCING

Five μg of purified recombinant human LF was resolved on an SDS-polyacrylamide gel and transferred to Problott, a polyvinylidene difluride-type membrane, following manufacturers instructions (Applied Biosystems). Human LF was detected with Comassie Brilliant Blue staining and destained. This human LF band was excised, washed thoroughly with distilled $H_2O$ and air-dried. The N-terminal amino acid sequence of the first ten amino acids of human LF was determined by the automated Edman degradation procedure using an applied Biosystems Pulsed-liquid phase sequencer (Model 477A).

Figure 8A:
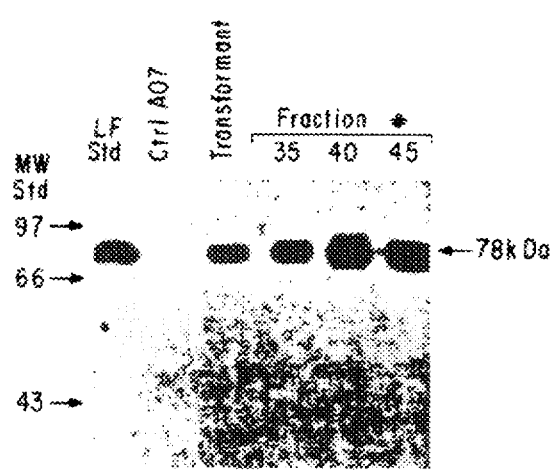
FIG. 8 shows the silver stained SDS-acrylimide gel analysis of recombinant LF secretion and purification.
Figure 8B:
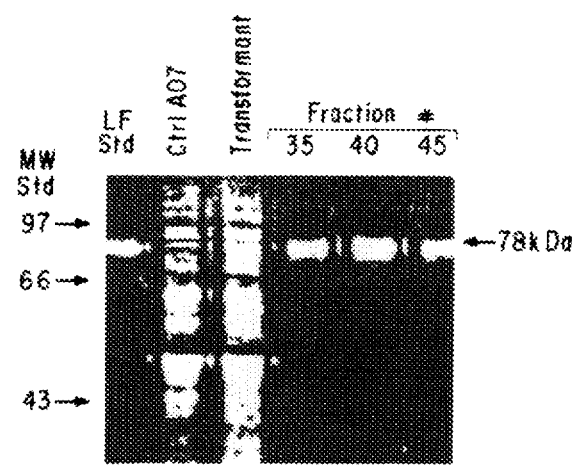

With reference to FIG. 8, panel A illustrates a Silver stained SDS-polyacrylamide gel analysis of recombinant human LF secretion and purification. Lane 1 contains breast milk human LF standard (500 ng). Lanes 2 and 3 contain samples of the growth medium (40 μg) from induced control AO7 and transformant #1 respectively. Lanes 4–8 contain 100 μl aliquots of eluted fractions (#25, 30, 35, 40, and 45 respectively) collected from the CM-sephadex purification of recombinant LF from the growth medium of transformant #1. The position of the molecular weight markers (BioRad Richmond, Calif.) are indicated on the left. Sizes are given in kilo Daltons. Panel B illustrates a Western immunoblot analysis of duplicate samples as described in panel A using a specific polyclonal antibody directed against human LF with detection with $^{125}$I-protein A. Panel C illustrates #6 N-terminal amino acid sequence of recombinant human LF. Recombinant human LF was sequenced from the N-terminus through 10 residues and is identical to breast milk human LF with the exception of the additional alanine generated in our construction to provide the α-amylase signal sequence cleavage site.

EXAMPLE 9

DEGLYCOSYLATION

Deglycosylation was performed using N-glycosidase F (Boehringer Mannheim). *A. oryzae* growth medium containing 0.5 μg lactoferrin was denatured for 3 minutes at 100° C. in the presence of 0.01% SDS. Standard LF from human milk was treated similarly. The samples were subsequently placed on ice for five minutes. N-glycosidase F reactions were conducted in 0.4M sodium phosphate, (pH 6.8); 0.08% Triton; 0.1% β-mercaptoethanol and 1 unit of enzyme and incubated at 37° C. for sixteen hours. PAGE and Western analysis was performed using an IgG specifically directed against human lactoferrin to detect an increase in mobility of digested samples.

Figure 9A:
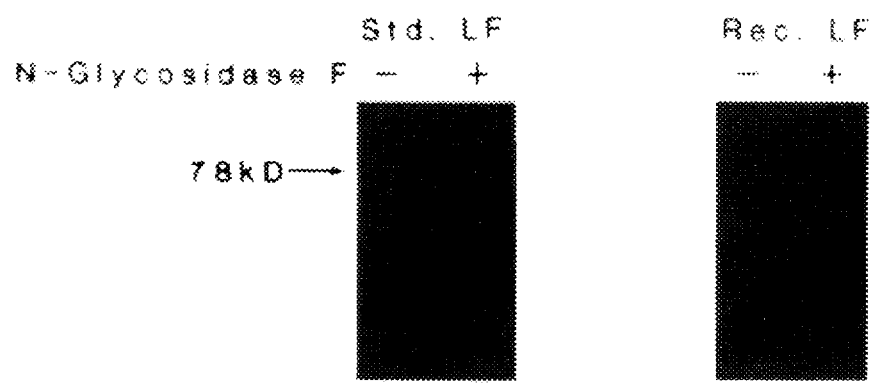
FIG. 9 illustrates the characterization of recombinant human LF.
Figure 9B:
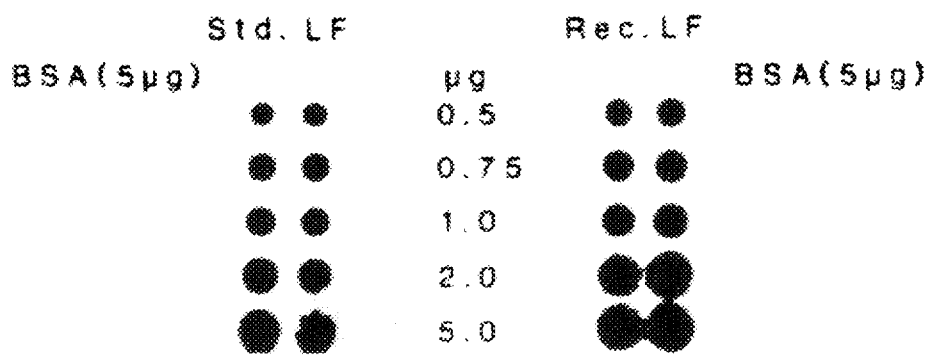

With reference to FIG. 9, recombinant human LF was characterized. Panel A illustrates the deglycosylation of lactoferrin. Western analysis of glycosylated and deglycosylated lactoferrin using a specific polyclonal antibody was directed against human lactoferrin with detection with $^{125}$I-protein A. The first panel contains authentic breast milk human LF (500 ng) untreated (−) and treated (+) with N-glycosidase F. The second panel contains purified recombinant human LF (500 ng) untreated (−) and treated (+) with N-glycosidase F. The size of glycosylated human LF is indicated with the arrow. Panel B illustrates a functional analysis of recombinant lactoferrin with regard to iron-binding capacity. Panel A and B show the $^{59}$Fe filter binding assay of duplicate samples of authentic breast milk human LF and purified recombinant human LF, respectively, at the concentrations indicated. The first lane in both panels contain BSA (5 μg) as a negative control.

Lactoferrin contains two N-acetyllactamine type glycans attached through N-glycosidic linkages. To determine if recombinant lactoferrin was glycosylated correctly, the protein was treated with N-glycosidase F, resolved on SDS-polyacrylamide electrophoresis, transferred to nitrocellulose and probed using a specific IgG directed against human lactoferrin (FIG. 11A). N-glycosidase F hydrolyses at the glycosylamine linkage generating a carbohydrate free peptide of smaller molecular weight. Comparison of recombinant LF with purified LF from human milk, illustrates that both proteins co-migrate upon digestion with N-glycosidase F suggesting that the recombinant protein has a glycosylation pattern similar to native LF.

Lactoferrin has a bilobal structure with each lobe having the capacity to bind tightly, but reversibly, one $Fe^{3+}$ ion. The iron-binding properties of lactoferrin are crucial for its functional roles. To test if recombinant human LF expressed and secreted in *A. oryzae* has an iron binding capacity similar to authentic lactoferrin, an $^{59}Fe$ micro filter binding assay was developed. Purified human lactoferrin isolated from the growth medium of transformant #1 was dialyzed against 0.1M citric acid (pH 2.0) to generate apo-human LF. Native lactoferrin from human milk was treated similarly. Excess $^{59}Fe$ (0.2 mCi) was added to these samples in an equal volume of 1M bicarbonate, followed by incubation at 37° C. for 30 minutes. Samples were applied to nitrocellulose membrane and washed several times with bicarbonate. The filter was visualized by autoradiography and Fe-binding was quantitated using a betagon blot analyzer. As illustrated in FIG. 11B, both recombinant and native LF showed a similar level of iron binding at all concentrations tested. The results demonstrate that recombinant human LF is indistinguishable from native human LF in its capacity to bind iron.

With reference to FIG. 2, the complete cDNA sequence for human lactoferrin protein is depicted. The cDNA coding for lactoferrin is used to create plasmids and transform eucaryotic cells and to produce the lactoferrin protein.

Strains of Aspergillus used in the present invention are auxotrophic mutants that contain a defective pry4 gene that results in an inability to synthesis orotidine 5' phosphate (OMP) decarboxylase. The enzyme is required for uridine synthesis. The strain cannot grow on media lacking uridine. The plasmid contains a selectable marker, i.e., a sequence that encodes the gene for OMP decarboxylase. Uptake of the plasmid by the Aspergillus can therefore be selected for by growth on media lacking uridine. The Aspergillus is transformed by the plasmid such that it can grow on the uridine deficient media.

EXAMPLE 10

EXPRESSION OF THE 3' IRON-BINDING DOMAIN OF HUMAN LACTOFERRIN—*E. COLI*

The 3' iron-binding domain of human lactoferrin (hLF) was expressed in *Escherichia coli* using the bacterial expression plasmid, PT7-7 as described by Tabor, S. and Richardson, C., *Proc. Natl. Acad. Sci. U.S.A.*, 82:1074–1078 (1985). pGEMhLFc, containing the cDNA for the complete hLF cDNA (Ward, P. P., et al. *Gene.* 122:219–223 (1992)), was digested with Sma I and Hind III to release a 1.5 kb fragment encoding the 3' iron-binding domain of hLF. This 1.5 kb Sma I/Hind III fragment was subcloned in-frame into Sma I/Hind II digested PT7-7, under the control of the strong inducible T7 promoter, generating PT7-7hLF3' having the ATCC Accession Number ATCC 97681.

PT7-7hLF3' was transformed into a protease deficient strain of *E. coli* which had previously been transformed with pGP1-2 plasmid which contained the T7 polymerase under the control of the XpL promoter as described by Conneely, O. M., et al. *In: Hormone Action and Molecular Endocrinology.* 5-48 –5-50 (1989)). The PT7-7 plasmid contained an ampicillin resistance gene while the pGP1-2 plasmid contained a kanamycin resistant gene allowing dual antibiotic resistance selection for transformants containing both plasmids. Transformants obtained were cultured overnight in LB broth containing ampicillin (50 µg/ml) and kanamycin (50 µg/ml) at 30° C./250 rpm. Overnight cultures were subcultured into LB (500 ml) containing ampicillin and kanamycin and grown at 30° C./250 rpm until an $O.D._{600}nm$ of 0.5–0.6 was obtained. At 30° C. the λ repressor bound to the λpL promoter, thus blocking T7 polymerase production. Induction of the recombinant protein was achieved by raising the temperature to 42° C. for one hour to inactivate the λ repressor thus allowing T7 polymerase production. The temperature was lowered to 30° C. for a further two hours, turning off λpL directed transcription and allowing the production of the recombinant protein as the T7 polymerase bound to the T7 promoter to specifically induce expression of the recombinant lactoferrin 3' iron-binding domain.

Western Immunoblot analysis was performed to determine if the 3' iron binding domain was expressed in the bacterial cells under the control of the T7 promoter and to monitor its purification. The cells were harvested at 5000 g and resuspended in 15 ml of PBS (pH 7.4). Total cellular extracts were prepared by sonication for 1 minute on ice. The sonicate was centrifuged at 13,000 g for 40 minutes at 4° C. The supernatant was removed and the pellet was resuspended in 50 ml of denaturation buffer (5M urea, 2% triton, 5 mM EDTA, 0.01% Tween 20, 50 mM TrisCl, pH 7.5) and centrifuged at 48,000 g for one hour. The supernatant containing the soluble fraction was recovered. Protein concentration was determined using the Bradford reagent according to manufacturers instructions (BioRad, Richmond, Calif.). Protein samples (40 µg) were resolved by SDS-PAGE and transferred to a nitrocellulose filter electrophoretically using the Western Immunoblot procedure. The filter was blocked with Tris-buffered saline (TBS, 0.05M Tris/0.15M NaCl, pH 7.5) containing 2% dried milk, and then incubated for 2 hours in the same with the addition of a specific polyclonal IgG (1 µg/ml) directed against hLF (Sigma, St. Louis, Mo.). The filter was washed (5×10 min) in TBS/0.05% Nonidet P-40 followed by incubation with 5 µCi of $^{125}I$ protein A in TBS/2% dried milk. The filter was washed (5×10 min) in TBS/0.05% Nonidet P-40, dried and exposed overnight in Kodak XAR5 film at −70° C. The film was developed by autoradiography.

Figure 10:
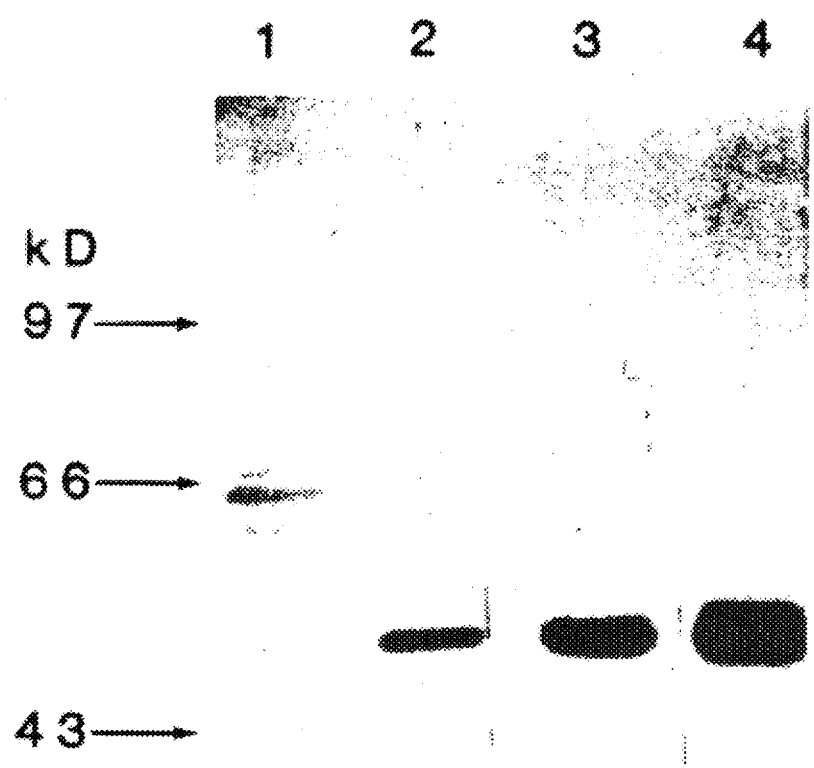
FIG. 10 is a western immunoblot of cellular extracts of transformed E.coli cells expressing the C terminal fragment of LF.

The results of the Western analysis are shown in FIG. 10. An immunoreactive band at the expected size (50 kDa) for the hLF 3' iron-binding domain was evident in the cellular extract from induced cells and was absent in control uninduced cells (FIG. 10, lanes 1 and 2). The hLF 3' iron-binding domain associates with the cellular homogenate insoluble fraction (FIG. 10, lane 3) and hence required a further solubilization step in a denaturation buffer to prepare the hLF in a soluble form (FIG. 10, lane 4).

Figure 11:
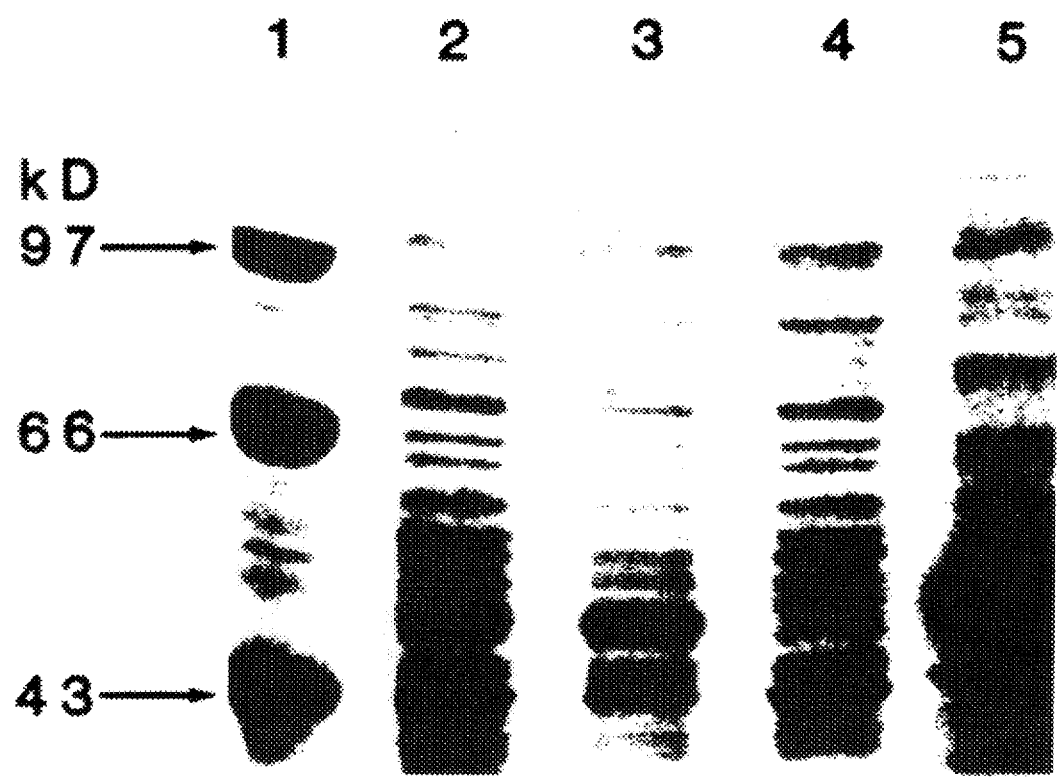
FIG. 11 shows the coomassie-stained SDS-PAGE analysis of extracts of transformed E. coli cells expressing the C terminal fragment of LF.

Analysis of a coomassie-stained SDS-PAGE gel also showed the presence of a 50 kDa protein in the cellular extract from induced cultures which was absent in control uninduced cultures (FIG. 11, lanes 2 and 3). The recombinant protein was expressed at levels up to 10 mg/l and represented approximately 5% of the total cellular protein. The hLF 3' iron-binding domain did not associate with the soluble homogenate fraction (FIG. 11, lane 4) and hence required a further solubilization step in a denaturation buffer to prepare the hLF in a soluble form (FIG. 11, lane 5). Purification and solubilization of the recombinant hLF 3' iron-binding domain resulted in a 50% yield of recoverable protein and represented the major protein band in this fraction.

In summary, we have successfully produced recombinant hLF 3' iron-binding domain in *E. coli* under the control of the strong inducible T7 promoter. The recombinant protein was expressed and purified in a soluble form from the cellular extracts at levels up to 5 mg/l.

EXAMPLE 12

EXPRESSION AND PURIFICATION OF AN N-TERMINAL LACTOFERRIN FRAGMENT (AA 1-52) IN ESCHERICHIA COLI.

An N-terminal human lactoferrin fragment (AA 1-52), encoding the bactericidal domain of hLF, reported by Bellamy et al., supra, was expressed and purified from *E. coli*. The bovine lactoferrin fragment also reported by Bellamy, et al. is produced by the same method illustrated here for the human fragment. This was achieved using the glutathione S-transferase (GST) Gene Fusion System (Pharmacia, Piscataway, N.J.) where the lactoferrin fragment was expressed as a fusion protein with glutathione S-transferase [Smith, D. S., et al., *Gene*, 67:31–40 (1988)] and a protease cleavage site allowing production of the bactoricidal domain by cleavage from GST.

A 156 bp human lactoferrin fragment encoding AA 1-52, containing Sma I/BamnH I ends was obtained by polymerase chain reaction (PCR) amplification of pGEMhLFc plasmid DNA [Ward, P. P., et al., *Biotechnology*, 10:784–789 (1992)]. The oligonucleotide primers used were as follows:

5' end oligonucleotide as shown in SEQ. ID. NO. 11
CTGCCCGGGCGTAGGAGAAGGAGTGTT

3' end oligonucleotide as shown in SEQ. ID. No. 12
CATGGATCCTGTTTTACGCAATGGCCTGGATACA This PCR fragment was digested with Sma I and BamH I and repaired using the Klenow Fragment of DNA polymerase I. This fragment was subcloned into BamH I repaired pGEX-3X generating pGEX-3XLFN-1. This fused the lactoferrin cDNA fragment in frame, downstream from the glutathione S-transferase gene and under the control of the strong, inducible tac promoter. All PCR amplified products and construction junctions were sequenced using the commercially available Sequenase version 2.0 kit (United states Biochemical Corp, Cleveland, Ohio).

pGEX-3XLFN-1 was transformed into the bacterial strain, JM109. Transformants obtained were cultured overnight in LB (50 ml) containing ampicillin (50 g/ml) at 37° C./250 rpm. Overnight cultures were subcultured into LB (500 ml) containing ampicillin (50 g/ml) and grown at 37° C./250 rpm until an OD$_{600}$nm of 0.6–0.8 was obtained. Isopropyl-D-thiogalactopyranoside (IPTG) was added to the culture medium at a concentration of 1 mM to turn on the tac promoter resulting in expression of the glutathione S-transferase/LFN-1 fusion protein. Growth under these conditions continued for 4 hours after which the cells were harvested at 5,000 g and resuspended in 5 ml of MTPBS (150 mM NaCl, 16 mM Na$_2$HPO$_4$, 4 mM NaH$_2$PO$_4$, 1% Triton X-100, pH 7.3). Total cellular extracts were prepared by 3×1 minute freeze/thaw cycles followed by mild sonication for 2×1 minute. The sonicate was centrifuged at 13,000 g for minutes and the supernatant obtained was applied to a glutathione sepharose 4B column following manufacturer's instructions (Pharmacia, Piscataway, N.J.). The glutathione S-transferase/LFN-1 fusion protein was eluted from the column using 10 ml of elution buffer (10 mM glutathione, 50 mM Tris pH 8.0). Fractions of 1.5 ml were collected and dialyzed overnight against 50 mM Tris, 15% glycerol pH 8.0.

Figure 12A:
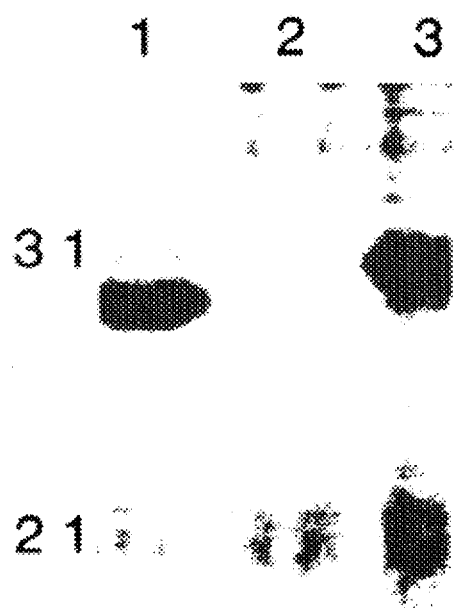
FIG. 12 shows the expression and purification of the glutathione S-transferase/LFN-1 fusion protein.
Figure 12B:
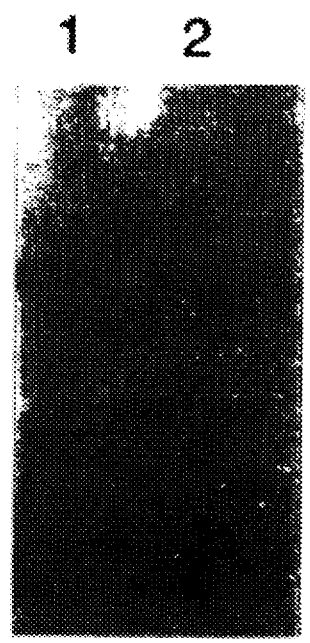

Samples from the solubilized extracts and the purification fractions were analyzed by SDS/PAGE followed by silver-staining. The results of this analysis are shown in FIG. 12. A band at the expected size (32 kDa) for the glutathione S-transferase/LFN-1 fusion protein was detected in the solubilized protein extracts from induced JM109 cultures transformed with pGEX-3X/LFN-1 and was absent in uninduced cultures (FIG. 12A, lanes 2 and 3). This band migrates at a higher mobility than control induced JM109 cultures transformed with pGEX-3X alone (FIG. 12A, lane 1). The fusion protein was successfully purified to homogeneity over a glutathione sepharose 4B column (FIG. 12B, lanes 1 and 2). Protein concentration determination using the Bradford reagent (BioRad, Richmond, Calif.) showed that the glutathione S-transferase/LFNI fusion protein was purified at levels up to 5 mg/l. The GST fusion protein has a protease cleavage site for the protease Kex II between GST and the 52 amino acid protein.

In summary, a human lactoferrin fragment, encoding a bactericidal domain of this protein, has been successfully expressed as a fusion protein with glutathione S-transferase an *E. coli* expression system. This fusion protein was purified to homogeneity at levels up to 5 mg/l. The bactericidal protein is obtained by cleavage with the protease Kex II to cleave the GST portion from the bactericidal domain.

EXAMPLE 13

EXPRESSION OF BOVINE AND PORCINE LACTOFERRIN IN *ASPERGILLUS ORYZAE*.

A universal *A. oryzae* expression vector is constructed to allow in frame subcloning of any cloned cDNA of interest. This vector, pAG, is similar to the vector pAhLFG(+1) utilized for the expression of human lactoferrin in *A. oryzae* above. A 680 bp α-amylase fragment encoding the promoter, signal sequence and the alanine residue from the start of the mature -amylase II gene, is obtained by polymerase chain reaction (PCR) amplification of pAhLFG(+1). The oligonucleotide primers are as follows:

5' end oligonucleotide, SEQ. ID. NO. 13

5 ' CGGAATTCATGGTGTTTTGATCATTTT

3' end oligonucleotide, SEQ. ID. NO. 14

5' TGGAATTCGATCGCGGATCCGCAATG-CATGCAGCCAAAGCAGGTGCCG CGAC

The 5' end oligonucleotide encodes an EcoR I site and the 3' end oligonucleotide contains an Nsi I site, flanked by a BamH I site. This amplified DNA is digested with EcoR I and BamH I and subcloned into EcoR I/BamH I digested pAhLFG(+1) generating pAG. All PCR amplified products and construction junctions are sequenced using the commercially available Sequenase version 2.0 kit (United States Biochemical Corp., Cleveland, Ohio).

Figure 13:
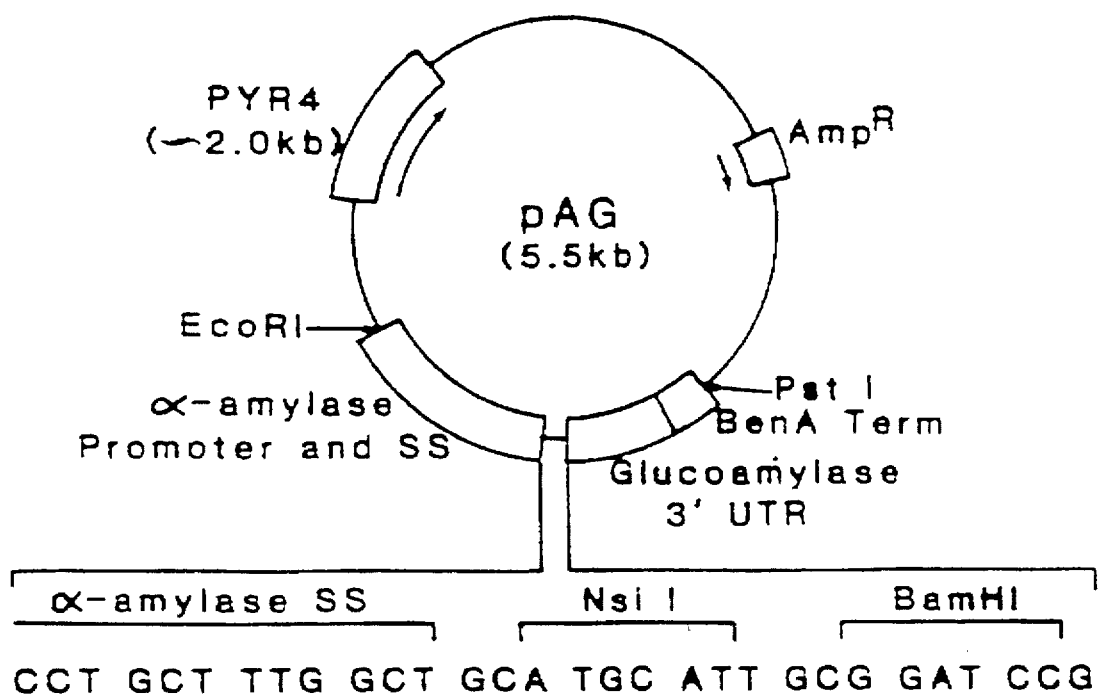
FIG. 13 Schematic representation of the A. Oryzae universal expression plasmid, pAG.

A schematic representation of this expression plasmid is outlined in FIG. 13. Restriction enzyme digestion of this expression plasmid with Nsi I, followed by repair using DNA polymerase I allows subcloning of any cDNA of interest in frame with the α-amylase signal sequence and alanine residue from the start of the mature α-amylase II gene. 5' and 3' oligonucleotide primers are designed to contain Acc 1 ends, and used to obtain the full length cDNA encoding for mature porcine and bovine lactoferrin using polymerase chain reaction (PCR) amplification of their known DNA sequence. The PCR fragment thus obtained is digested with Acc I and repaired using the Klenow fragment of DNA polymerase I for in frame subcloning into Nsi I blunt-ended pAG. The plasmids are then be transformed into the pyrG-strain of *A. oryzae* to obtain expression and secretion of these cDNAs as previously described for human lactoferrin.

EXAMPLE 14

EXPRESSION OF HUMAN LACTOFERRIN IN *SACCHAROMYCES CEREVISIAE*

The complete human lactoferrin (hLF) cDNA was expressed in *Saccharomyces cerevisiae* using the yeast expression plasmid, YEP [McDonnell, D. P. et al., *J. Steroid Biochem, Molec. Biol.*, 39:291–297 (1991)]. A 2.2 kb fragment encoding the complete hLF cDNA SEQ. ID No. 1 was generated using the polymerase chain reaction. This fragment contained and XhoI restriction enzyme site at its 5' end and an Asp718 restriction enzyme site at its 3' end. The 2.2 kb fragment was subcloned, in frame, into XhoI/Asp718 digested YEP to yield, YEPLFc.

Transcription of the hLF cDNA was under the control of the copper responsive yeast metallothionein promoter (CUPI). hLF was produced as a ubiquitin fusion protein. The fusion protein is short lived in the yeast cells and is processed to produce unfused protein upon folding.

YEPLFc was transformed into a protease deficient strain of S. cerevisiae, by standard techniques [Ito, H., et al., *J. Bacteriol.*, 153:163–186 (1983).] This strain cannot grow unless the growth medium is supplemented with adenine, uracil and tryptophan. The YEP plasmid contains a tryptophan selectable marker, thus, transformants were selected by tryptophan auxotrophy.

Transformants obtained were cultured overnight in selective medium containing 2% glucose, 0.1% casamino acids, 0.67% yeast nitrogen base, 0.001% adenine and 0.002% uracil at 30° C./200 rpm. When the cells reached an $OD_{600}$nm of 1.0, $1 \times 10^6$ cells were inoculated into 10 ml of the selective medium and 100 µm $CuSO_4$ added. The cells were grown for 24 hours at 30° C./200 rpm. The purpose of adding the $CuSO_4$ was to induce expression of the hLF cDNA from the copper inducible CUP1 promoter.

Western immunoblot analysis was performed to determine if hLF was expressed in the yeast cells under the control of the CUP1 promoter. The cells were harvested by centrifugation at 5000×g for 5 min. and resuspended in 1 ml of Z buffer (120mM $Na_2HPO_4 7H_2O$, 40 mM $NaH_2PO_4 H_2O$, 10 mM KCl, 1 mM $MgSO_4 7H_2O$, 0.27% 2-mercaptoehanol, pH 7.0). Total cellular extracts were prepared by glass bead homogenization. This procedure involved mixing the yeast cells with an equal volume of glass beads (0.5 mm, B. Braun Instruments) and vortexing for 5×1 min. The homogenate was centrifuged at 13,000 g for 10 min. and the supernatant removed. The protein concentration was determined using the Bradford reagent in accordance with the manufacturer's instructions (BioRad, Richmond, Calif.). Protein samples (50 µg) were resolved by SDS-PAGE and electrophoretically transferred, overnight, to a nitrocellulose filter using the western immunoblot procedure. The filter was blocked with tris-buffered saline (TBS=0.05M Tris/0. 15M NaCl, pH 7.5) containing 1% dried milk and then incubated overnight, in the same, with the addition of a specific rabbit polyclonal antibody (1 µg/ml) directed against hLF (Signa, St. Louis, Mo.). The filter was washed in TBS/0. 1% Tween 20 (5×5 min.) followed by incubation with horseradish peroxidase (Amersham, UK) for 1 hour. The filter was washed in TBS/0.3% Tween 20 (3×5 min.) and then TBS/0.1% Tween 20 (3×5 min.). The filter was then treated with luminol and enhancer (Amersham, UK) for 1 min., dried and exposed for 1 min. to X-ray film. The film was developed by autoradiography.

These data demonstrate successful production of recombinant hLF in *S. cerevisiae* under the control of the copper inducible (CUPI) promoter.

Figure 16:
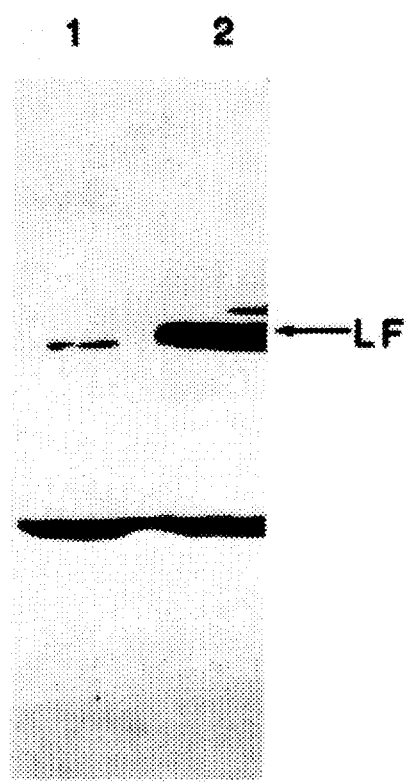
FIG. 16 is a Western blot showing hLF expression in Saccharomycles cerevisiae.

The results of the western analysis are shown in FIG. 16. An immunoreactive band at the expected size (78 kDa) for hLF was evident in the cellular extract from transformed *S. cerevisiae* cells. FIG. 16, lane 1.

EXAMPLE 15

EXPRESSION OF hLF IN *ASPERGILLIS NIDULANS*.

Construction of the *Aspergillis Nidulans* Expression Plasmid.

Figure 17:
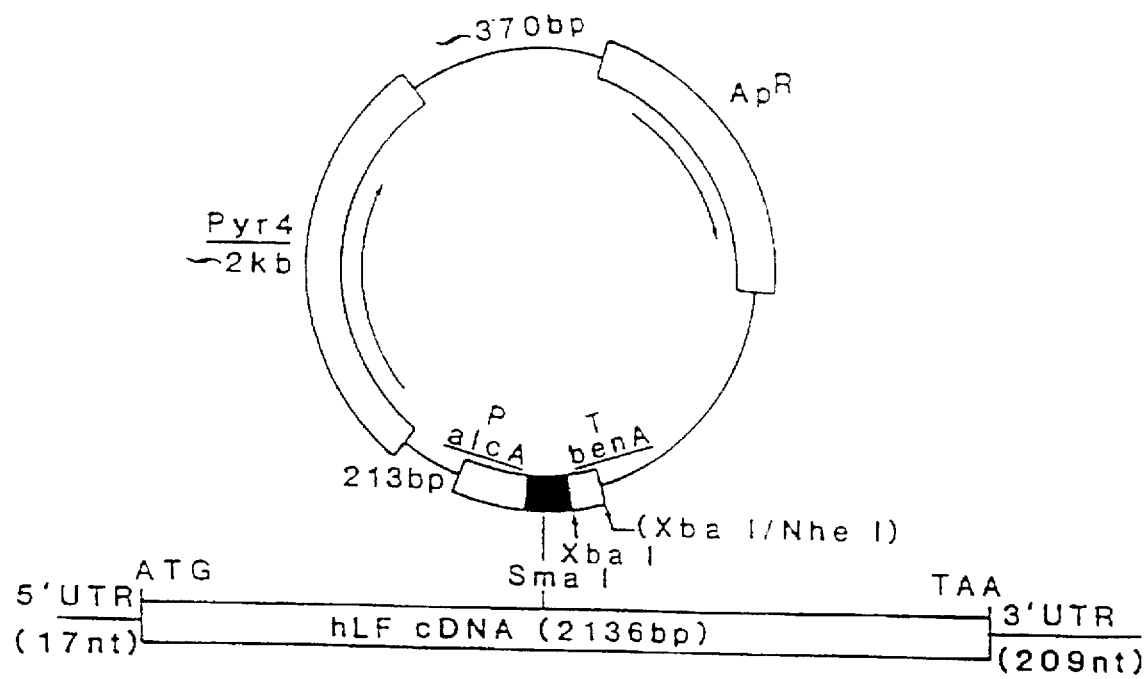
FIG. 17 is a schematic of the plasmid used for expression of the cDNA (SEQ. ID No. 1) in Aspergillis nidulans.

The plasmid used for expression of hLF cDNA is shown schematically in FIG. 17. The cDNA of SEQ. ID No. 1 as a 2.3-kb clone contained the secretory signal sequence and complete translation frame. The sequence of the entire cDNA was confirmed by dideoxy sequence analysis (Sequenase version 2.0, U.S. Biochemical, Cleveland, Ohio). The cDNA was repaired using the PolIk and subcloned into AccI-digested and blunt-ended pGEM4. The plasmid, pGEMhLF, was digested with HindIII +Asp718 and repaired using PolIk. The resulting 2.3-kb hLF fragment was subcloned into a unique SmaI site located in the multiple cloning cassette of pAL3 downstream from the alcA promoter. Waring. R. B., et al., *Gene*, 79, 119–130 (1989), generating pAL3hLF. The β-tubulin transcription terminator fragment was obtained by digesting the 3'-untranslated region of the benA gene (nt 2569–2665; May et al., 1987) with XbaI +NheI and subcloned into XbaI-digested pAL3hLF generating pAL3hLFT. This plasmid was used to transform *A. nidulans* strain GR5 (pyrG89; wa3; pyroA4)

The *A.nidulans* expression plasmid, pAL3hLFT, contains 300 bp of 55'-flanking sequence of the *A. nidulans* alcA gene containing all the regulatory elements necessary for controlled gene expression. To construct pALhLFT, a 2.3-kb hLF cDNA fragment containing 17 nucleotides of 5'-UTR, the complete hLF ORF encoding the secretory signal peptide and mature hLF, followed by 209 nt of 3' UTR was subcloned into a unique SmaI site in pAL3 downstream from the alcA promoter. A 96-bp terminator fragment from the *A. nidulans* β-tubulin-encoding (benA) gene was subcloned into a unique XbaI site downstream from the hLF cDNA sequence. The plasmid also contains an $Ap^R$ maker and the *N. crassa* pyr4 selectable marker (Waring et al., supra, 1989).

Transformation and Southern Analysis

Transformation was carried out as described by May et al., *J. Cell Beol.*, 109, 2267–2274 (1989). Protoplasts were transformed with 3 µg of the expression plasmid with an efficiency of 40 transformants/µg DNA. Transformats obtained were purified three times through conidial spores. Southern blot analysis was performed to confirm that transformants contained integrated plasmid with hLF cDNA. A hLF-specific radiolabelled band was detected at the expected size (2.3 kb) in lanes 1–10 but not in DNA from control spores. These results demonstrate that hLF cDNA was integrated into the genome of all *A. nidulans* transformants tested and varied randomly from one copy (transformants Nos. 3, 6 and 10) to 20 copies (No. 5) per cell. The site of integration of the plasmid into the *A. nidulans* genome is random due to the absence of homologous sequences to target the vector into a particular site.

Southern blot analysis was conducted of transformed *A. nidulans*. Genomic DNA was isolated from ten individual *A.*

*nidulans* (GR5) transformats and untransformed spores as described by Rasmussen, C. D. et al., *J. Biol. Chem.*, 265, 13767–13775 (1990). The DNA (1 μg) was digested with EcoRI, size fractionated on a 0.8% agarose gel and transferred to a nitrocellulose filter and hybridized with a radio-labelled hLF cDNA probe (2.1-kb). A sample (20 ng) of hLF cDNA was used as a positive control (hLF cDNA). Prehybridization and hybridization of the filter was performed in 6×SSC/0.1% SDS/0.5% dried milk at 65° C. for 16 h. The hybridization solution contained 200 ng of $^{32}$P probe (2.1 kb; specific activity $4\times10^8$ cpm/μg of DNA). Filters were washed in 2×SSC/0.5%SDS at 68° C. for 30 min followed by 0.5×SSC/0.5% SDS at 68° C. for 30 min. The filter was dried and exposed to Kodak X-AR5 film at –70° C. for 30 min and developed by autoadiograpy. The autoradiography showed an intense 2.1 kb band for hLF.

Production of hLF in *Aspergillus nidulans*

Conidia ($1\times10^6$/ml) were cultured in minimal media utilizing 100 mM Na acetate pH 6.5 as carbon source with or without addition of 1.2% ethanol to induce transcription of the hLF cDNA. GR5 was cultured as above except for the addition of 5 mM uridine and 10 mM uracil. Media and mycelia were harvested and separated using Miracloth (Calbiochem, San Diego, Calif.). Mycelia (200 mg) were freeze-dried and lyophilized overnight. Total cellular extracts were prepared by homogenization in a glass teflon homogenizer using 1 ml of phosphate-buffered saline (PBS; 137 mM NaCl/2.7 mM KCl/4.3 mM $Na_2HPO_4 7H_2O$/1.4 mM $K_2HPO_4$ pH 7.4) in the presence of phenylmethylsulfonylfluorride (PMSF, 10 μg). The homogenate was centrifuged at 12000×g for 30 min at 4° C. and the supernatant containing the soluble fraction was recovered. The growth medium was concentrated by freeze drying and lyophilization and resuspended in 1/30 vol. in PBS pH 7.4. Protein concentration was determined using the Bradford reagent according to manufacturer's instructions (BioRad, Richmond, Calif.). Concentrated media samples containing 40 μg protein and soluble extracts (50 μg protein) were subjected to 0.1% SDS/7% PAGE, Laemmli, U.K., *Nature*, 227, 680–685 (1970). Purified lactoferrin (250 ng, Sigma, St. Louis, Mo.) was used as standard (hLF std). The resolved proteins were transferred to nitrocellulose filters electrophoretically using the Western blot procedure, Towbin, H., et al., *Proc. Natl. Acad. Sci. USA*, 76, 4350–4354 (1979). Filters were blocked with Tris-buffered saline (TBS, 0.05M Tris/0.15M NaCl pH 7.5) containing 2% dried milk and then incubated by 2 h in the same with the addition of a 1 μg/ml of a specific polyclonal IgG directed against hLF (Sigma, St. Louis, Mo.). Filter washes (5×10 min) were in TBS/0.05% Nonidet P-40 followed by incubation with 1 μCi of [$^{125}$I] protein A in BS/2% dried milk. The filter was washed (5×10 min) with TBS/0.05% Nonidet P-40, dried and exposed overnight to Kodak XAR5 film at –70° C. The flm was then developed by autoradiography. The autoradiographs demonstrate production of hLF. Western analysis was performed to determine if the hLF cDNA was expressed in the *A. nidulans* transformats under the control of the alcA promoter.

Conidia ($1\times10^6$/ml) from transformat No. 5, which contained the highest number of copies of integrated hLF cDNAs, and from untransformed GR5 were inoculated into minimal medium utilizing glucose as the carbon source. After 18 h, the cultures were harvested, washed and reinoculated into minimal medium supplemented with 1.2% ethanol and grown for an additional 12 or 24 h before harvesting the cultures. Cell extracts and samples of the growth medium were resolved by SDS-PAGE, transferred to nitrocellulose and immunoblotted using a specific polyclonal IgG directed against hLF. An immunoreactive band indistinguishable from native hLF was evident in the cells and growth medium from transformat No. 5 after 12 and 24 h growth only after ethanol induction. Cell extracts or growth medium obtained from untransformed GR5 did not contain an immunoreactive band even after addition of ethanol. These results demonstrate that hLF is expressed in transformed *A. nidulans* under the control of the alcA promoter.

Western analysis revealed hLF in the cells in all of the remaining transformants. In general there was a correlation between the plasmid copy number and the expression levels obtained. In the medium hLF was detected only with transformats containing multiple copies of integrated expressed plasmid (Nos. 1, 5, 7 and 10).

In order to monitor the levels of hLF produced in the system, a pilot fermentation of transformant No. 5 was carried out using the growth parameters described above. ELISA analysis. Vilja, P., et al., *J. Immunol. Methods*, 76, 73–83 (1985), using a specific biotinylated IgG directed against hLF demonstrated that the total level of recombinant hLF produced was 5 μg/ml with approx. 30% (1.5–2.0 μg/ml) of this material secreted into the medium.

Iron Binding Analysis of hLF.

To test if recombinant lactoferrin synthesized and secreted in *A. nidulans* has an iron binding capacity similar to authentic human lactoferrin, samples of the growth medium of transformant No. 5 and untransformed GR5 spores were examined using an $^{59}$Fe microfilter-binding assay to detect $^{59}$Fe-bound lactoferrin. Iron-binding ($^{59}$Fe) is detected in the medium from transformant No. 5 but not in the medium from control untransformed GR5 spores. These results indicate that hLF produced in *A. nidulans* is biologically active in its capacity to bind $^{59}$Fe.

The data demonstrate the successful production of biologically active hLF in *A. nidulans*.The levels of hLF produced in *A. nidulans* were approx. 5 μg/ml with 30% of the hFL secreted into the growth medium. The secreted hLF was identical to native breast milk LF with regard to size and immunoreactivity. Furthermore, the hLF was capable of binding iron. Although hLF has been reported to contain anti-fungal properties, neither the re-hLF nor native hLF when added to the growth medium, retarded the growth of this strain of *A. nidulans*.The production of biologically active hLF in *A. nidulans* will facilitate testing of possible nutritional and therapeutic uses of this protein.

EXAMPLE 16.

PRODUCTION OF DNA SEQUENCE SUBSTITUTION ANALOGS.

FIG. 18 shows the restriction enzyme cleavage sites in the SEQ I. D. No. 1 cDNA for cleavage by various endonucleases. Table 2 lists the alternative codons that code for the 20 common amino acids. DNA sequence substitution analogs that also code for human lactoferrin can be constructed by choosing alternate codons from Table 2 to alter the DNA Sequence between a pair of cleavage sites selected from FIG. 18. Alternative codons are assembled into a synthetic oligonucleotide by conventional methods and the synthetic oligo is substituted into the endonuclease treated DNA of Sequence ID. No. 1 by the methods described in "Molecular Cloning. A Laboratory Manual", 2d Edition, Cold Spring Harbor Laboratory Press (1989), to produce a substitution analog. Other methods generally known to those skilled in the art can also be employed to obtain substitution analogs of DNA sequences. The alteration of the DNA by cleavage and codon substitution maybe repeated to substitute substantial portions of the original DNA sequence with alternative codons without altering the protein expressed by the DNA of Sequence ID. No. 1. The same methods can of course be used to make substitution analogs of the cDNA of SEQ ID No. 3 and 5. Alteration of a DNA sequence which produces no change in the protein expressed by the DNA sequence might, for example, be conducted to increase protein expression in a particular host cell by increasing the occurrence of codons that correspond to amino acid tRNAs found in higher concentration in the host cell. Such altered DNA sequences for substitution analogs can be easily produced by those of ordinary skill in the art following the method set out above, or other alternative techniques for altering the DNA sequence while obtaining the same protein on expression. Substitution analogs can be obtained by substitution of oligonucleotides at restriction cleavage sites as described above, or by other equivalent methods that change the codons while preserving the amino acid sequence of the expressed protein.

TABLE 2

| AMINO ACID | CODONS |
| --- | --- |
| Phe | TTT |
|  | TCC |
| Leu | TTA |
|  | TTG |
|  | CTT |
|  | CTC |
|  | CTA |
|  | CTG |
| Ile | ATT |
|  | ATC |
|  | ATA |
| Met | ATG |
| Val | GTT |
|  | GTC |
|  | GTA |
|  | GTG |
| Ser | TCT |
|  | TCC |
|  | TCA |
|  | TCG |
|  | AGT |
|  | AGC |
| Pro | CCT |
|  | CCC |
|  | CCA |
|  | CCG |
| Thr | ACT |
|  | ACC |
|  | ACA |
|  | ACG |
| Ala | GCT |
|  | GCC |
|  | GCA |
|  | GCG |

TABLE 2-continued

| AMINO ACID | CODONS |
| --- | --- |
| Tyr | TAT |
|  | TAC |
| Gly | GGT |
|  | GGC |
|  | GGA |
|  | GGG |
| His | CAT |
|  | CAC |
| Gln | CAA |
|  | CAG |
| Asn | AT |
|  | AAC |
| Lys | AAA |
|  | AAG |
| Asp | GAT |
|  | GAC |
| Glu | GAA |
|  | GAG |
| Cys | TGT |
|  | TGC |
| Trp | TGG |
| Arg | CGT |
|  | CGC |
|  | CGA |
|  | CGG |
|  | AGA |
|  | AGG |
| TERMINATION SIGNALS | TAA |
|  | TAG |
|  | TGA |

In conclusion, it is seen that the present invention and the embodiments disclosed herein are well adapted to carry out the objectives and obtain the end set forth in this application. Certain changes can be made in the method and apparatus without parting from the spirit and scopes of this invention. It is realized that changes are possible and that it is fuirther intended that each element or step presided in any of the filing claims is to be understood as to referring to all equivalent elements or steps for accomplishing the essentially the same results in substantially the same or equivalent manner. It is intended to cover the invention broadly in whatever form its principles may be utilized. The present invention, therefore, is well adapted to carry out the objects and obtain the ends and advantages mentioned, as well as others inherent therein.

We claim:

1. A plasmid suitable for the expression in a transformed prokaryotic host cell of a human lactoferrin, or an iron-binding lobe thereof, said plasmid comprising a DNA sequence encoding a naturally-occurring human lactoferrin protein or an iron-binding lobe thereof and further comprising transcriptional and translational regulatory elements capable of regulating the expression of said lactoferrin-encoding DNA sequence in said transformed host cell.

2. A plasmid comprising:
   (a) a DNA sequence encoding an amino acid sequence selected from the group consisting of an amino acid sequence encoded by SEQ ID NO: 1, an amino acid sequence of a naturally-occurring allelic variant of SEQ ID NO: 1, and an amino acid sequence of an iron-binding lobe of a naturally-occurring human lactoferrin and,
   (b) a promoter, a translational initiation sequence, and transcription and translation termination sequences;

wherein said plasmid permits the expression of a naturally-occurring human lactoferrin or an iron-binding lobe of a naturally-occurring lactoferrin thereof in a transformed prokaryotic host cell.

3. The plasmid of claim 2, wherein said plasmid permits the expression in transformed prokaryotic host cell of a polypeptide comprising a single iron-binding lobe of a naturally-occurring human lactoferrin.

4. A plasmid comprising:
   (a) a DNA sequence encoding a N-terminal lactoferrin antibacterial domain which is encoded by SEQ ID NO: 1 and has the amino acid sequence of SEQ ID NO:2 from position 20 through position 71, inclusive, or is encoded by a naturally-occurring human lactoferrin variant allele and has the native amino acids from position 20 through 71 of the naturally-occurring precursor lactoferrin, and,
   (b) a promoter, a translational initiation sequence, and transcription and translation termination sequences;

wherein said plasmid permits the expression of said N-terminal lactoferrin bactericidal domain in a transformed prokaryotic host cell.

5. A prokaryotic host cell comprising the plasmid of claim 4.

6. The plasmid PT7-7hLF3'.

7. A prokaryotic host cell comprising the plasmid of claim 3.

8. A transformed prokaryotic host cell comprising the plasmid of claim 7.

* * * * *

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 2360 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO (iv) ANTI-SENSE: NO (vi) ORIGINAL SOURCE:
(A) ORGANISM: H. sapiens (xi) SEQUENCE DESCRIPTION: SEQ ID NO:1:

```
GAATTCCGAC CGCAGACATG AAACTTGTCT TCCTCGTCCT GCTGTTCCTC GGGGCCCTCG      60
GACTGTGTCT GGCTGGCCGT AGGAGAAGGA GTGTTCAGTG GTGCACCGTA TCCCAACCCG     120
AGGCCACAAA ATGCTTCCAA TGGCAAAGGA ATATGAGAAG AGTGCGTGGC CTCCTGTCA      180
GCTGCATAAA GAGAGACTCC CCCATCCAGT GTATCCAGGC CATTGCGGAA AACAGGGCCG     240
ATGCTGTGAC CCTTGATGGT GGTTTCATAT ACGAGGCAGG CCTGGCCCCC TACAAACTGC     300
GACCTGTAGC GGCGGAAGTC TACGGGACCG AAAGACAGCC ACGAACTCAC TATTATGCCG     360
TGGCTGTGGT GAAGAAGGGC GGCAGCTTTC AGCTGAACGA ACTGCAAGGT CTGAAGTCCT     420
GCCACACAGG CCTTCGCAGG ACCGCTGGAT GGAATGTGCC TATAGGGACA CTTCGTCCAT     480
TCTTGAATTG GACGGGTCCA CCTGAGCCCA TTGAGGCAGC TGTGGCCAGG TTCTTCTCAG     540
CCAGCTGTGT TCCCGGTGCA GATAAGGAC AGTTCCCCAA CCTGTGTCGC TGTGTGCGG      600
GGACAGGGGA AAACAAATGT GCCTTCTCCT CCCAGGAACC GTACTTCAGC TACTCTGGTG     660
CCTTCAAGTG TCTGAGAGAC GGGGCTGGAG ACGTGGCTTT TATCAGAGAG AGCACAGTGT     720
TTGAGGACCT GTCAGACGAG GCTGAAAGGG ACGAGTATGA GTTACTCTGC CAGACAACA      780
CTCGGAAGCC AGTGGACAAG TTCAAAGACT GCCATCTGGC CCGGGTCCCT TCTCATGCCG     840
TTGTGGCACG AAGTGTGAAT GGCAAGGAGG ATGCCATCTG GAATCTTCTC CGCCAGGCAC     900
AGGAAAAGTT TGGAAAGGAC AAGTCACCGA AATTCCAGCT CTTTGGCTCC CTAGTGGGC      960
AGAAAGATCT GCTGTTCAAG GACTCTGCCA TTGGGTTTTC GAGGGTGCCC CCGAGGATAG    1020
ATTCTGGGCT GTACCTTGGC TCCGGCTACT TCACTGCCAT CCAGAACTTG AGGAAAAGTG    1080
AGGAGGAAGT GGCTGCCCGG CGTGCGCGGG TCGTGTGGTG TGCGGTGGGC GAGCAGGAGC    1140
TGCGCAAGTG TAACCAGTGG AGTGGCTTGA GCGAAGGCAG CGTGACCTGC TCCTCGGCCT    1200
CCACCACAGA GGACTGCATC GCCCTGGTGC TGAAAGGAGA AGCTGATGCC ATGAGTTTGG    1260
ATGGAGGATA TGTGTACACT GCAGGCAAAT GTGGTTTGGT GCCTGTCCTG GCAGAGAACT    1320
ACAAATCCCA ACAAAGCAGT GACCCTGATC CTAACTGTGT GGATAGACCT GTGGAAGGAT    1380
ATCTTGCTGT GGCGGTGGTT AGGAGATCAG ACACTAGCCT TACCTGGAAC TCTGTGAAAG    1440
GCAAGAAGTC CTGCCACACC GCCGTGGACA GGACTGCAGG CTGGAATATC CCCATGGGCC    1500
TGCTCTTCAA CCAGACGGGC TCCTGCAAAT TTGATGAATA TTTCAGTCAA AGCTGTGCCC    1560
CTGGGTCTGA CCCGAGATCT AATCTCTGTG CTCTGTGTAT TGGCGACGAG CAGGGTGAGA    1620
ATAAGTGCGT GCCCAACAGC AATGAGAGAT ACTACGGCTA CACTGGGGCT TTCCGGTGCC    1680
TGGCTGAGAA TGCTGGAGAC GTTGCATTTG TGAAAGATGT CACTGTCTTG CAGAACACTG    1740
ATGGAAATAA CAATGAGGCA TGGGCTAAGG ATTTGAAGCT GGCAGACTTT GCGCTGCTGT    1800
GCCTCGATGG CAAACGGAAG CCTGTGACTG AGGCTAGAAG CTGCCATCTT GCCATGGCCC    1860
CGAATCATGC CGTGGTGTCT CGGATGGATA AGGTGGAACG CCTGAAACAG GTGCTGCTCC    1920
ACCAACAGGC TAAATTTGGG AGAAATGGAT CTGACTGCCC GGACAAGTTT TGCTTATTCC    1980
AGTCTGAAAC CAAAAACCTT CTGTTCAATG ACAACACTGA GTGTCTGGCC AGACTCCATG    2040
GCAAAACAAC ATATGAAAAA TATTTGGGAC CACAGTATGT CGCAGGCATT ACTAATCTGA    2100
AAAAGTGCTC AACCTCCCCC CTCCTGGAAG CCTGTGAATT CCTCAGGAAG TAAAACCGAA    2160
GAAGATGGCC CAGCTCCCCA AGAAAGCCTC AGCCATTCAC TGCCCCAGC TCTTCTCCCC     2220
```

-continued

```
AGGTGTGTTG GGGCCTTGGC TCCCCTGCTG AAGGTGGGGA TTGCCCATCC ATCTGCTTAC        2280

AATTCCCTGC TGTCGTCTTA GCAAGAAGTA AAATGAGAAA TTTTGTTGAA AAAAAAAAA         2340

AAAAAAAAAA AAAAAAAAA                                                    2360
```

( 2 ) INFORMATION FOR SEQ ID NO:2:

( i ) SEQUENCE CHARACTERISTICS:
        ( A ) LENGTH: 711 amino acids
        ( B ) TYPE: amino acid
        ( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
        ( A ) ORGANISM: H. sapiens ( x i ) SEQUENCE DESCRIPTION: SEQ ID NO:2:

```
Met Lys Leu Val Phe Leu Val Leu Leu Phe Leu Gly Ala Leu Gly Leu
 1               5                  10                  15

Cys Leu Ala Gly Arg Arg Arg Ser Val Gln Trp Cys Thr Val Ser
            20                  25                  30

Gln Pro Glu Ala Thr Lys Cys Phe Gln Trp Gln Arg Asn Met Arg Arg
                35                  40                  45

Val Arg Gly Pro Pro Val Ser Cys Ile Lys Arg Asp Ser Pro Ile Gln
        50                  55                  60

Cys Ile Gln Ala Ile Ala Glu Asn Arg Ala Asp Ala Val Thr Leu Asp
 65                  70                  75                  80

Gly Gly Phe Ile Tyr Glu Ala Gly Leu Ala Pro Tyr Lys Leu Arg Pro
                85                  90                  95

Val Ala Ala Glu Val Tyr Gly Thr Glu Arg Gln Pro Arg Thr His Tyr
            100                 105                 110

Tyr Ala Val Ala Val Val Lys Lys Gly Gly Ser Phe Gln Leu Asn Glu
            115                 120                 125

Leu Gln Gly Leu Lys Ser Cys His Thr Gly Leu Arg Arg Thr Ala Gly
130                 135                 140

Trp Asn Val Pro Ile Gly Thr Leu Arg Pro Phe Leu Asn Trp Thr Gly
145                 150                 155                 160

Pro Pro Glu Pro Ile Glu Ala Ala Val Ala Arg Phe Phe Ser Ala Ser
                165                 170                 175

Cys Val Pro Gly Ala Asp Lys Gly Gln Phe Pro Asn Leu Cys Arg Leu
            180                 185                 190

Cys Ala Gly Thr Gly Glu Asn Lys Cys Ala Phe Ser Ser Gln Glu Pro
            195                 200                 205

Tyr Phe Ser Tyr Ser Gly Ala Phe Lys Cys Leu Arg Asp Gly Ala Gly
            210                 215                 220

Asp Val Ala Phe Ile Arg Glu Ser Thr Val Phe Glu Asp Leu Ser Asp
225                 230                 235                 240

Glu Ala Glu Arg Asp Glu Tyr Glu Leu Leu Cys Pro Asp Asn Thr Arg
                245                 250                 255

Lys Pro Val Asp Lys Phe Lys Asp Cys His Leu Ala Arg Val Pro Ser
            260                 265                 270

His Ala Val Val Ala Arg Ser Val Asn Gly Lys Glu Asp Ala Ile Trp
            275                 280                 285
```

```
Asn Leu Leu Arg Gln Ala Gln Glu Lys Phe Gly Lys Asp Lys Ser Pro
    290             295             300
Lys Phe Gln Leu Phe Gly Ser Pro Ser Gly Gln Lys Asp Leu Leu Phe
305                 310             315                         320
Lys Asp Ser Ala Ile Gly Phe Ser Arg Val Pro Pro Arg Ile Asp Ser
                325             330                         335
Gly Leu Tyr Leu Gly Ser Gly Tyr Phe Thr Ala Ile Gln Asn Leu Arg
            340                 345                 350
Lys Ser Glu Glu Val Ala Ala Arg Arg Ala Arg Val Val Trp Cys
        355             360             365
Ala Val Gly Glu Gln Glu Leu Arg Lys Cys Asn Gln Trp Ser Gly Leu
    370             375             380
Ser Glu Gly Ser Val Thr Cys Ser Ser Ala Ser Thr Thr Glu Asp Cys
385             390             395                         400
Ile Ala Leu Val Leu Lys Gly Glu Ala Asp Ala Met Ser Leu Asp Gly
            405             410             415
Gly Tyr Val Tyr Thr Ala Gly Lys Cys Gly Leu Val Pro Val Leu Ala
            420             425             430
Glu Asn Tyr Lys Ser Gln Gln Ser Ser Asp Pro Asp Pro Asn Cys Val
        435             440             445
Asp Arg Pro Val Glu Gly Tyr Leu Ala Val Ala Val Val Arg Arg Ser
    450             455             460
Asp Thr Ser Leu Thr Trp Asn Ser Val Lys Gly Lys Lys Ser Cys His
465             470             475                         480
Thr Ala Val Asp Arg Thr Ala Gly Trp Asn Ile Pro Met Gly Leu Leu
            485             490             495
Phe Asn Gln Thr Gly Ser Cys Lys Phe Asp Glu Tyr Phe Ser Gln Ser
            500             505             510
Cys Ala Pro Gly Ser Asp Pro Arg Ser Asn Leu Cys Ala Leu Cys Ile
        515             520             525
Gly Asp Glu Gln Gly Glu Asn Lys Cys Val Pro Asn Ser Asn Glu Arg
    530             535             540
Tyr Tyr Gly Tyr Thr Gly Ala Phe Arg Cys Leu Ala Glu Asn Ala Gly
545             550             555                         560
Asp Val Ala Phe Val Lys Asp Val Thr Val Leu Gln Asn Thr Asp Gly
                565             570                         575
Asn Asn Asn Glu Ala Trp Ala Lys Asp Leu Lys Leu Ala Asp Phe Ala
            580             585             590
Leu Leu Cys Leu Asp Gly Lys Arg Lys Pro Val Thr Glu Ala Arg Ser
        595             600             605
Cys His Leu Ala Met Ala Pro Asn His Ala Val Val Ser Arg Met Asp
    610             615             620
Lys Val Glu Arg Leu Lys Gln Val Leu Leu His Gln Gln Ala Lys Phe
625                 630             635                         640
Gly Arg Asn Gly Ser Asp Cys Pro Asp Lys Phe Cys Leu Phe Gln Ser
                645             650             655
Glu Thr Lys Asn Leu Leu Phe Asn Asp Asn Thr Glu Cys Leu Ala Arg
            660             665             670
Leu His Gly Lys Thr Thr Tyr Glu Lys Tyr Leu Gly Pro Gln Tyr Val
        675             680             685
Ala Gly Ile Thr Asn Leu Lys Lys Cys Ser Thr Ser Pro Leu Leu Glu
    690             695             700
Ala Cys Glu Phe Leu Arg Lys
705             710
```

( 2 ) INFORMATION FOR SEQ ID NO:3:

( i ) SEQUENCE CHARACTERISTICS:
        ( A ) LENGTH: 2347 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Bos taurus ( x i ) SEQUENCE DESCRIPTION: SEQ ID NO:3:

```
GAGCCTTCGT TCCGGAGTCG CCCCAGGACG CCAGCCCATG AAGCTCTTCG TCCCCGCCCT    60
CCTGTCCCTT GGAGCCCTTG GACTGTGTCT GGCTGCCCCG AGGAAAAACG TTCGATGGTG   120
TACCATCTCC CAACCTGAGT GGTTCAAATG CCGCAGATGG CAGTGGAGGA TGAAGAAGCT   180
GGGTGCTCCC TCTATCACCT GTGTGAGGCG GGCCTTTGCC TTGGAATGTA TTCCGGGCAT   240
CGCGGAGAAA AAGGCGGATG CTGTGACCCT GGATGGTGGC ATGGTGTTTG AGGCGGGCCG   300
GGACCCCTAC AAACTGCGGC CAGTAGCAGC AGAGATCTAT GGGACGAAAG AGTCTCCCCA   360
AACCCACTAT TATGCTGTGG CCGTCGTGAA GAAGGGCAGC AACTTTCAGC TGGACCAGCT   420
GCAAGGCCGG AAGTCCTGCC ATACGGGCCT TGGCAGGTCC GCTGGGTGGA TCATCCCTAT   480
GGGAATCCTT CGCCCGTACT TGAGCTGGAC AGAGTCACTC GAGCCCCTCC AGGGAGCTGT   540
GGCTAAATTC TTCTCTGCCA GCTGTGTTCC CTGCATTGAT AGACAAGCAT ACCCCAACCT   600
GTGTCAACTG TGCAAGGGGG AGGGGAGAA CCAGTGTGCC TGCTCCTCCC GGAACCATA   660
CTTCGGTTAT CTGGTGCCT TCAAGTGTCT GCAGGACGGG GCTGGAGACG TGGCTTTTGT   720
TAAAGAGACG ACAGTGTTTG AGAACTTGCC AGAGAAGGCT GACAGGGACC AGTATGAGCT   780
TCTCTGCCTG AACAACAGTC GGGCGCCAGT GGATGCGTTC AAGGAGTGCC ACCTGGCCCA   840
GGTCCCTTCT CATGCTGTCG TGGCCCGAAG TGTGGATGGC AAGGAAGACT TGATCTGGAA   900
GCTTCTCAGC AAGGCGCAGG AGAAATCTGG AAAAAACAAG TCTCGGAGCT TCCAGCTCTT   960
TGGCTCTCCA CCCGGCCAGA GGGACCTGCT GTTCAAAGAC TCTGCTCTTG GGTTTTTGAG  1020
GATCCCCTCG AAGGTAGATT CGGCGCTGTA CCTGGGCTCC CGCTACTTGA CCACCTTGAA  1080
GAACCTCAGG GAAACTGCGG AGGAGGTGAA GGCGCGGTAC ACCAGGGTCG TGTGGTGTGC  1140
CGTGGGACCT GAGGAGCAGA AGAAGTGCCA GCAGTGGAGC CAGCAGAGCG GCCAGAACGT  1200
GACCTGTGCC ACGGCGTCCA CCACTGACGA CTGCATCGTC CTGGTGCTGA AAGGGGAAGC  1260
AGATGCCCTG AACTTGGATG GAGGATATAT CTACACTGCG GGCAAGTGTG GCCTGGTGCC  1320
TGTCCTGGCA GAGAACCGGA AATCCTCCAA ACACAGTAGC CTAGATTGTG TGCTGAGACC  1380
AACGGAAGGG TACCTTGCCG TGGCAGTTGT CAAGAAAGCA AATGAGGGGC TCACATGGAA  1440
TTCTCTGAAA GACAAGAAGT CGTGCCACAC CGCCGTGGAC AGGACTGCAG GCTGGAACAT  1500
CCCCATGGGC CTGATCGTCA ACCAGACAGG CTCCTGCGCA TTTGATGAAT TCTTTAGTCA  1560
GAGCTGTGCC CCTGGGGCTG ACCCGAAATC CAGACTCTGT GCCTTGTGTG CTGGCGATGA  1620
CCAGGGCCTG GACAAGTGTG TGCCCAACTC TAAGGAGAAG TACTATGGCT ATACCGGGGC  1680
TTTCAGGTGC CTGGCTGAGG ACGTTGGGGA CGTTGCCTTT GTGAAAAACG ACACAGTCTG  1740
GGAGAACACG AATGGAGAGA GCACTGCAGA CTGGGCTAAG AACTTGAATC GTGAGGACTT  1800
```

-continued

```
CAGGTTGCTC TGCCTCGATG GCACCAGGAA GCCTGTGACG GAGGCTCAGA GCTGCCACCT    1860
GGCGGTGGCC CCGAATCACG CTGTGGTGTC TCGGAGCGAT AGGGCAGCAC ACGTGAAACA    1920
GGTGCTGCTC CACCAGCAGG CTCTGTTTGG GAAAAATGGA AAAACTGCC  CGGACAAGTT    1980
TTGTTTGTTC AAATCTGAAA CCAAAAACCT TCTGTTCAAT GACAACACTG AGTGTCTGGC    2040
CAAACTTGGA GGCAGACCAA CGTATGAAGA ATATTGGGG  ACAGAGTATG TCACGGCCAT    2100
TGCCAACCTG AAAAAATGCT CAACCTCCCC GCTTCTGGAA GCCTGCGCCT TCCTGACGAG    2160
GTAAAGCCTG CAAAGAAGCT AGCCTGCCTC CCTGGGCCTC AGCTCCTCCC TGCTCTCAGC    2220
CCCAATCTCC AGGCGCGAGG GACCTTCCTC TCCCTTCCTG AAGTCGGATT TTTGCCAAGC    2280
TCATCAGTAT TTACAATTCC CTGCTGTCAT TTAGCAAGA  AATAAAATTA GAAATGCTGT    2340
TGAAAAA                                                              2347
```

( 2 ) INFORMATION FOR SEQ ID NO:4:

( i ) SEQUENCE CHARACTERISTICS:
        ( A ) LENGTH: 708 amino acids
        ( B ) TYPE: amino acid
        ( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
        ( A ) ORGANISM: Bos taurus ( x i ) SEQUENCE DESCRIPTION: SEQ ID NO:4:

```
Met Lys Leu Phe Val Pro Ala Leu Leu Ser Leu Gly Ala Leu Gly Leu
 1               5                  10                  15
Cys Leu Ala Ala Pro Arg Lys Asn Val Arg Trp Cys Thr Ile Ser Gln
            20                  25                  30
Pro Glu Trp Phe Lys Cys Arg Arg Trp Gln Trp Arg Met Lys Lys Leu
        35                  40                  45
Gly Ala Pro Ser Ile Thr Cys Val Arg Arg Ala Phe Ala Leu Glu Cys
    50                  55                  60
Ile Pro Gly Ile Ala Glu Lys Lys Ala Asp Ala Val Thr Leu Asp Gly
65                  70                  75                  80
Gly Met Val Phe Glu Ala Gly Arg Asp Pro Tyr Lys Leu Arg Pro Val
                85                  90                  95
Ala Ala Glu Ile Tyr Gly Thr Lys Glu Ser Pro Gln Thr His Tyr Tyr
            100                 105                 110
Ala Val Ala Val Val Lys Lys Gly Ser Asn Phe Gln Leu Asp Gln Leu
        115                 120                 125
Gln Gly Arg Lys Ser Cys His Thr Gly Leu Gly Arg Ser Ala Gly Trp
    130                 135                 140
Ile Ile Pro Met Gly Ile Leu Arg Pro Tyr Leu Ser Trp Thr Glu Ser
145                 150                 155                 160
Leu Glu Pro Leu Gln Gly Ala Val Ala Lys Phe Phe Ser Ala Ser Cys
                165                 170                 175
Val Pro Cys Ile Asp Arg Gln Ala Tyr Pro Asn Leu Cys Gln Leu Cys
            180                 185                 190
Lys Gly Glu Gly Glu Asn Gln Cys Ala Cys Ser Ser Arg Glu Pro Tyr
        195                 200                 205
Phe Gly Tyr Ser Gly Ala Phe Lys Cys Leu Gln Asp Gly Ala Gly Asp
```

-continued

|     |     |     |     |     | 210 |     |     |     |     | 215 |     |     |     |     | 220 |     |     |     |     |
|---|---|---|---|---|---|---|---|---|---|---|---|---|---|---|---|---|---|---|---|
| Val 225 | Ala | Phe | Val | Lys 230 | Glu | Thr | Thr | Val | Phe 235 | Glu | Asn | Leu | Pro | Glu 240 | Lys |
| Ala | Asp | Arg | Asp | Gln 245 | Tyr | Glu | Leu | Leu | Cys 250 | Leu | Asn | Asn | Ser | Arg 255 | Ala |
| Pro | Val | Asp | Ala | Phe 260 | Lys | Glu | Cys | His 265 | Leu | Ala | Gln | Val | Pro 270 | Ser | His |
| Ala | Val | Val | Ala 275 | Arg | Ser | Val | Asp 280 | Gly | Lys | Glu | Asp | Leu 285 | Ile | Trp | Lys |
| Leu | Leu | Ser 290 | Lys | Ala | Gln | Glu 295 | Lys | Ser | Gly | Lys | Asn 300 | Lys | Ser | Arg | Ser |
| Phe 305 | Gln | Leu | Phe | Gly | Ser 310 | Pro | Pro | Gly | Gln | Arg 315 | Asp | Leu | Leu | Phe 320 | Lys |
| Asp | Ser | Ala | Leu | Gly 325 | Phe | Leu | Arg | Ile | Pro 330 | Ser | Lys | Val | Asp | Ser 335 | Ala |
| Leu | Tyr | Leu | Gly 340 | Ser | Arg | Tyr | Leu | Thr 345 | Leu | Lys | Asn | Leu | Arg 350 | Glu |
| Thr | Ala | Glu 355 | Glu | Val | Lys | Ala | Arg 360 | Tyr | Thr | Arg | Val | Val 365 | Trp | Cys | Ala |
| Val | Gly 370 | Pro | Glu | Glu | Gln | Lys 375 | Lys | Cys | Gln | Gln | Trp 380 | Ser | Gln | Gln | Ser |
| Gly 385 | Gln | Asn | Val | Thr | Cys 390 | Ala | Thr | Ala | Ser | Thr 395 | Thr | Asp | Asp | Cys 400 | Ile |
| Val | Leu | Val | Leu | Lys 405 | Gly | Glu | Ala | Asp | Ala 410 | Leu | Asn | Leu | Asp | Gly 415 | Gly |
| Tyr | Ile | Tyr | Thr 420 | Ala | Gly | Lys | Cys | Gly 425 | Leu | Val | Pro | Val | Leu 430 | Ala | Glu |
| Asn | Arg | Lys 435 | Ser | Ser | Lys | His | Ser 440 | Ser | Leu | Asp | Cys | Val 445 | Leu | Arg | Pro |
| Thr | Glu | Gly 450 | Tyr | Leu | Ala | Val | Ala 455 | Val | Val | Lys | Lys | Ala 460 | Asn | Glu | Gly |
| Leu 465 | Thr | Trp | Asn | Ser | Leu 470 | Lys | Asp | Lys | Lys | Ser 475 | Cys | His | Thr | Ala 480 | Val |
| Asp | Arg | Thr | Ala | Gly 485 | Trp | Asn | Ile | Pro | Met 490 | Gly | Leu | Ile | Val | Asn 495 | Gln |
| Thr | Gly | Ser | Cys 500 | Ala | Phe | Asp | Glu | Phe 505 | Phe | Ser | Gln | Ser | Cys 510 | Ala | Pro |
| Gly | Ala | Asp | 515 Pro | Lys | Ser | Arg | Leu 520 | Cys | Ala | Leu | Cys 525 | Ala | Gly | Asp | Asp |
| Gln | Gly 530 | Leu | Asp | Lys | Cys | Val 535 | Pro | Asn | Ser | Lys | Glu 540 | Lys | Tyr | Tyr | Gly |
| Tyr 545 | Thr | Gly | Ala | Phe | Arg 550 | Cys | Leu | Ala | Glu | Asp 555 | Val | Gly | Asp | Val 560 | Ala |
| Phe | Val | Lys | Asn | Asp 565 | Thr | Val | Trp | Glu | Asn 570 | Thr | Asn | Gly | Glu | Ser 575 | Thr |
| Ala | Asp | Trp | Ala 580 | Lys | Asn | Leu | Asn | Arg 585 | Glu | Asp | Phe | Arg | Leu 590 | Leu | Cys |
| Leu | Asp | Gly 595 | Thr | Arg | Lys | Pro | Val 600 | Thr | Glu | Ala | Gln | Ser 605 | Cys | His | Leu |
| Ala | Val | Ala 610 | Pro | Asn | His | Ala | Val 615 | Val | Ser | Arg | Ser 620 | Asp | Arg | Ala | Ala |
| His 625 | Val | Lys | Gln | Val | Leu 630 | Leu | His | Gln | Gln | Ala 635 | Leu | Phe | Gly | Lys 640 | Asn |

```
        Gly  Lys  Asn  Cys  Pro  Asp  Lys  Phe  Cys  Leu  Phe  Lys  Ser  Glu  Thr  Lys
                            645                      650                      655

Asn  Leu  Leu  Phe  Asn  Asp  Asn  Thr  Glu  Cys  Leu  Ala  Lys  Leu  Gly  Gly
                            660                      665                      670

Arg  Pro  Thr  Tyr  Glu  Glu  Tyr  Leu  Gly  Thr  Glu  Tyr  Val  Thr  Ala  Ile
                            675                      680                      685

Ala  Asn  Leu  Lys  Lys  Cys  Ser  Thr  Ser  Pro  Leu  Leu  Glu  Ala  Cys  Ala
                            690                      695                      700

Phe  Leu  Thr  Arg
        705
```

( 2 ) INFORMATION FOR SEQ ID NO:5:

( i ) SEQUENCE CHARACTERISTICS:
        ( A ) LENGTH: 2259 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Sus scrofa ( x i ) SEQUENCE DESCRIPTION: SEQ ID NO:5:

```
ACATGAAGCT  CTTCATCCCC  GCCCTGCTGT  TCCTCGGGAC  ACTTGGACTG  TGTCTGGCTG    60
CCCCTAAGAA  AGGGGTTCGA  TGGTGTGTCA  TATCCACAGC  AGAGTATTCA  AAATGCCGCC   120
AGTGGCAATC  AAAGATAAGA  AGAACTAATC  CCATGTTCTG  CATAAGGAGG  GCTTCTCCCA   180
CTGACTGTAT  CCGGGCCATC  GCGGCAAAAA  GGGCAGATGC  TGTGACCCTT  GATGGTGGTT   240
TGGTGTTTGA  AGCAGACCAG  TACAAACTGC  GGCCGGTAGC  AGCGGAGATC  TACGGGACAG   300
AAGAGAATCC  CCAAACCTAC  TATTATGCTG  TGGCTGTAGT  GAAGAAAGGT  TTCAACTTTC   360
AGAACCAGCT  ACAAGGTCGA  AAGTCCTGCC  ACACAGGCCT  TGGCAGGTCT  GCCGGGTGGA   420
ATATCCCTAT  AGGGTTACTT  CGCCGGTTCT  TGGACTGGGC  AGGGCCACCT  GAGCCCCTCC   480
AGAAAGCTGT  GGCCAAATTC  TTCTCTCAGA  GCTGTGTGCC  CTGCGCAGAT  GGAAATGCGT   540
ATCCCAACCT  GTGTCAGCTG  TGCATAGGGA  AAGGGAAAGA  TAAATGTGCT  TGTTCCTCCC   600
AGGAACCGTA  TTTTGGCTAT  TCCGGTGCCT  TCAACTGTCT  GCACAAAGGG  ATTGGAGATG   660
TGGCTTTTGT  CAAGGAGAGT  ACAGTGTTTG  AGAACCTGCC  ACAGAAGGCT  GACCGGGACA   720
AATACGAGCT  ACTCTGCCCA  GACAATACTC  GAAAGCCAGT  GGAAGCATTC  AGGGAGTGCC   780
ACCTTGCCCG  GGTCCCTTCT  CATGCTGTTG  TGGCCCGAAG  TGTGAATGGC  AAGGAGAACT   840
CCATCTGGGA  GCTTCTCTAC  CAGTCACAGA  AAAAGTTTGG  AAAAAGCAAT  CCACAGGAGT   900
TCCAGCTCTT  TGGCTCTCCT  GGTCAGCAGA  AGGACCTCCT  GTTTAGAGAT  GCTACCATCG   960
GGTTTTTGAA  GATCCCCTCA  AAGATAGATT  CTAAGCTGTA  CCTGGGCCTC  CCGTACCTTA  1020
CTGCCATCCA  GGGCCTGAGG  GAAACGGCAG  CGGAGGTGGA  GGCGCGGCAG  GCGAAGGTCG  1080
TGTGGTGCGC  CGTGGGTCCA  GAGGAGCTGC  GCAAGTGCCG  GCAGTGGAGC  AGCCAGAGCA  1140
GCCAGAACCT  GAACTGCAGC  CTGGCCTCCA  CCACCGAGGA  CTGCATCGTC  AGGTGCTGA   1200
AAGGAGAAGC  TGATGCTATG  AGCTTGGATG  GAGGATTTAT  CTACACTGCG  GGCAAGTGTG  1260
GTTTGGTGCC  TGTCCTGGCA  GAGAACCAAA  AATCTCGCCA  AAGCAGTAGC  TCAGACTGTG  1320
TGCATAGACC  AACACAAGGG  TATTTTGCCG  TGGCGGTTGT  CAGGAAAGCA  AATGGTGGTA  1380
```

```
TCACCTGGAA   CTCTGTGAGA   GGCACGAAGT   CCTGCCACAC   TGCTGTGGAC   AGGACAGCAG    1440

GCTGGAACAT   CCCCATGGGC   CTGCTTGTCA   ACCAGACAGG   CTCCTGCAAA   TTTGACGAAT    1500

TCTTTAGTCA   AAGCTGTGCT   CCTGGGTCTC   AGCCGGGATC   CAATCTCTGT   GCACTGTGTG    1560

TTGGCAATGA   CCAGGGCGTG   GACAAGTGTG   TGCCCAACAG   TAATGAGAGA   TACTATGGTT    1620

ACACCGGGGC   TTTCAGGTGC   CTGGCTGAGA   ATGCTGGGGA   TGTGGCGTTT   GTGAAAGATG    1680

TCACTGTCTT   GGACAACACG   AATGGACAGA   ACACAGAAGA   GTGGGCCAGG   GAATTGAGGT    1740

CAGATGACTT   TGAGCTGCTG   TGCCTTGATG   GCACCAGGAA   GCCTGTGACT   GAGGCTCAGA    1800

ACTGTCACCT   GGCTGTGGCC   CCCAGTCATG   CTGTGGTCTC   TCGGAAGGAA   AAGGCAGCAC    1860

AGGTGGAACA   GGTGCTACTC   ACTGAGCAGG   CTCAGTTTGG   AAGATACGGA   AAAGACTGCC    1920

CGGACAAGTT   TTGCTTGTTC   CGGTCTGAGA   CCAAAAACCT   TCTGTTCAAC   GACAACACGG    1980

AGGTTCTGGC   CCAACTCCAA   GGCAAAACAA   CATACGAAAA   ATATTTGGGA   TCAGAGTATG    2040

TCACAGCCAT   CGCTAACCTG   AAACAGTGCT   CAGTCTCCCC   GCTTCTGGAA   GCCTGTGCCT    2100

TCATGATGAG   GTAAAACCGG   AAAAGAAGCT   GCCCGCCTCC   CCAGGGGCCT   CAGCTTTCCC    2160

TCCTCCCGTC   TTGATTCCCA   GCTGCCCTGG   GCCTGCCTCT   CTCCCTTCCT   GAGGGCAGAC    2220

TTTGTTCAGC   TCATCCGTTT   TCACAATTCC   CTCGTGCCG                              2259
```

( 2 ) INFORMATION FOR SEQ ID NO:6:

( i ) SEQUENCE CHARACTERISTICS:
        ( A ) LENGTH: 703 amino acids
        ( B ) TYPE: amino acid
        ( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
        ( A ) ORGANISM: Sus scrofa ( x i ) SEQUENCE DESCRIPTION: SEQ ID NO:6:

```
Met  Lys  Leu  Phe  Ile  Pro  Ala  Leu  Leu  Phe  Leu  Gly  Thr  Leu  Gly  Leu
 1              5                        10                         15

Cys  Leu  Ala  Ala  Pro  Lys  Lys  Gly  Val  Arg  Trp  Cys  Val  Ile  Ser  Thr
           20                        25                        30

Ala  Glu  Tyr  Ser  Lys  Cys  Arg  Gln  Trp  Gln  Ser  Lys  Ile  Arg  Arg  Thr
                35                        40                        45

Asn  Pro  Met  Phe  Cys  Ile  Arg  Arg  Ala  Ser  Pro  Thr  Asp  Cys  Ile  Arg
      50                        55                        60

Ala  Ile  Ala  Ala  Lys  Arg  Ala  Asp  Ala  Val  Thr  Leu  Asp  Gly  Gly  Leu
 65                        70                        75                    80

Val  Phe  Glu  Ala  Asp  Gln  Tyr  Lys  Leu  Arg  Pro  Val  Ala  Ala  Glu  Ile
                     85                        90                        95

Tyr  Gly  Thr  Glu  Glu  Asn  Pro  Gln  Thr  Tyr  Tyr  Ala  Val  Ala  Val
                100                       105                       110

Val  Lys  Lys  Gly  Phe  Asn  Phe  Gln  Asn  Gln  Leu  Gln  Gly  Arg  Lys  Ser
           115                       120                       125

Cys  His  Thr  Gly  Leu  Gly  Arg  Ser  Ala  Gly  Trp  Asn  Ile  Pro  Ile  Gly
           130                       135                       140

Leu  Leu  Arg  Arg  Phe  Leu  Asp  Trp  Ala  Gly  Pro  Pro  Glu  Pro  Leu  Gln
145                       150                       155                  160
```

-continued

| | | | | | | | | | | | | | |
|---|---|---|---|---|---|---|---|---|---|---|---|---|---|
| Lys | Ala | Val | Ala | Lys<br>165 | Phe | Phe | Ser | Gln<br>170 | Ser | Cys | Val | Pro | Cys | Ala<br>175 | Asp |
| Gly | Asn | Ala | Tyr<br>180 | Pro | Asn | Leu | Cys | Gln<br>185 | Leu | Cys | Ile | Gly | Lys<br>190 | Gly | Lys |
| Asp | Lys | Cys<br>195 | Ala | Cys | Ser | Ser | Gln<br>200 | Glu | Pro | Tyr | Phe | Gly<br>205 | Tyr | Ser | Gly |
| Ala | Phe | Asn<br>210 | Cys | Leu | His | Lys<br>215 | Gly | Ile | Gly | Asp | Val<br>220 | Ala | Phe | Val | Lys |
| Glu<br>225 | Ser | Thr | Val | Phe | Glu<br>230 | Asn | Leu | Pro | Gln | Lys<br>235 | Ala | Asp | Arg | Asp | Lys<br>240 |
| Tyr | Glu | Leu | Leu | Cys<br>245 | Pro | Asp | Asn | Thr | Arg<br>250 | Lys | Pro | Val | Glu | Ala<br>255 | Phe |
| Arg | Glu | Cys | His<br>260 | Leu | Ala | Arg | Val | Pro<br>265 | Ser | His | Ala | Val | Val<br>270 | Ala | Arg |
| Ser | Val | Asn<br>275 | Gly | Lys | Glu | Asn | Ser<br>280 | Ile | Trp | Glu | Leu | Leu<br>285 | Tyr | Gln | Ser |
| Gln | Lys<br>290 | Lys | Phe | Gly | Lys | Ser<br>295 | Asn | Pro | Gln | Glu | Phe<br>300 | Gln | Leu | Phe | Gly |
| Ser<br>305 | Pro | Gly | Gln | Gln | Lys<br>310 | Asp | Leu | Leu | Phe | Arg<br>315 | Asp | Ala | Thr | Ile | Gly<br>320 |
| Phe | Leu | Lys | Ile | Pro<br>325 | Ser | Lys | Ile | Asp | Ser<br>330 | Lys | Leu | Tyr | Leu | Gly<br>335 | Leu |
| Pro | Tyr | Leu | Thr<br>340 | Ala | Ile | Gln | Gly | Leu<br>345 | Arg | Glu | Thr | Ala | Ala<br>350 | Glu | Val |
| Glu | Ala | Arg<br>355 | Gln | Ala | Lys | Val | Val<br>360 | Trp | Cys | Ala | Val | Gly<br>365 | Pro | Glu | Glu |
| Leu | Arg<br>370 | Lys | Cys | Arg | Gln | Trp<br>375 | Ser | Ser | Gln | Ser | Ser<br>380 | Gln | Asn | Leu | Asn |
| Cys<br>385 | Ser | Leu | Ala | Ser | Thr<br>390 | Thr | Glu | Asp | Cys | Ile<br>395 | Val | Gln | Val | Leu | Lys<br>400 |
| Gly | Glu | Ala | Asp | Ala<br>405 | Met | Ser | Leu | Asp | Gly<br>410 | Gly | Phe | Ile | Tyr | Thr<br>415 | Ala |
| Gly | Lys | Cys | Gly<br>420 | Leu | Val | Pro | Val | Leu<br>425 | Ala | Glu | Asn | Gln | Lys<br>430 | Ser | Arg |
| Gln | Ser | Ser<br>435 | Ser | Ser | Asp | Cys | Val<br>440 | His | Arg | Pro | Thr | Gln<br>445 | Gly | Tyr | Phe |
| Ala | Val<br>450 | Ala | Val | Val | Arg | Lys<br>455 | Ala | Asn | Gly | Gly | Ile<br>460 | Thr | Trp | Asn | Ser |
| Val<br>465 | Arg | Gly | Thr | Lys | Ser<br>470 | Cys | His | Thr | Ala | Val<br>475 | Asp | Arg | Thr | Ala | Gly<br>480 |
| Trp | Asn | Ile | Pro | Met<br>485 | Gly | Leu | Leu | Val | Asn<br>490 | Gln | Thr | Gly | Ser | Cys<br>495 | Lys |
| Phe | Asp | Glu | Phe<br>500 | Phe | Ser | Gln | Ser | Cys<br>505 | Ala | Pro | Gly | Ser | Gln<br>510 | Pro | Gly |
| Ser | Asn | Leu | Cys<br>515 | Ala | Leu | Cys | Val | Gly<br>520 | Asn | Asp | Gln | Gly<br>525 | Val | Asp | Lys |
| Cys | Val<br>530 | Pro | Asn | Ser | Asn | Glu<br>535 | Arg | Tyr | Tyr | Gly | Tyr<br>540 | Thr | Gly | Ala | Phe |
| Arg<br>545 | Cys | Leu | Ala | Glu | Asn<br>550 | Ala | Gly | Asp | Val | Ala<br>555 | Phe | Val | Lys | Asp | Val<br>560 |
| Thr | Val | Leu | Asp | Asn<br>565 | Thr | Asn | Gly | Gln | Asn<br>570 | Thr | Glu | Glu | Trp | Ala<br>575 | Arg |
| Glu | Leu | Arg | Ser<br>580 | Asp | Asp | Phe | Glu | Leu<br>585 | Leu | Cys | Leu | Asp | Gly<br>590 | Thr | Arg |

|     |     |     |     |     |     |     |     |     |     |     |     |     |     |     |
|-----|-----|-----|-----|-----|-----|-----|-----|-----|-----|-----|-----|-----|-----|-----|
| Lys | Pro | Val 595 | Thr | Glu | Ala | Gln | Asn 600 | Cys | His | Leu | Ala | Val 605 | Ala | Pro | Ser |
| His | Ala 610 | Val | Val | Ser | Arg | Lys 615 | Glu | Lys | Ala | Ala | Gln 620 | Val | Glu | Gln | Val |
| Leu 625 | Leu | Thr | Glu | Gln | Ala 630 | Gln | Phe | Gly | Arg | Tyr 635 | Gly | Lys | Asp | Cys | Pro 640 |
| Asp | Lys | Phe | Cys | Leu 645 | Phe | Arg | Ser | Glu | Thr 650 | Lys | Asn | Leu | Leu | Phe 655 | Asn |
| Asp | Asn | Thr | Glu 660 | Val | Leu | Ala | Gln | Leu 665 | Gln | Gly | Lys | Thr | Thr 670 | Tyr | Glu |
| Lys | Tyr | Leu 675 | Gly | Ser | Glu | Tyr | Val 680 | Thr | Ala | Ile | Ala | Asn 685 | Leu | Lys | Gln |
| Cys | Ser 690 | Val | Ser | Pro | Leu | Leu 695 | Glu | Ala | Cys | Ala | Phe 700 | Met | Met | Arg |

( 2 ) INFORMATION FOR SEQ ID NO:7:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:7:

CTGGGTCGAC GTAGGAGAAG GAGTGTTCAG TGGTGC      36

( 2 ) INFORMATION FOR SEQ ID NO:8:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:8:

GCCGTAGACT TCCGCCGCTA CAGG      24

( 2 ) INFORMATION FOR SEQ ID NO:9:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:9:

GAGGTACCGA ATTCATGGTG TTTTGATCAT TTTAAATTTT TATAT      45

( 2 ) INFORMATION FOR SEQ ID NO:10:

( i ) SEQUENCE CHARACTERISTICS:
        ( A ) LENGTH: 45 base pairs
        ( B ) TYPE: nucleic acid
        ( C ) STRANDEDNESS: single ( D ) TOPOLOGY: linear ( i i i ) HYPOTHETICAL: NO ( i v ) ANTI-SENSE: NO ( x i ) SEQUENCE DESCRIPTION: SEQ ID NO:10:

AGCAGCTGCA GCCAAAGCAG GTGCCGCGAC CTGAAGGCCG TACAG      45

( 2 ) INFORMATION FOR SEQ ID NO:11:

( i ) SEQUENCE CHARACTERISTICS:
            ( A ) LENGTH: 27 base pairs
            ( B ) TYPE: nucleic acid
            ( C ) STRANDEDNESS: single
            ( D ) TOPOLOGY: linear ( i i i ) HYPOTHETICAL: NO ( i v ) ANTI-SENSE: NO ( x i ) SEQUENCE DESCRIPTION: SEQ ID NO:11:

CTGCCCGGGC GTAGGAGAAG GAGTGTT      27

( 2 ) INFORMATION FOR SEQ ID NO:12:

( i ) SEQUENCE CHARACTERISTICS:
            ( A ) LENGTH: 34 base pairs
            ( B ) TYPE: nucleic acid
            ( C ) STRANDEDNESS: single
            ( D ) TOPOLOGY: linear ( i i i ) HYPOTHETICAL: NO ( i v ) ANTI-SENSE: NO ( x i ) SEQUENCE DESCRIPTION: SEQ ID NO:12:

CATGGATCCT GTTTACGCA ATGGCTGGA TACA      34

( 2 ) INFORMATION FOR SEQ ID NO:13:

( i ) SEQUENCE CHARACTERISTICS:
            ( A ) LENGTH: 27 base pairs
            ( B ) TYPE: nucleic acid
            ( C ) STRANDEDNESS: single
            ( D ) TOPOLOGY: linear ( i i i ) HYPOTHETICAL: NO ( i v ) ANTI-SENSE: NO ( x i ) SEQUENCE DESCRIPTION: SEQ ID NO:13:

CGGAATTCAT GGTGTTTTGA TCATTTT      27

( 2 ) INFORMATION FOR SEQ ID NO:14:

( i ) SEQUENCE CHARACTERISTICS:
            ( A ) LENGTH: 52 base pairs
            ( B ) TYPE: nucleic acid
            ( C ) STRANDEDNESS: single
            ( D ) TOPOLOGY: linear ( i i i ) HYPOTHETICAL: NO ( i v ) ANTI-SENSE: NO ( x i ) SEQUENCE DESCRIPTION: SEQ ID NO:14:

TGGAATTCGA TCGCGGATCC GCAATGCATG CAGCCAAAGC AGGTGCCGCG AC      52